(12) United States Patent
Bai

(10) Patent No.: US 12,029,111 B2
(45) Date of Patent: Jul. 2, 2024

(54) OXYGEN HETEROCYCLIC COMPOUND, APPLICATION THEREOF AND ELECTRONIC DEVICE USING THE SAME

(71) Applicant: WUHAN CHINA STAR OPTOELECTRONICS SEMICONDUCTOR DISPLAY TECHNOLOGY CO., LTD., Wuhan (CN)

(72) Inventor: Keyan Bai, Wuhan (CN)

( * ) Notice: Subject to any disclaimer, the term of this patent is extended or adjusted under 35 U.S.C. 154(b) by 658 days.

(21) Appl. No.: 17/274,195

(22) PCT Filed: Dec. 17, 2020

(86) PCT No.: PCT/CN2020/137385
§ 371 (c)(1),
(2) Date: Mar. 8, 2021

(87) PCT Pub. No.: WO2022/110381
PCT Pub. Date: Jun. 2, 2022

(65) Prior Publication Data
US 2023/0041564 A1 Feb. 9, 2023

(30) Foreign Application Priority Data
Nov. 26, 2020 (CN) .......................... 202011345450.6

(51) Int. Cl.
*H01L 51/50* (2006.01)
*C07D 311/80* (2006.01)
*C07D 405/10* (2006.01)
*H10K 85/60* (2023.01)
*H10K 50/15* (2023.01)

(52) U.S. Cl.
CPC ......... *H10K 85/636* (2023.02); *C07D 311/80* (2013.01); *C07D 405/10* (2013.01); *H10K 85/633* (2023.02); *H10K 50/15* (2023.02); *H10K 85/615* (2023.02); *H10K 85/626* (2023.02); *H10K 85/6572* (2023.02); *H10K 85/6574* (2023.02)

(58) Field of Classification Search
None
See application file for complete search history.

(56) References Cited

FOREIGN PATENT DOCUMENTS

| CN | 111051292 A | 4/2020 |
| CN | 111094261 A | 5/2020 |
| CN | 111233676 A | 6/2020 |
| KR | 2015144487 | * 12/2005 |
| KR | 20150144487 A | 12/2015 |
| KR | 20160000284 A | 1/2016 |
| KR | 20180021339 A | 3/2018 |
| KR | 2019053698 | * 5/2019 ............. H10K 50/00 |

* cited by examiner

*Primary Examiner* — Gregory D Clark

(57) ABSTRACT

The present disclosure provides an oxygen heterocyclic compound, an application thereof, and an electronic device using the same. The oxygen heterocyclic compound has a structural formula as represented by following formula 1:

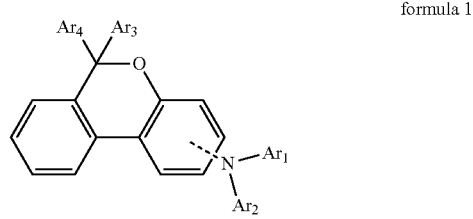

formula 1

The oxygen heterocyclic compound comprises an aromatic amine portion and an oxygen heterocyclic portion. The aromatic amine portion effectively promotes the hole injection and transport performance. The oxygen heterocyclic portion is conducive to the formation of molten evaporation materials.

8 Claims, No Drawings

OXYGEN HETEROCYCLIC COMPOUND, APPLICATION THEREOF AND ELECTRONIC DEVICE USING THE SAME

FIELD OF INVENTION

The present disclosure relates to an organic photoelectric material technical field, and specifically, to an oxygen heterocyclic compound, an application thereof, and an electronic device using the same.

BACKGROUND OF INVENTION

An organic electronic device refers to a device composed of an anode, a cathode, and an organic layer sandwiched between the anode and the cathode. The organic electronic device includes organic light-emitting diodes, organic solar cells, organic semiconductors, organic crystals, etc. The working principle of the organic electronic device is to apply an external voltage to the electrode to inject holes and electrons into the organic layer to form excitons, thereby radiating light, such as organic light-emitting diodes; or an external light source is absorbed by organic materials to form excitons, and the excitons are separated into holes and electrons which are transferred to the electrode and stored, such as organic solar cells. The following mainly describes organic light-emitting diodes.

The organic light-emitting diodes are devices that convert electrical energy into light energy. Its structure usually includes an anode, a cathode, and one or more layers of organic material layers between the anode and the cathode. The organic material layers are classified into a hole injection material layer, a hole transport material layer, an electron injection material layer, an electron transport material layer, and a light-emitting material layer according to its function. In addition, The light-emitting materials are classified into blue, sky blue, green, yellow, red, and deep red according to their luminous colors.

The evaluation indicators of organic light-emitting diodes are mainly voltage, efficiency and, lifespans. How to develop organic light-emitting diode devices with low voltage, high efficiency and long lifespans has always been the goal pursued by the R&D and business communities, which requires high-mobility electron/hole injection and transport materials, as well as high-efficiency light-emitting materials and effective balance between electrons and holes in the organic light-emitting diode devices. Furthermore, from the perspective of the mass production of organic materials, the vapor deposition type (sublimation type or melting type), decomposition temperature, glass transition temperature, and outgassing of the materials must also be considered. Especially in mass production, a thick hole transport material needs to be deposited. The sublimation material in the materials may seriously affect the uniformity of the film thickness in mass production. Therefore, the development of molten hole transport materials has become an important direction.

SUMMARY OF DISCLOSURE

Technical Problem

One embodiment in the present disclosure innovatively provides an oxygen heterocyclic compound and an application thereof, and an electronic device using the same. The organic material comprises an aromatic amine portion and an oxygen heterocyclic portion, wherein the aromatic amine portion may effectively promote the hole injection and transport performance of the organic material, and the oxygen heterocyclic portion is conducive to the formation of molten evaporation materials.

Technical Solutions

To achieve above technical objects, one aspect of the present disclosure discloses an oxygen heterocyclic compound having a structural formula as represented by following formula 1:

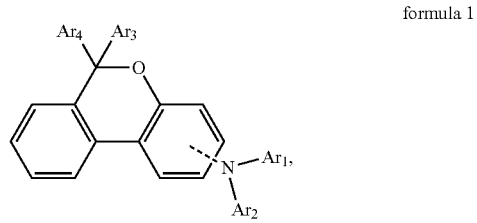

formula 1 wherein, $Ar_1$ and $Ar_2$ are independently selected from the group consisting of single or multiple substituted or unsubstituted aryl groups, and single or multiple substituted or unsubstituted heteroaryl groups; or $Ar_1$ and $Ar_2$ together form single or fused aromatic or heterocyclic ring when $Ar_1$ and $Ar_2$ are adjacent aryl groups or heteroaryl groups connected to each other, wherein heteroatoms of the heteroaryl groups are O, N, F, S, or Si; and $Ar_3$ and $Ar_4$ are independently selected from the group consisting of C1 to C22 alkyl groups, C1 to C22 alkoxy groups, C1 to C22 heteroalkyl groups, single or multiple substituted or unsubstituted aryl groups, and substituted or unsubstituted heteroaryl groups; or $Ar_3$ and $Ar_4$ together form a single or fused aromatic or heterocyclic ring when $Ar_3$ and $Ar_4$ are adjacent aryl groups or heteroaryl groups connected to each other, wherein heteroatoms of the heteroaryl groups are O, N, F, S, or Si.

Furthermore, the oxygen heterocyclic compound has a structural formula represented by following formula 2:

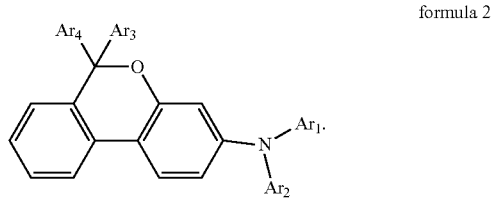

formula 2

Furthermore, for the oxygen heterocyclic compound, $Ar_1$ and $Ar_2$ are independently represented by any of following formula 301 to formula 332:

formula 301

-continued
formula 302
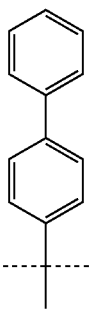
formula 303
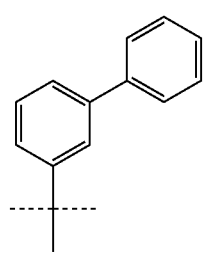
formula 304
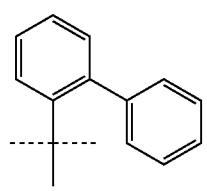
formula 305
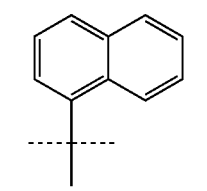
formula 306
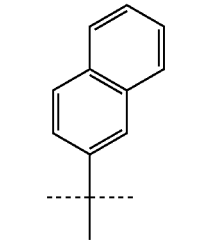
formula 307
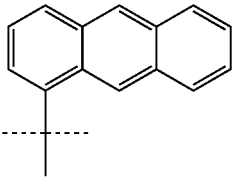
formula 308
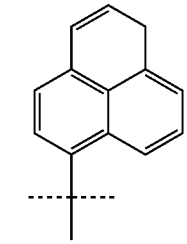
-continued
formula 309
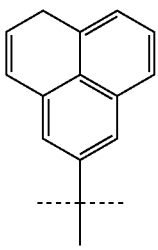
formula 310
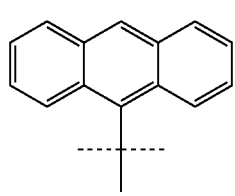
formula 311
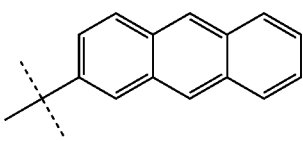
formula 312
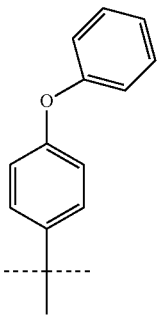
formula 313
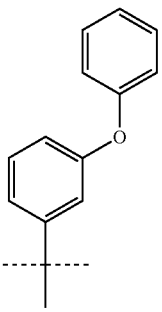
formula 314
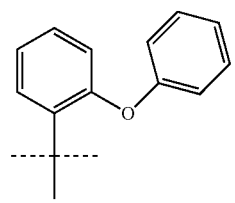

formula 315
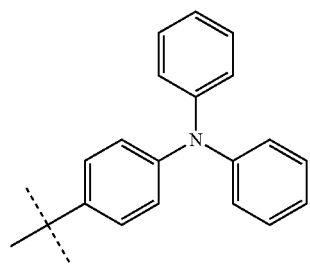
formula 316
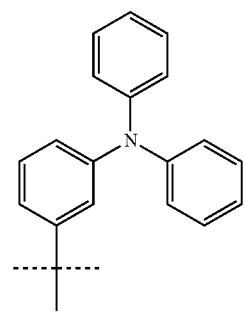
formula 317
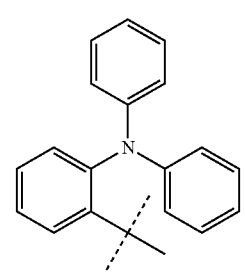
formula 318
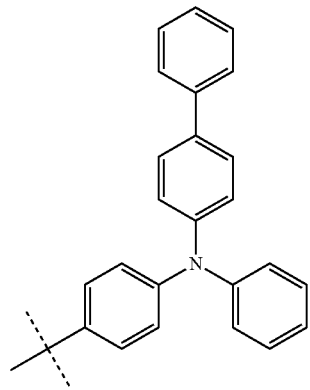
formula 319
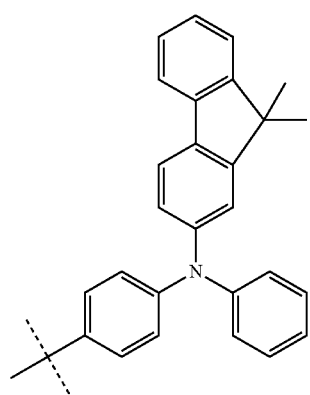
formula 320
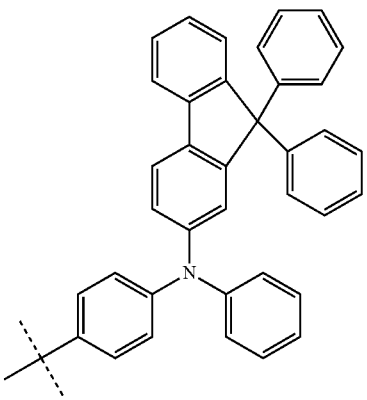
formula 321
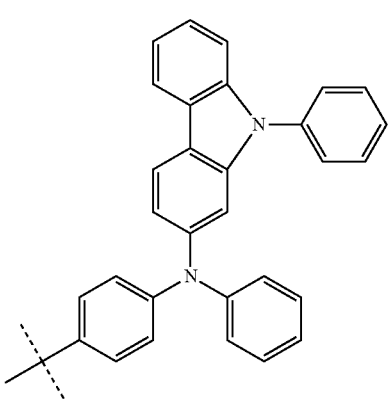
formula 322
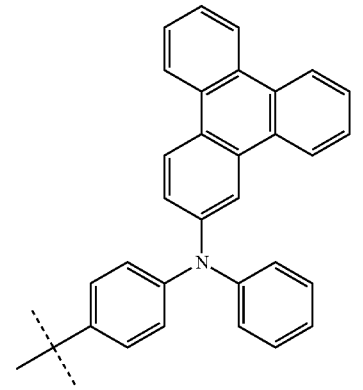
formula 323
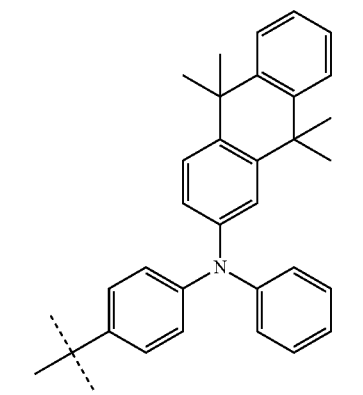

formula 324
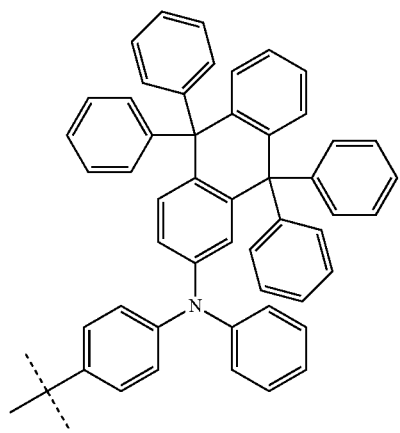
formula 325
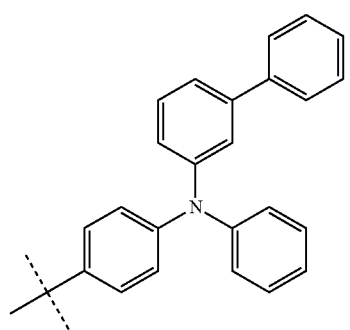
formula 326
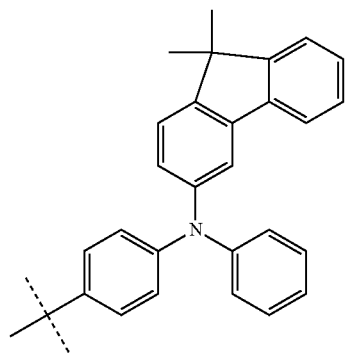
formula 327
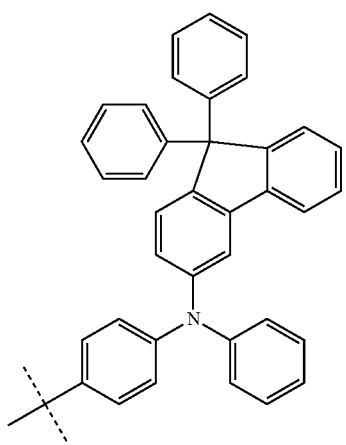
formula 328
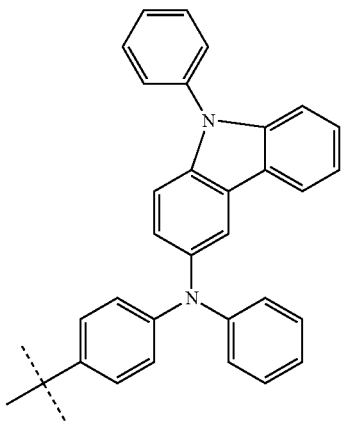
formula 329
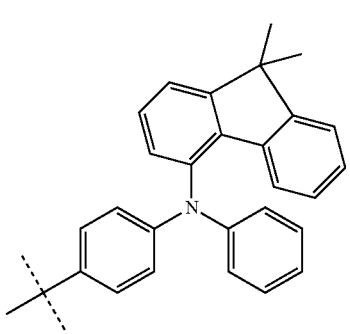
formula 330
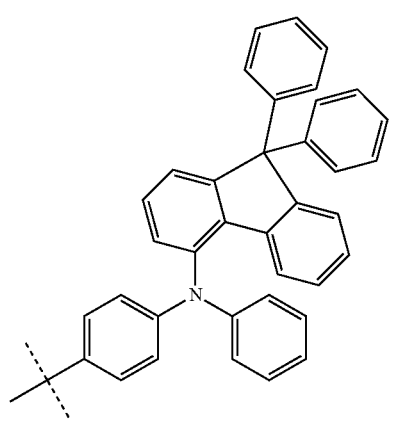
formula 331
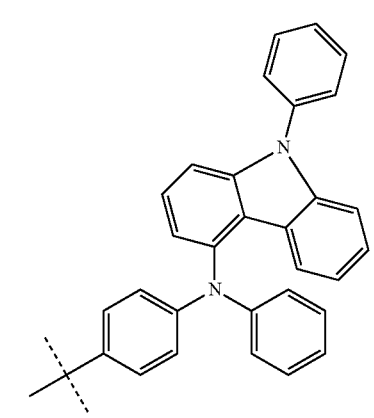

formula 332
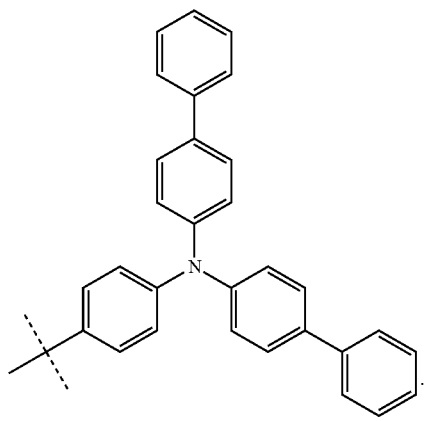
Furthermore, for the oxygen heterocyclic compound, Ar$_3$ and Ar$_4$ are independently represented by any of following formula 301 to formula 332 and formula 401 to formula 403:
formula 301
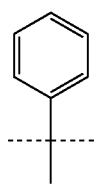
formula 302
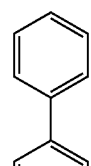
formula 303
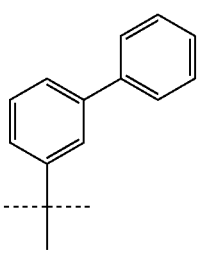
formula 304
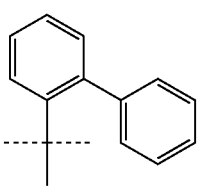
formula 305
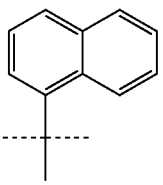
formula 306
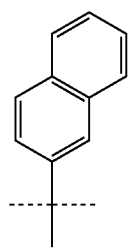
formula 307
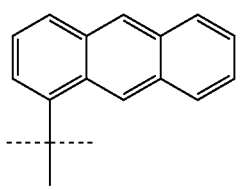
formula 308
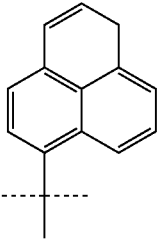
formula 309
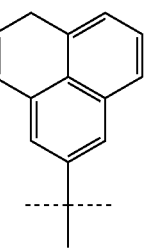
formula 310
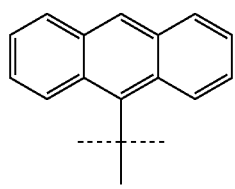
formula 311
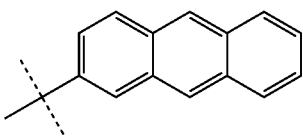

formula 312
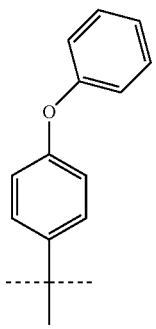
formula 313
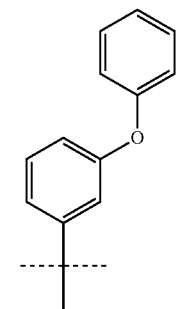
formula 314
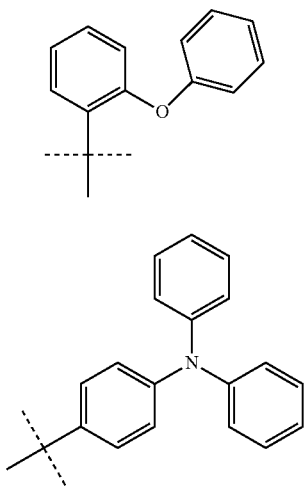
formula 315
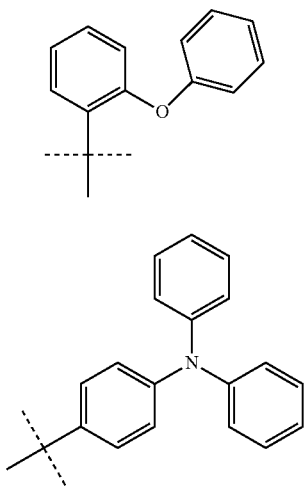
formula 316
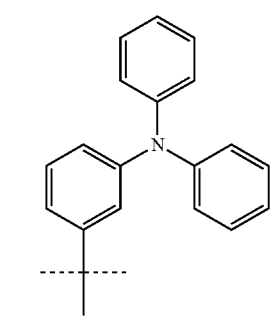
formula 317
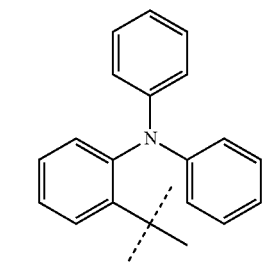
formula 318
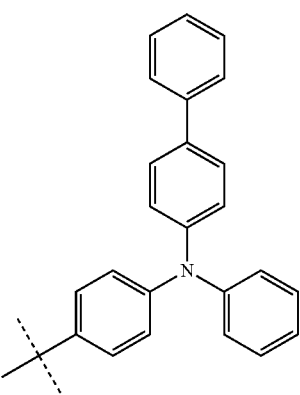
formula 319
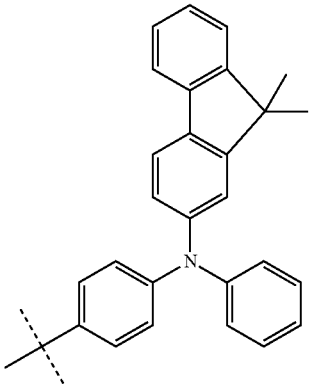
formula 320
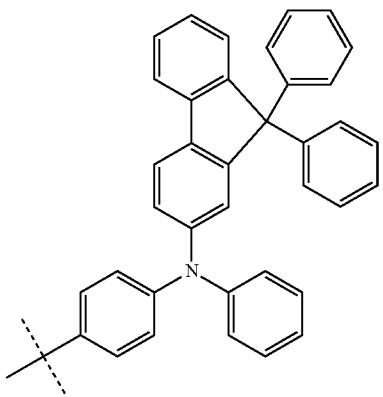

formula 321
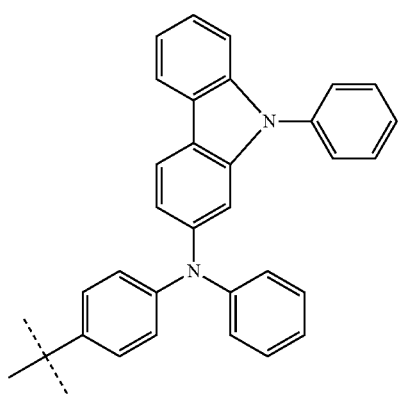
formula 322
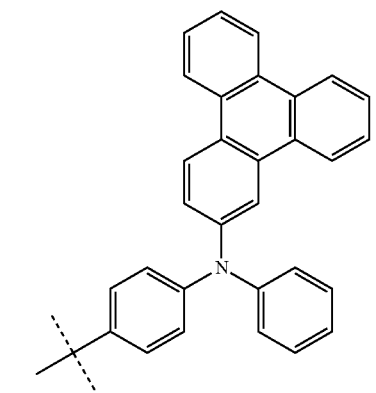
formula 323
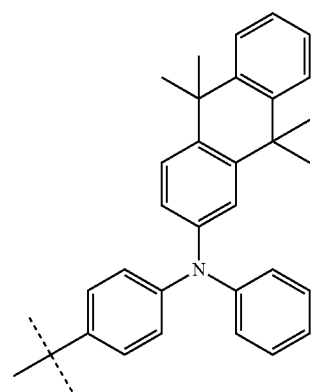
formula 324
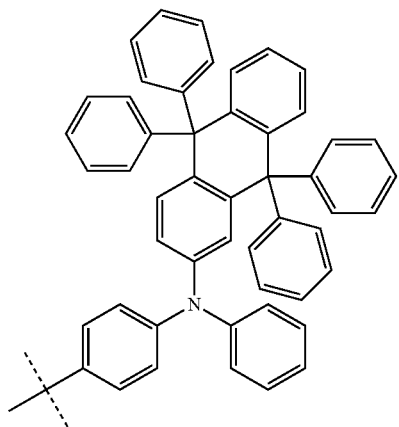
formula 325
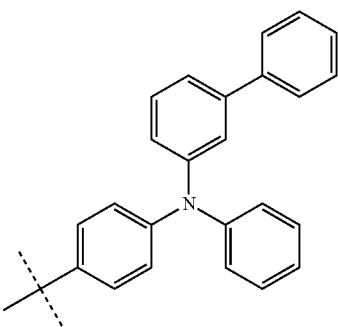
formula 326
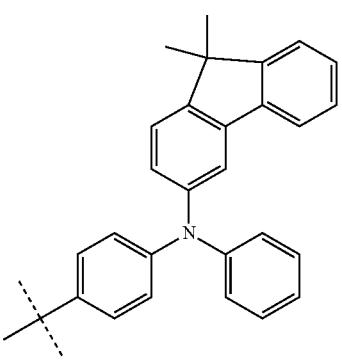
formula 327
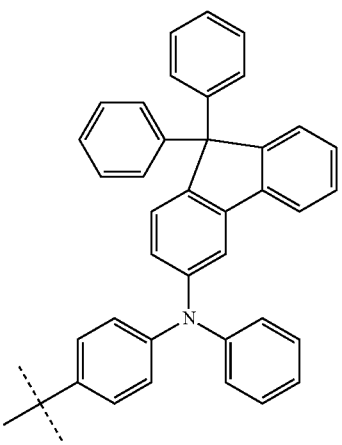
formula 328
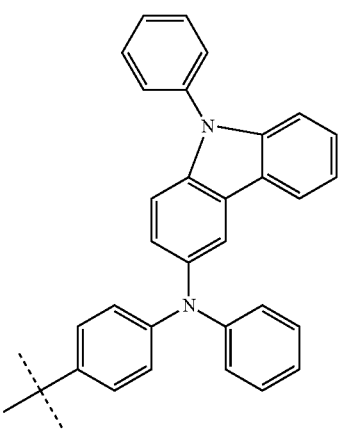

formula 329
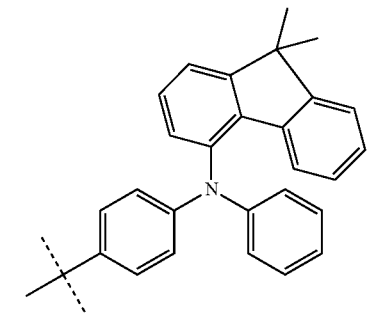
formula 330
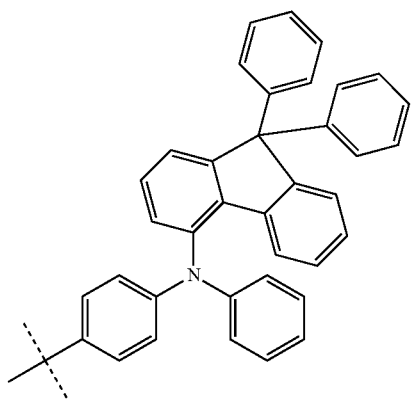
formula 331
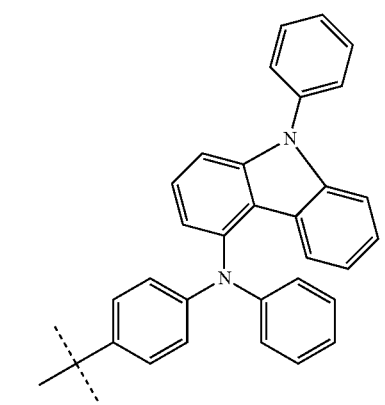
formula 332
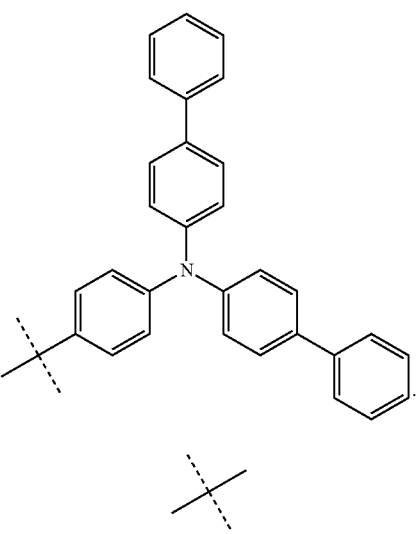
formula 401
formula 402
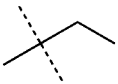
formula 403
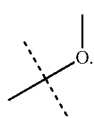
Furthermore, the oxygen heterocyclic compound has a structural formula represented by any of following formula 501 to formula 508:
formula 501
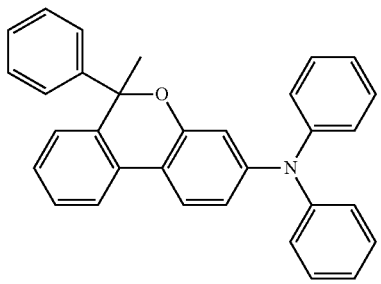
formula 502
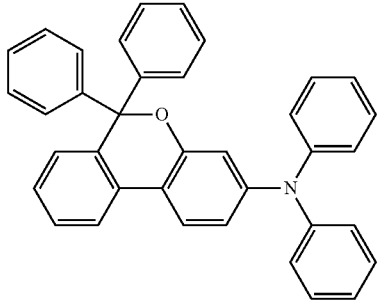
formula 503
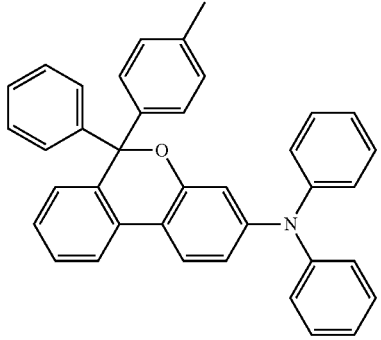

formula 504
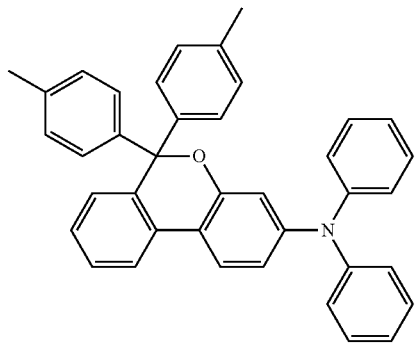
formula 505
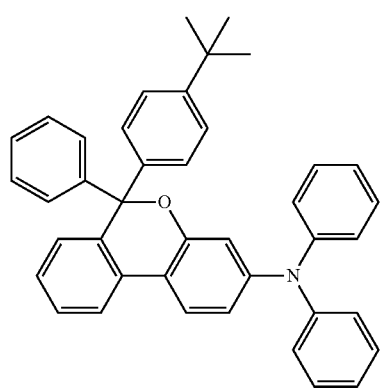
formula 506
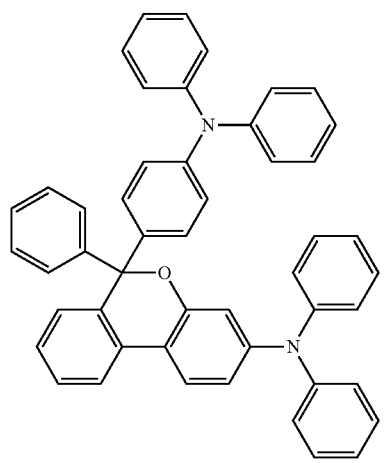
formula 507
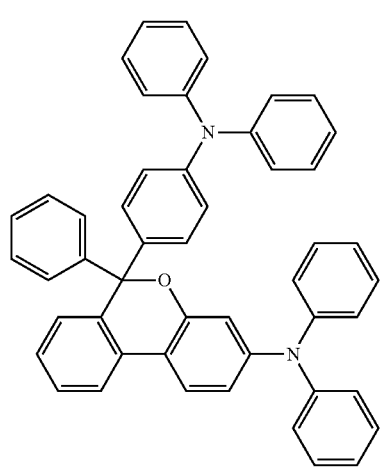
formula 508
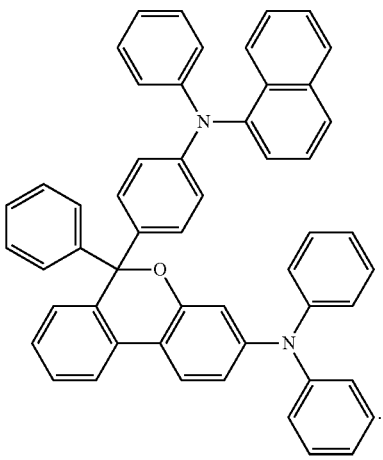
Furthermore, the oxygen heterocyclic compound has a structure as represented by any of following formula 601 to formula 617:
formula 601
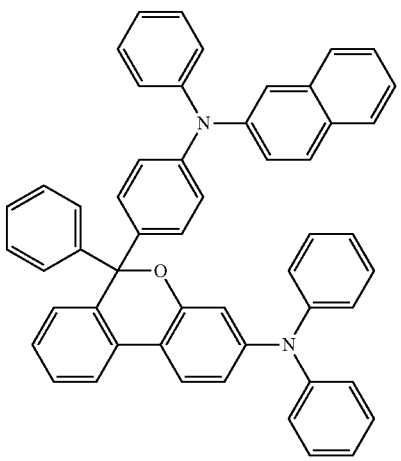
formula 602
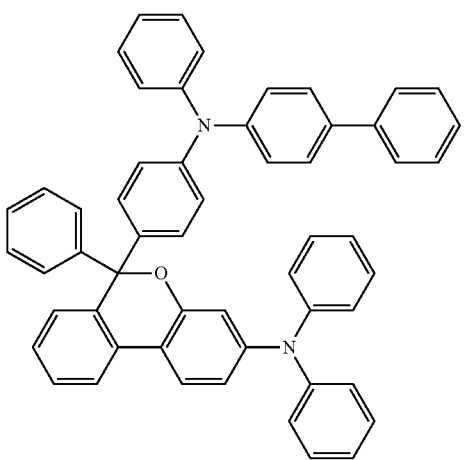

formula 603
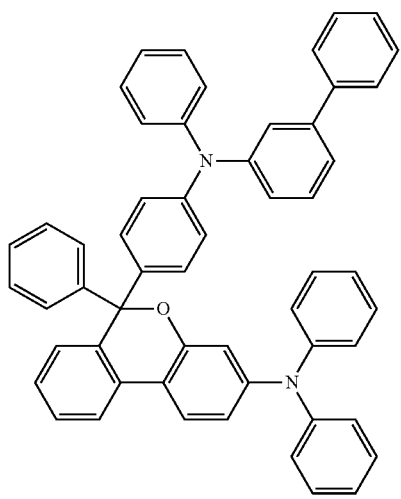
formula 604
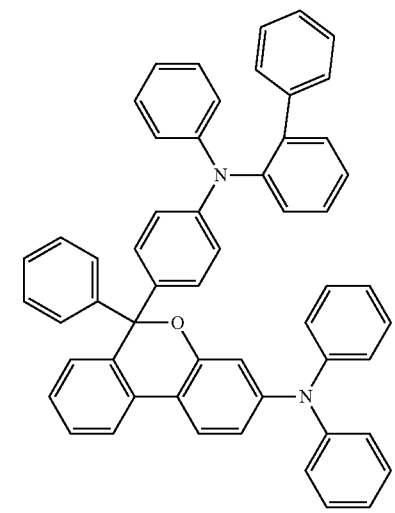
formula 605
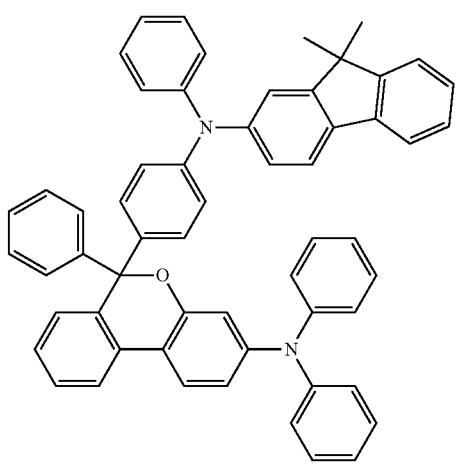
formula 606
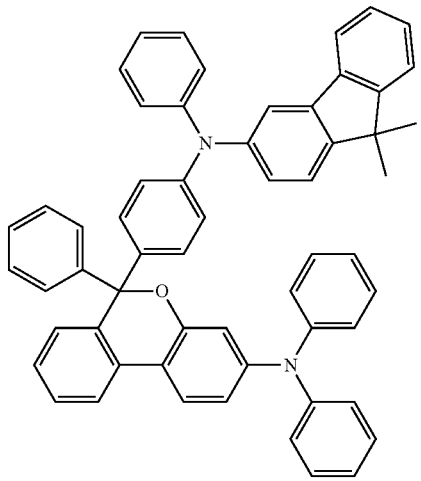
formula 607
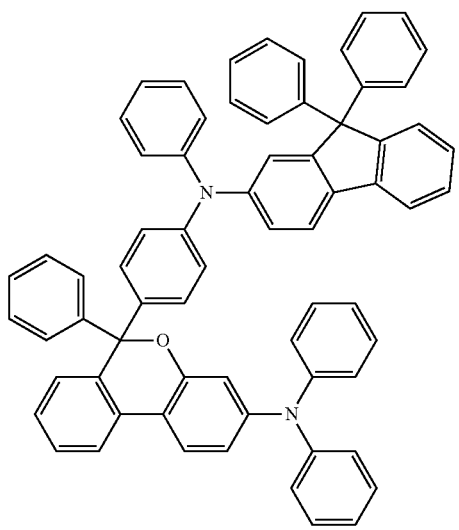
formula 608
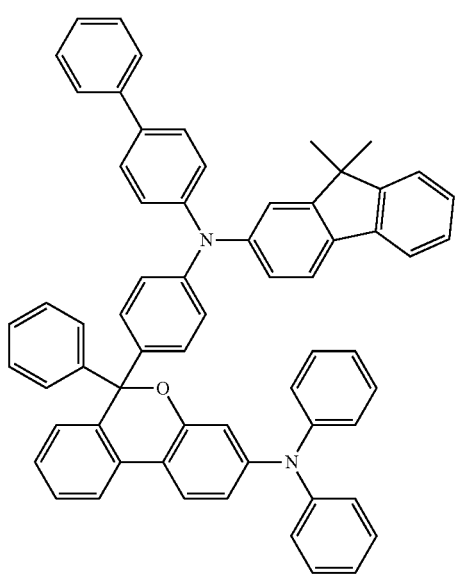

formula 609
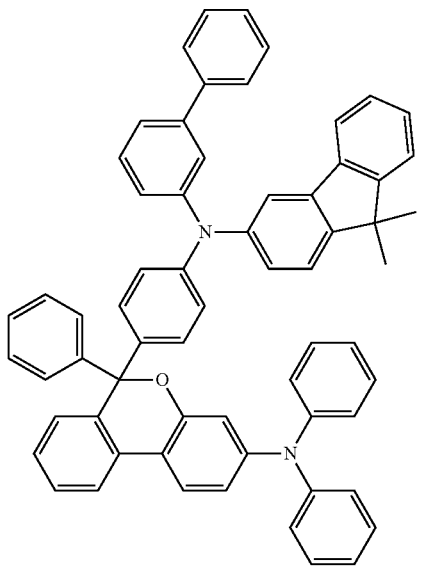
formula 610
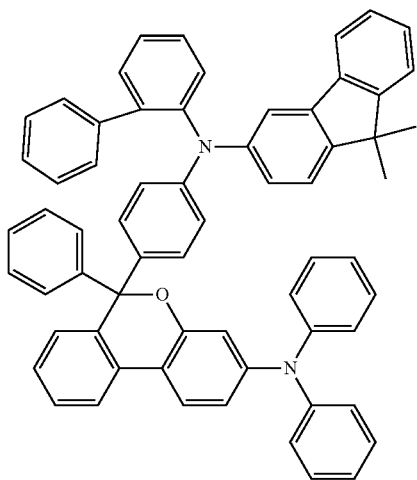
formula 611
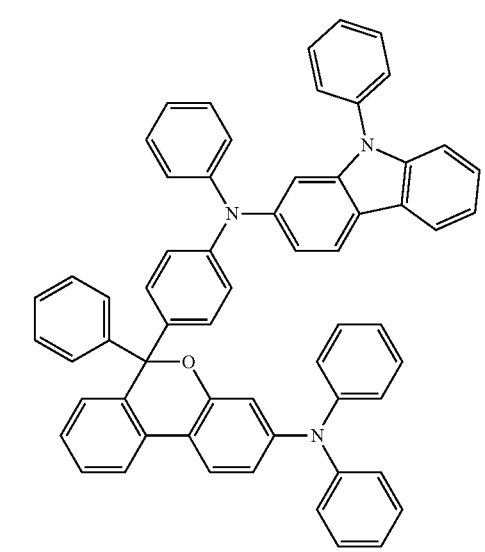
formula 612
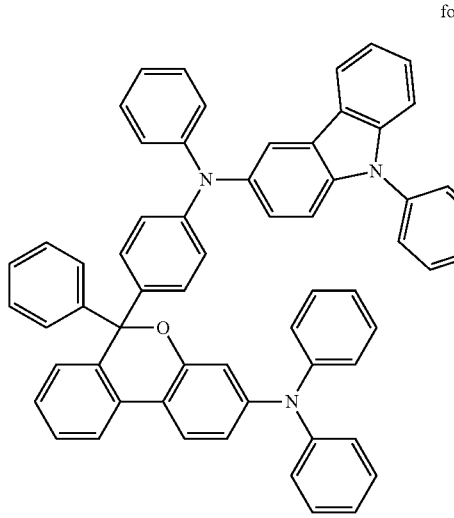
formula 613
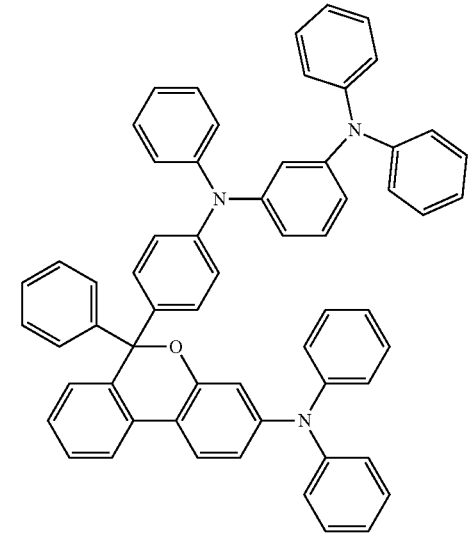
formula 614
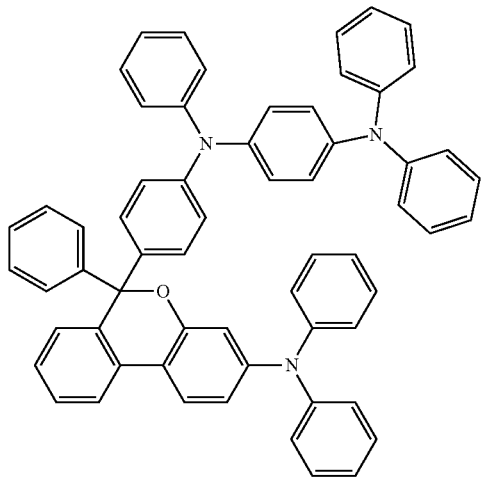

formula 615
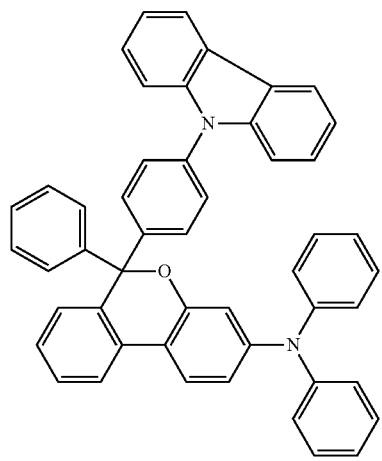
formula 616
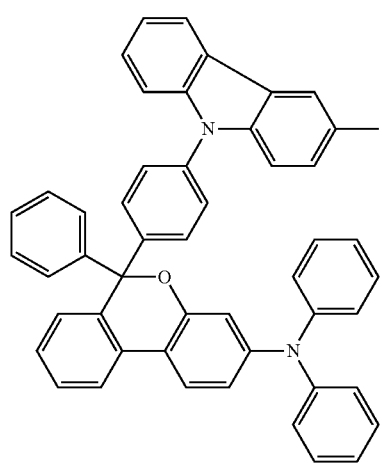
formula 617
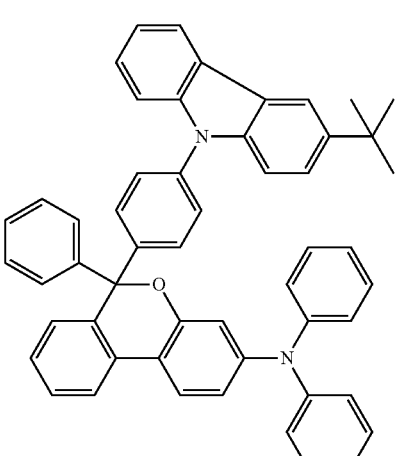
formula 701
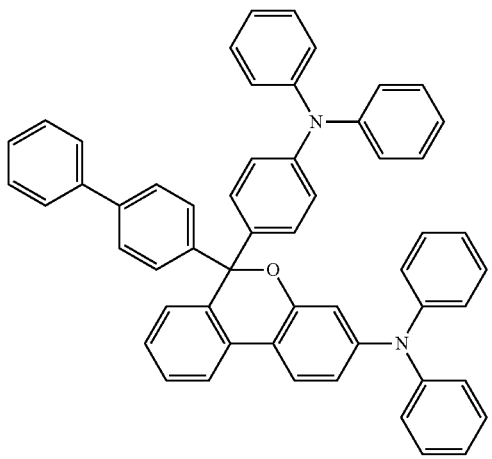
formula 702
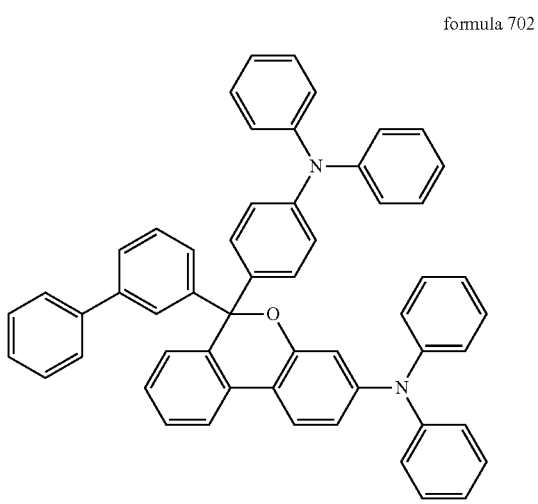
formula 703
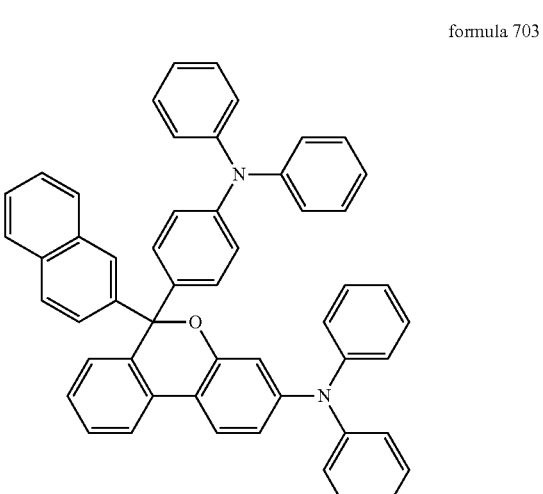
Furthermore, the oxygen heterocyclic compound has a structure as represented by any of following formula 701 to formula 722:

formula 704
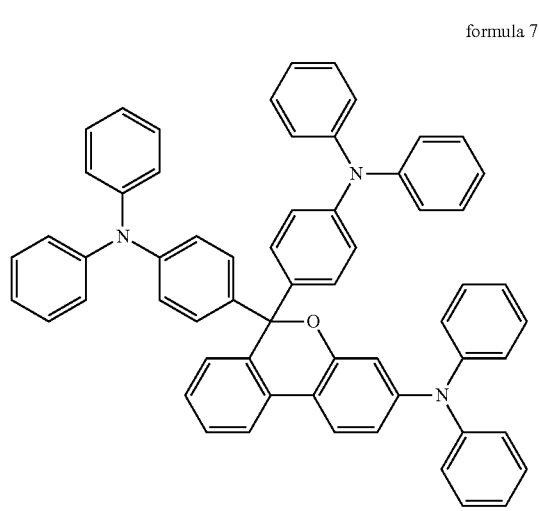
formula 707
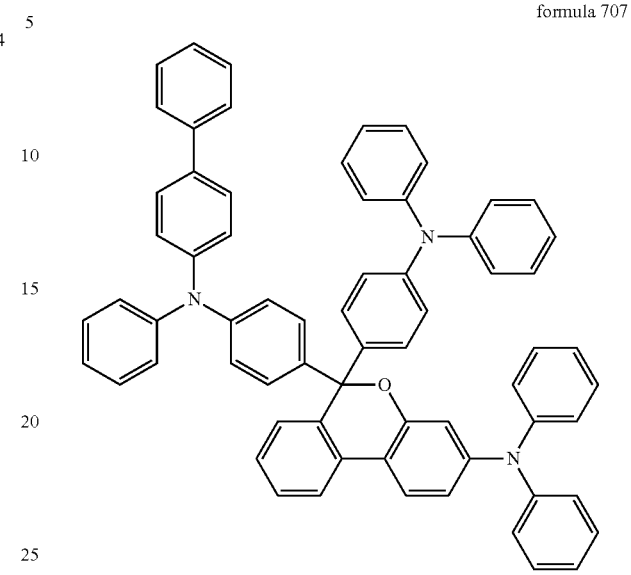
formula 705
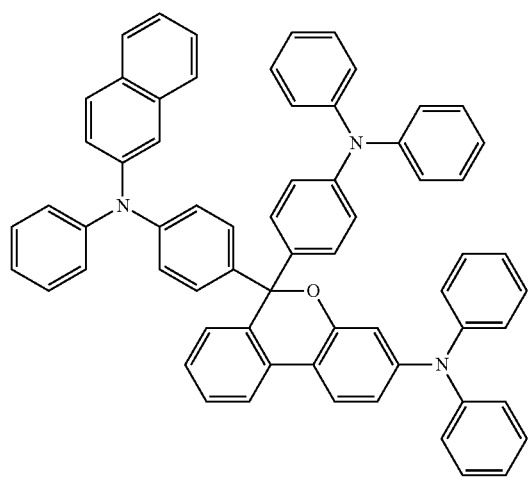
formula 708
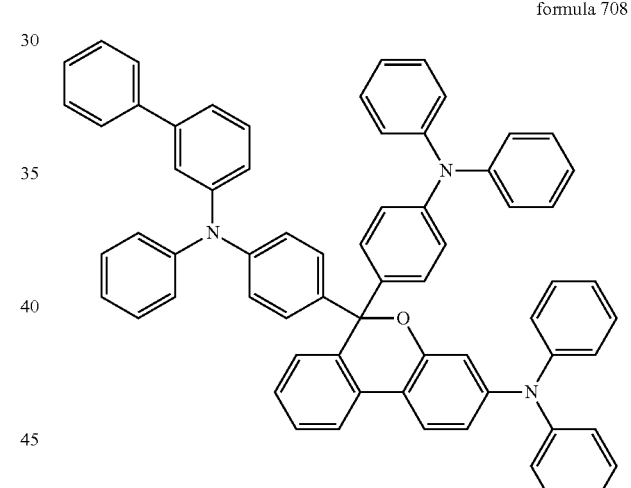
formula 706
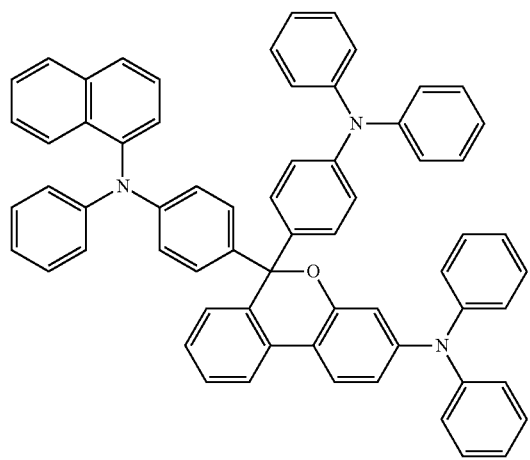
formula 709
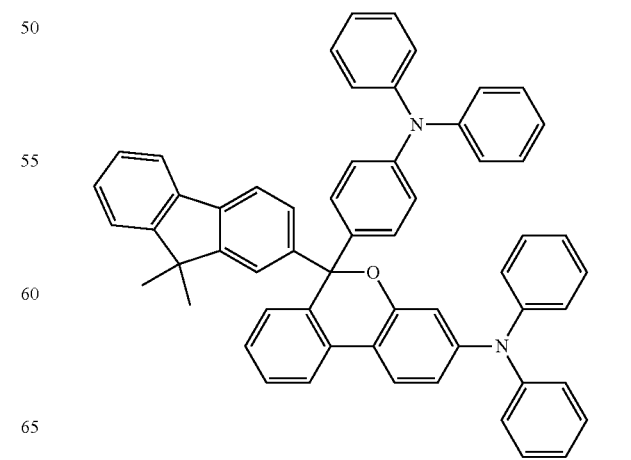

formula 710
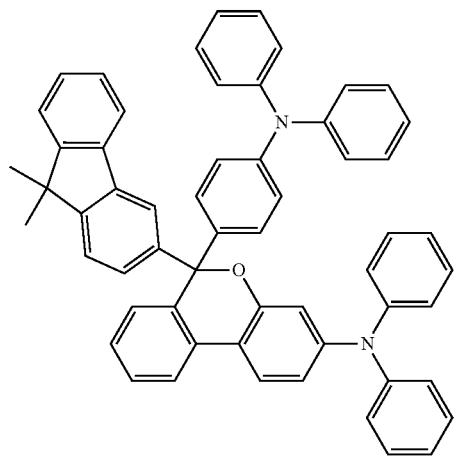
formula 711
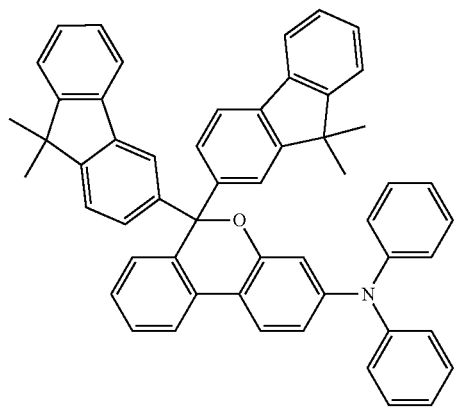
formula 712
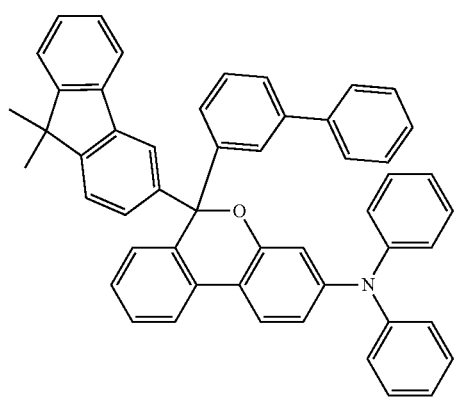
formula 713
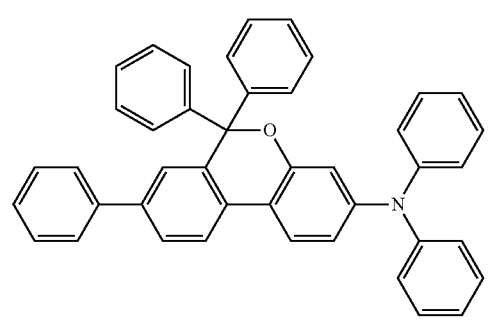
formula 714
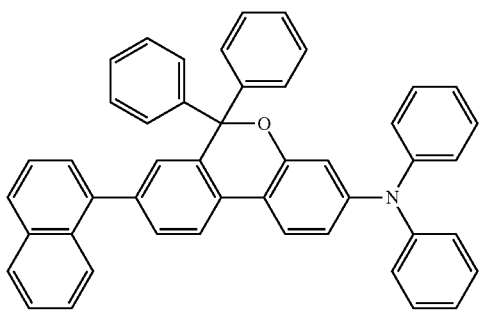
formula 715
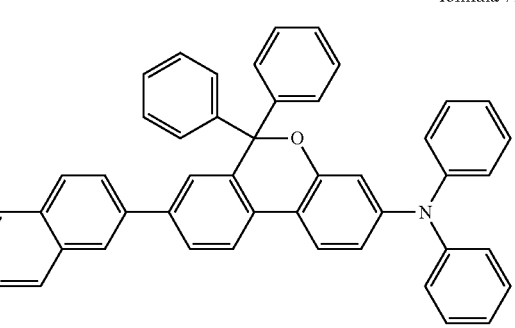
formula 716
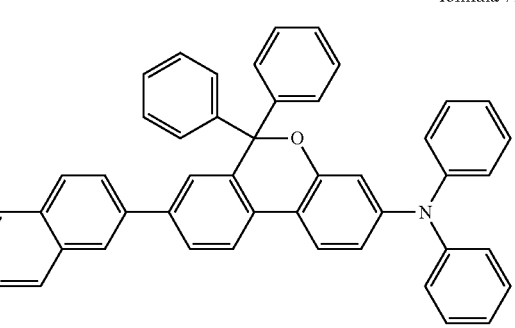
formula 717
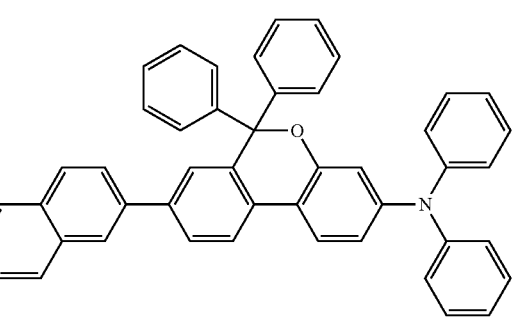

formula 718
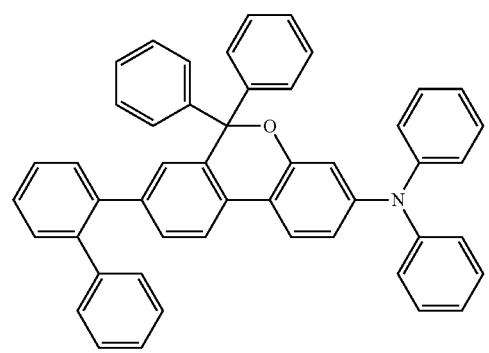
formula 719
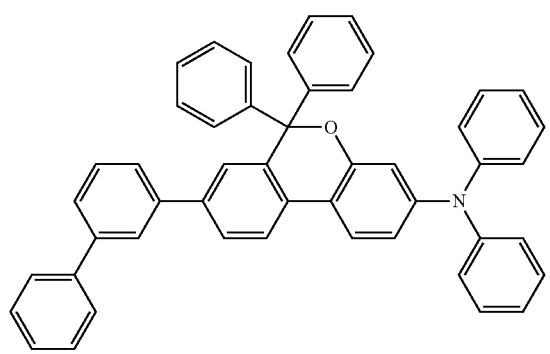
formula 720
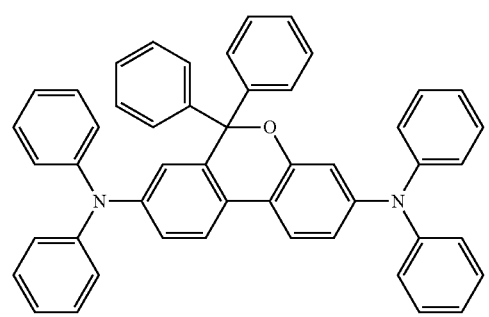
formula 721
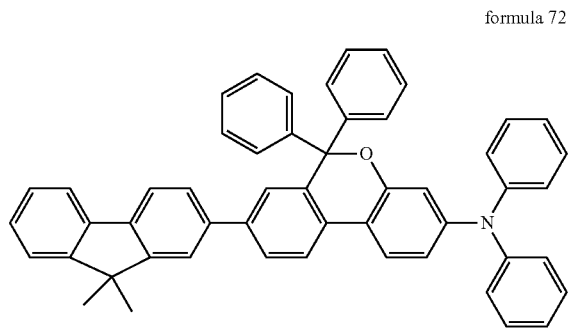
formula 722
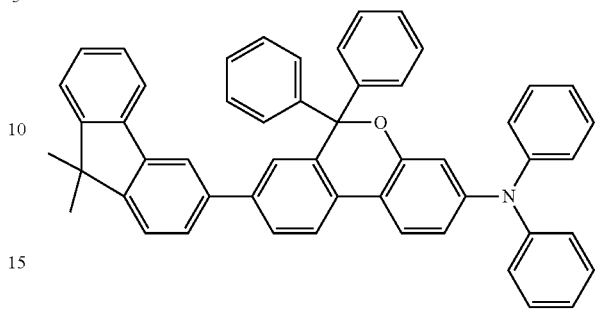
Furthermore, the oxygen heterocyclic compound has a structure as represented by any of following formula 801 to formula 819:
formula 801
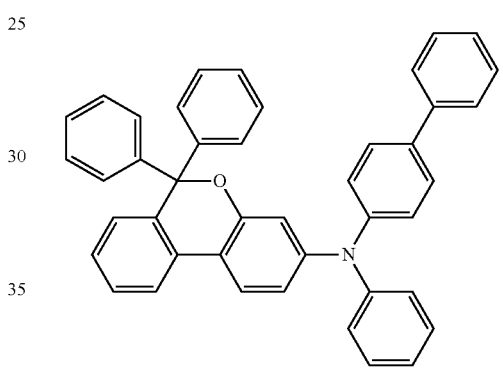
formula 802
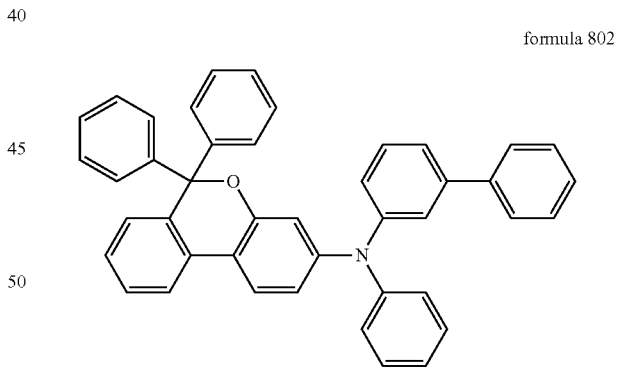
formula 803
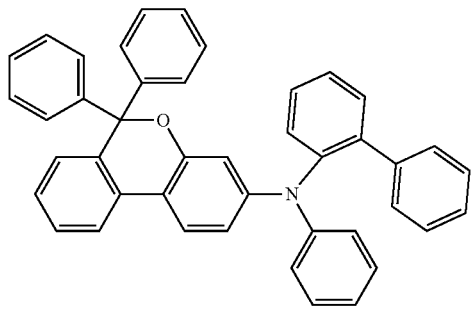

-continued
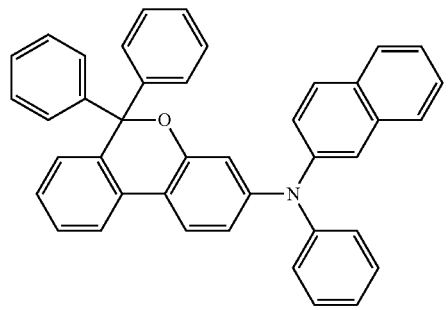
formula 804
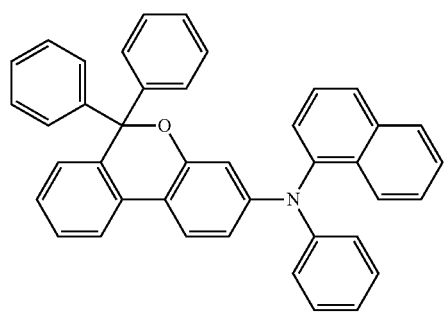
formula 805
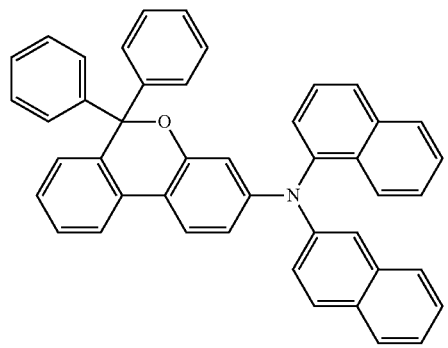
formula 806
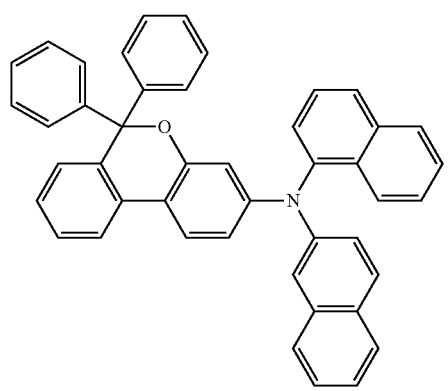
formula 807
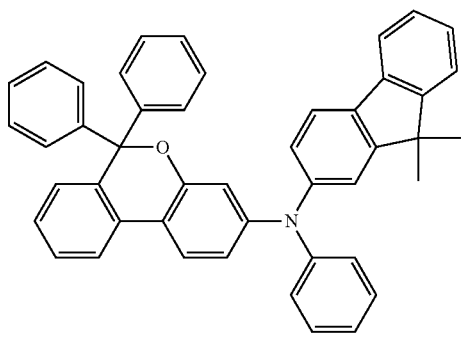
formula 808
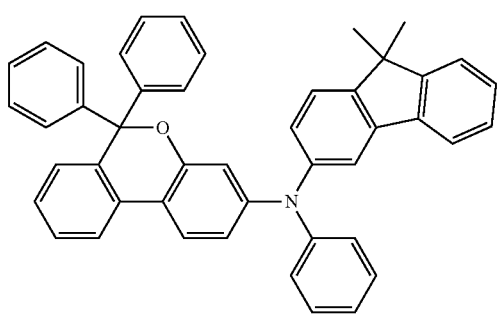
formula 809
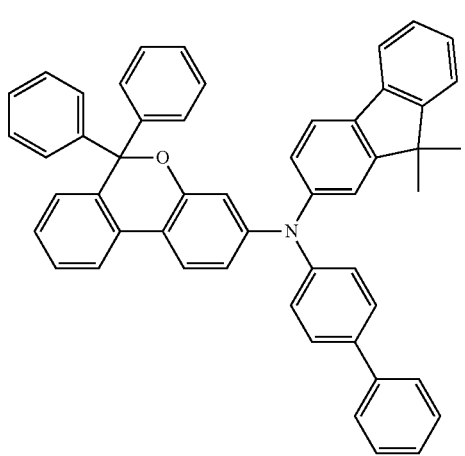
formula 810
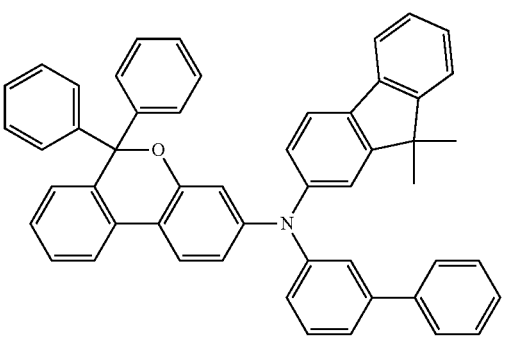
formula 811 formula 812
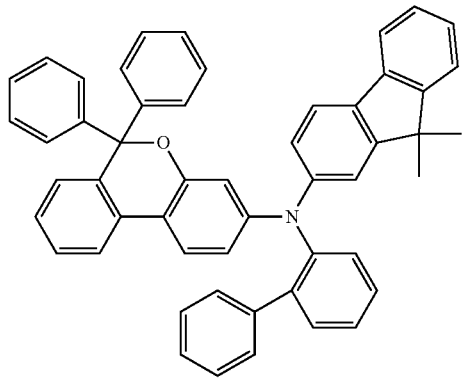
formula 813
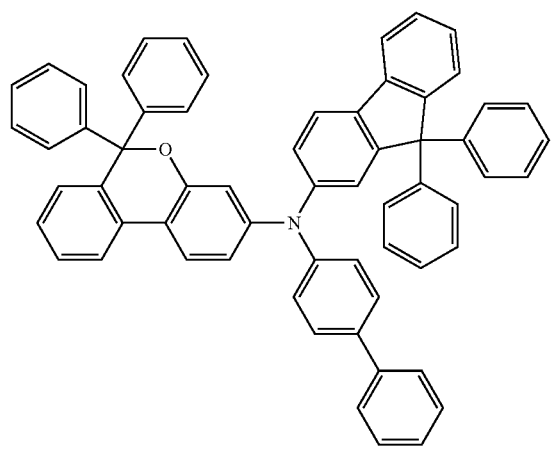
formula 814
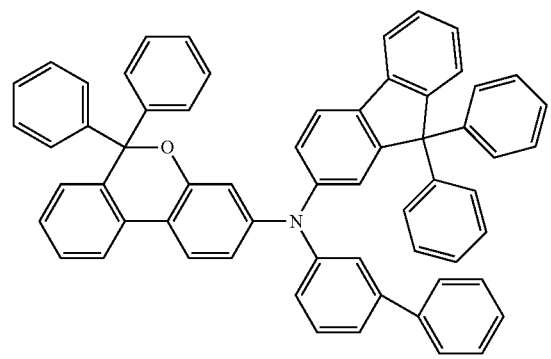
formula 815
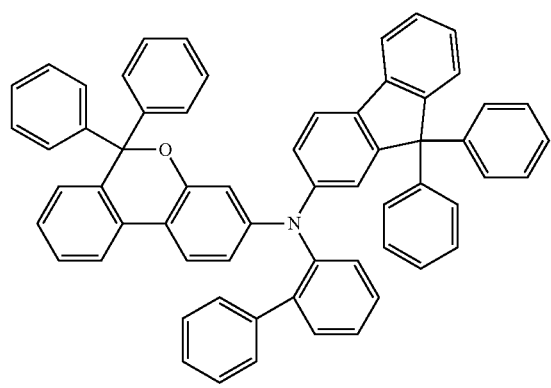
formula 816
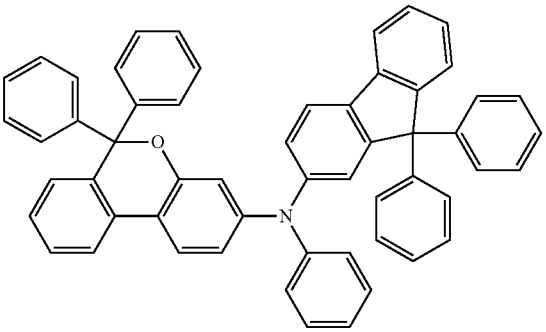
formula 817
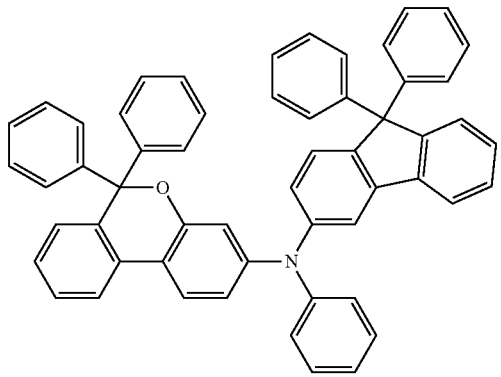
formula 818
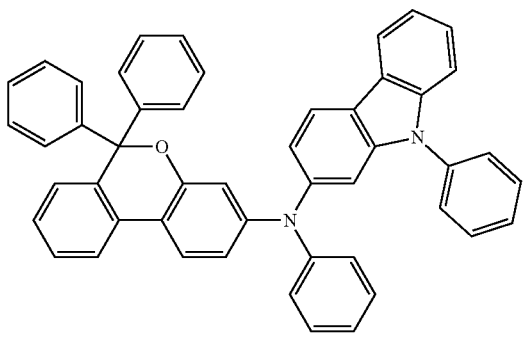
formula 819
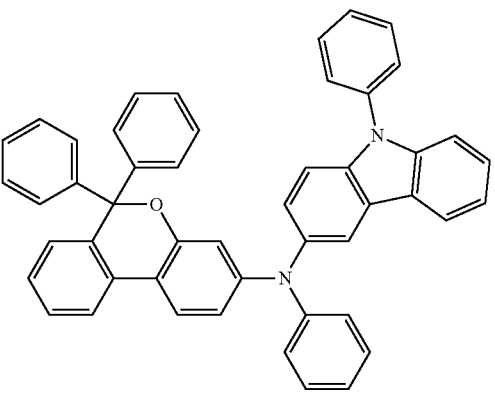
To achieve above objects, another aspect of the present disclosure discloses an application of abovementioned oxygen heterocyclic compound as being an electroluminescent organic material in an electronic device.

To achieve above objects, a further aspect of the present disclosure discloses an electronic device comprising a base, an anode, a cathode, and one or more of organic material layers disposed between the anode and the cathode, wherein at least one of the organic layers comprises the abovementioned oxygen heterocyclic compound.

Beneficial Effect

In an oxygen heterocyclic compound, an application thereof, and an electronic device using the same according to embodiments of the present disclosure, the oxygen heterocyclic compound includes an aromatic amine portion and an oxygen heterocyclic portion, wherein the aromatic amine portion may effectively promote the hole injection and transport performance of the organic material, so as to improve the balance between holes and electrons in the organic light-emitting diode to achieve low voltages and high efficiencies. In addition, the oxygen heterocyclic portion is conducive to the formation of molten evaporation materials, which is conducive to the stability of mass production evaporation. This type of material can achieve high-efficiency electroluminescent device preparation, which can be used in the manufacture of display devices.

DETAILED DESCRIPTION OF PREFERRED EMBODIMENTS

An oxygen heterocyclic compound and an electronic device using the same provided by embodiments of the present disclosure will be explained and described in detail below.

An oxygen heterocyclic compound according to one embodiment of the present disclosure has a structural formula as represented by following formula 1:

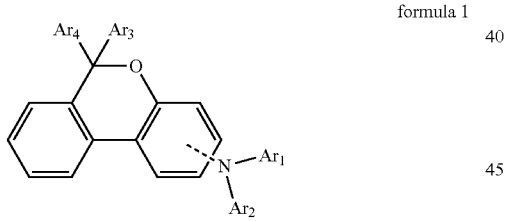

formula 1

In formula 1, $Ar_1$ and $Ar_2$ are independently selected from the group consisting of single or multiple substituted or unsubstituted aryl groups, and single or multiple substituted or unsubstituted heteroaryl groups; or $Ar_1$ and $Ar_2$ together form single or fused aromatic or heterocyclic ring when $Ar_1$ and $Ar_2$ are adjacent aryl groups or heteroaryl groups connected to each other, wherein heteroatoms of the heteroaryl groups are O, N, F, S, or Si; and $Ar_3$ and $Ar_4$ are independently selected from the group consisting of C1 to C22 alkyl groups, $C_1$ to C22 alkoxy groups, C1 to C22 heteroalkyl groups, single or multiple substituted or unsubstituted aryl groups, and substituted or unsubstituted heteroaryl groups, or $Ar_3$ and $Ar_4$ together form a single or fused aromatic or heterocyclic ring when $Ar_3$ and $Ar_4$ are adjacent aryl groups or heteroaryl groups connected to each other, wherein heteroatoms of the heteroaryl groups are O, N, F, S, or Si.

As being a preferred embodiment of the present disclosure, the oxygen heterocyclic compound may have a structural formula represented by following formula 2:

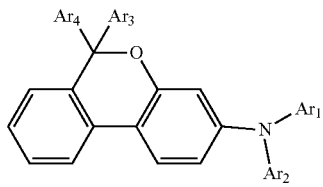

formula 2

It can be understood that the aromatic amine portion of the oxygen heterocyclic compound in the preferred embodiment has a fixed substitution position.

As being a preferred embodiment of the present disclosure, $Ar_1$ and $Ar_2$ may be independently represented by any of following formula 301 to formula 332:

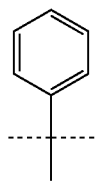

formula 301

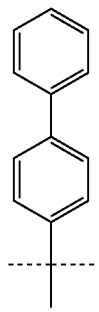

formula 302

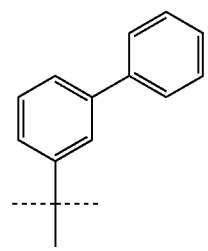

formula 303

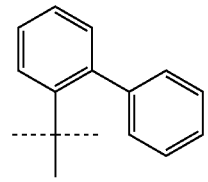

formula 304

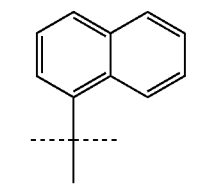

formula 305

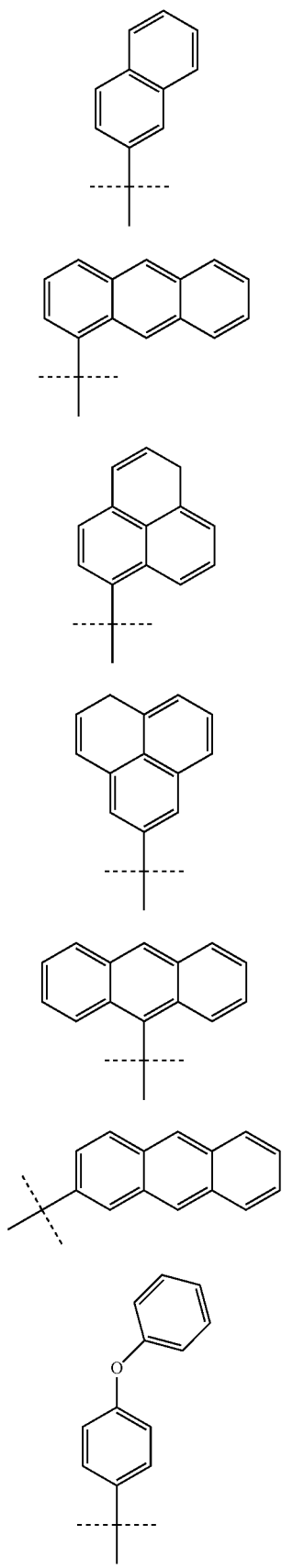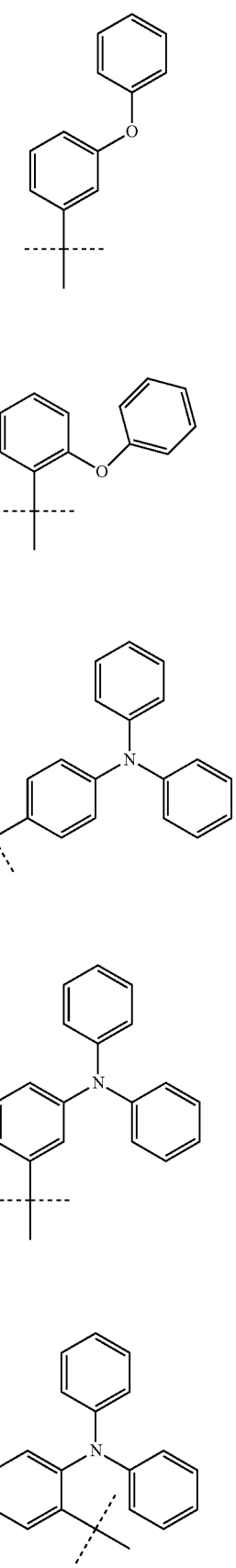

formula 318
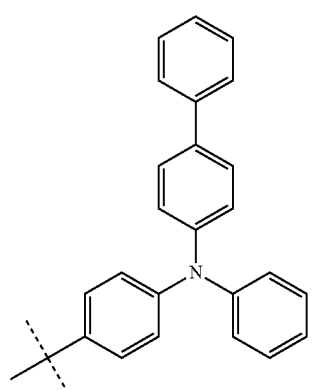
formula 319
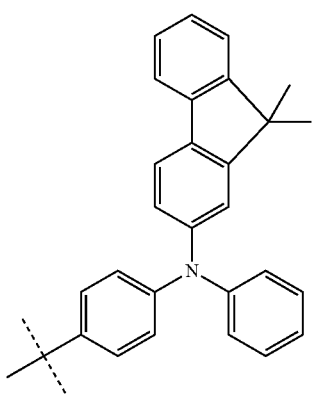
formula 320
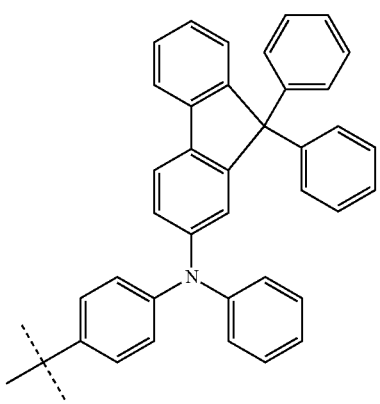
formula 321
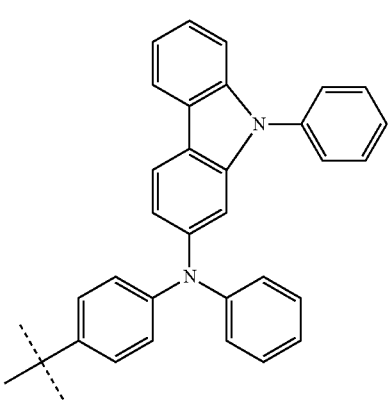
formula 322
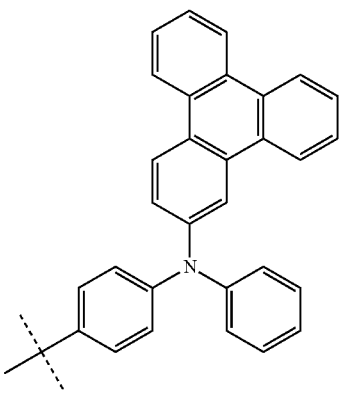
formula 323
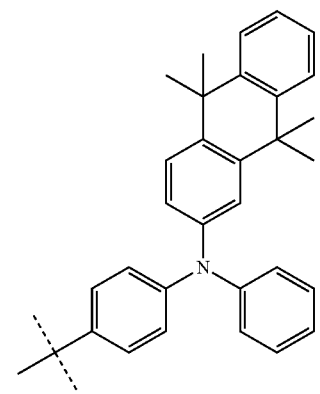
formula 324
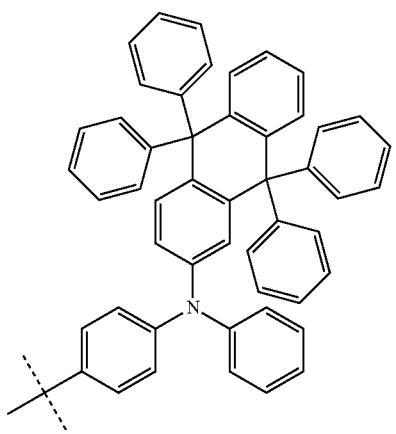
formula 325
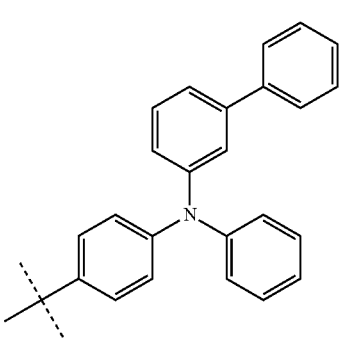

formula 326
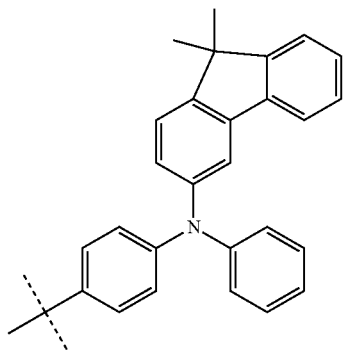
formula 327
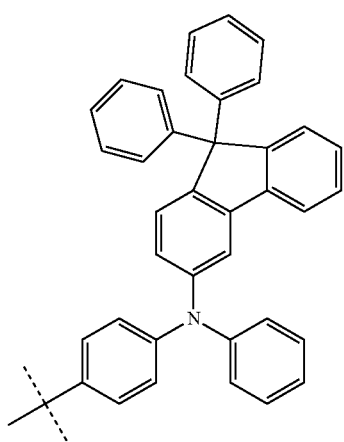
formula 328
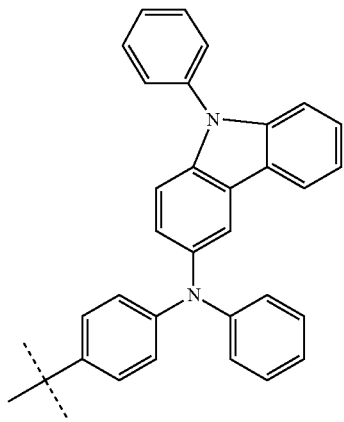
formula 329
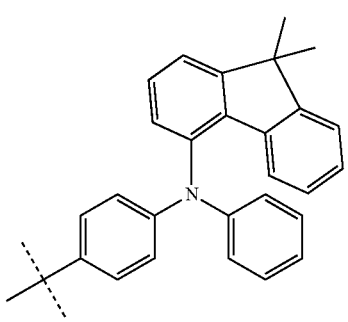
formula 330
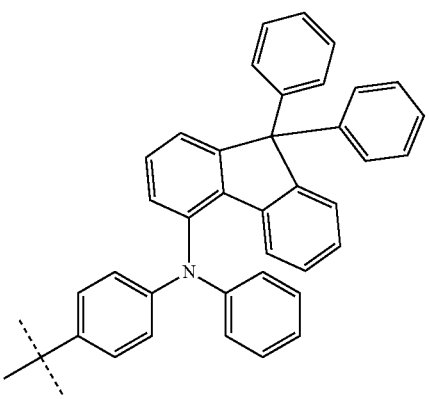
formula 331
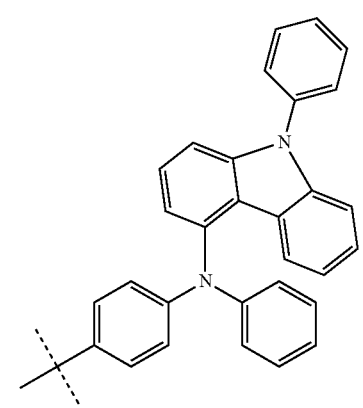
formula 332
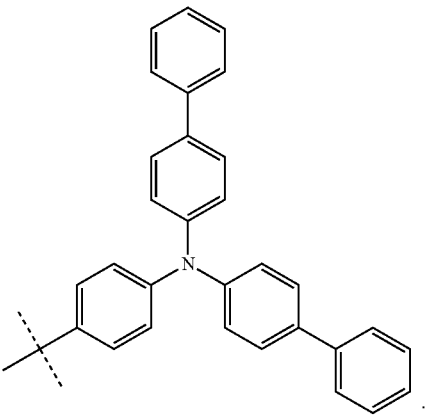
As being a preferred embodiment of the present disclosure, Ar$_1$ and Ar$_4$ are independently represented by any of above formula 301 to formula 332 and following formula 401 to formula 403:
formula 401
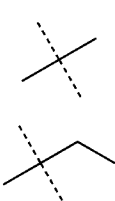
formula 402
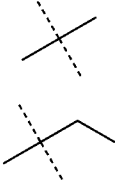

formula 403
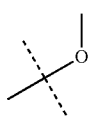
As being a further preferred embodiment of the present disclosure, the oxygen heterocyclic compound may have a structural formula represented by any of following formula 501 to formula 508:
formula 501
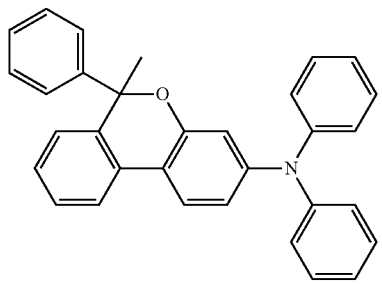
formula 502
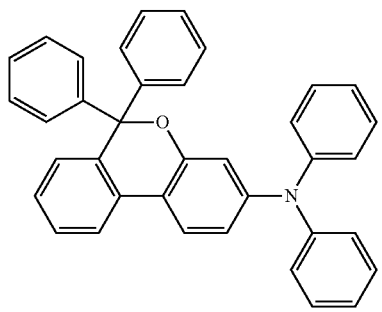
formula 503
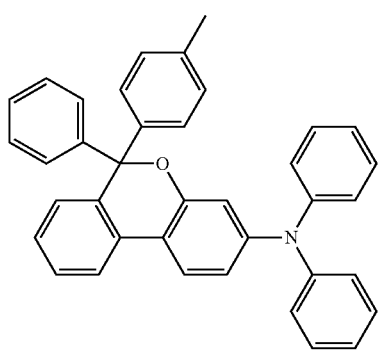
formula 504
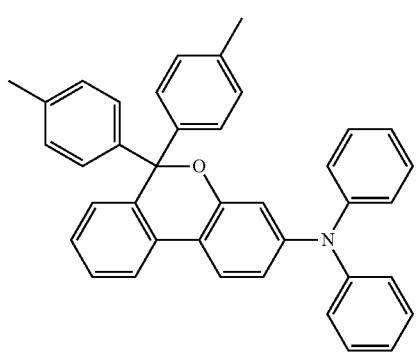
formula 505
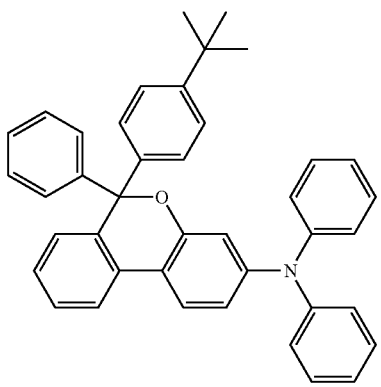
formula 506
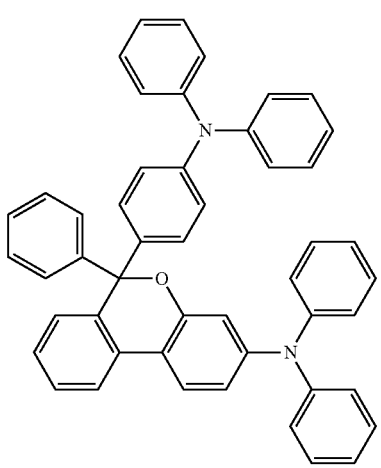
formula 507
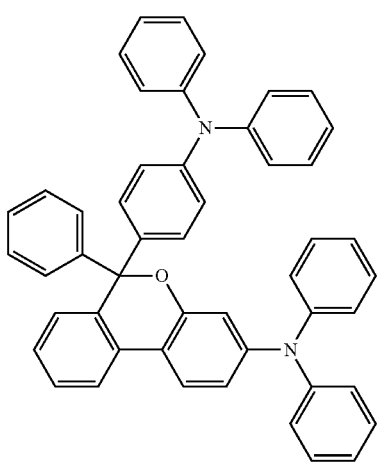

formula 508
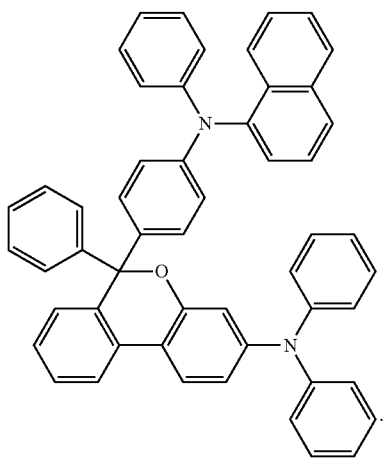
As being another further preferred embodiment of the present disclosure, the oxygen heterocyclic compound may have a structure as represented by any of following formula 601 to formula 617:
formula 601
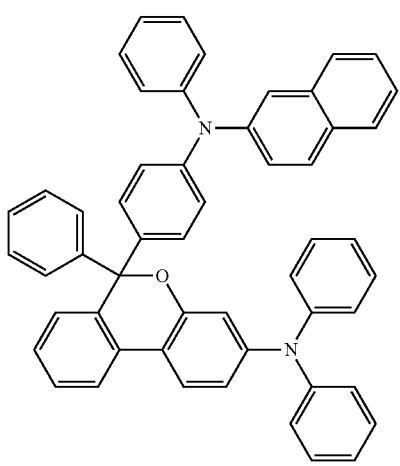
formula 602
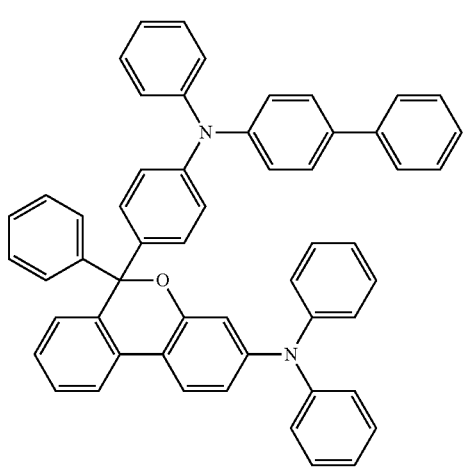
formula 603
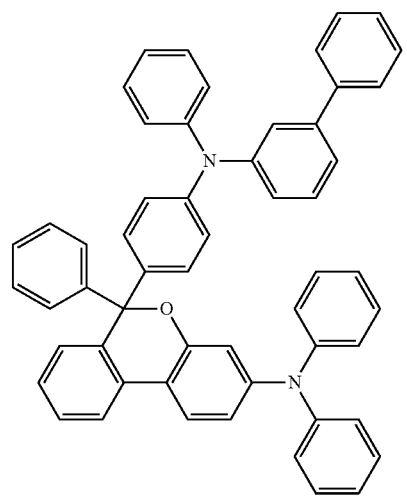
formula 604
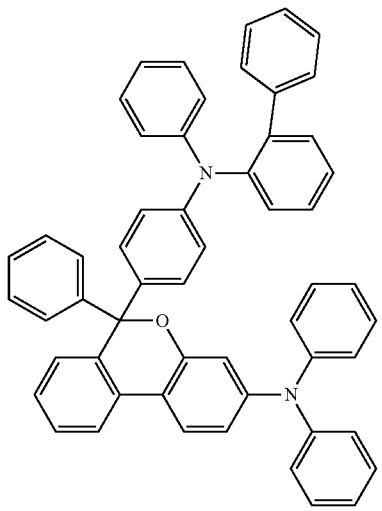
formula 605
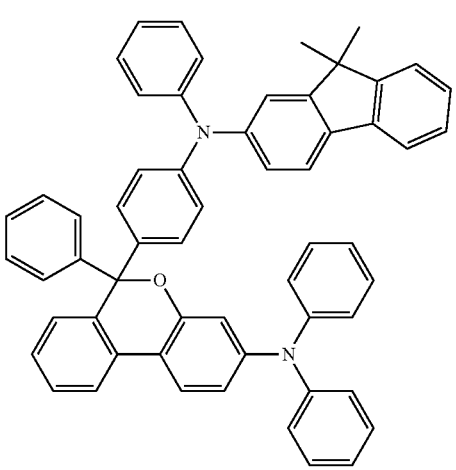

formula 606
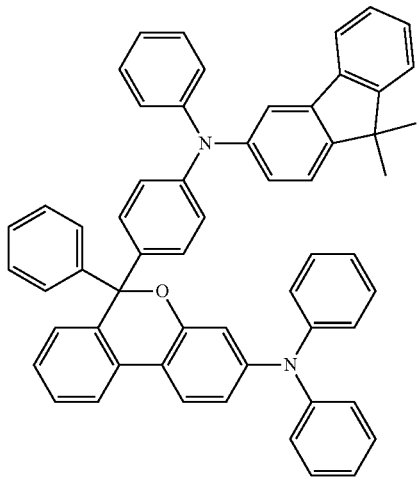
formula 607
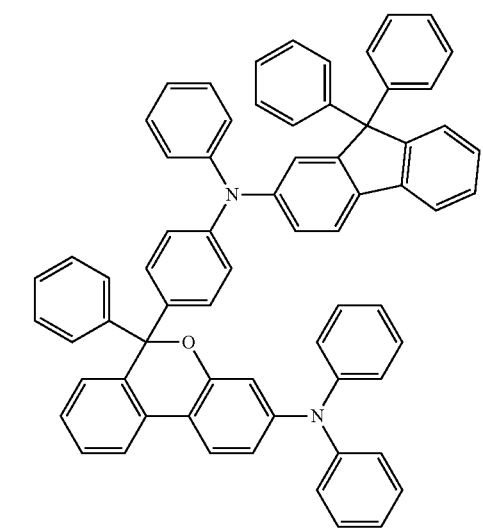
formula 608
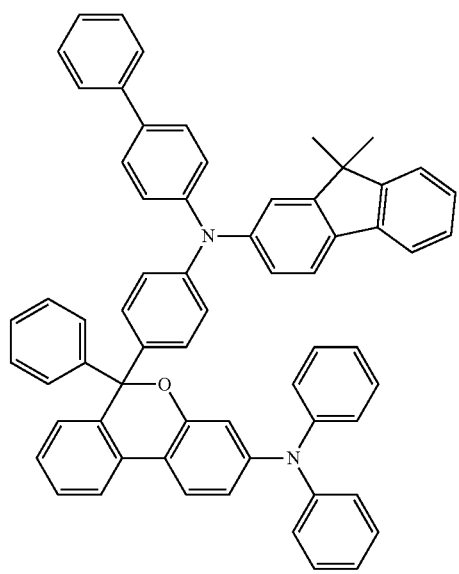
formula 609
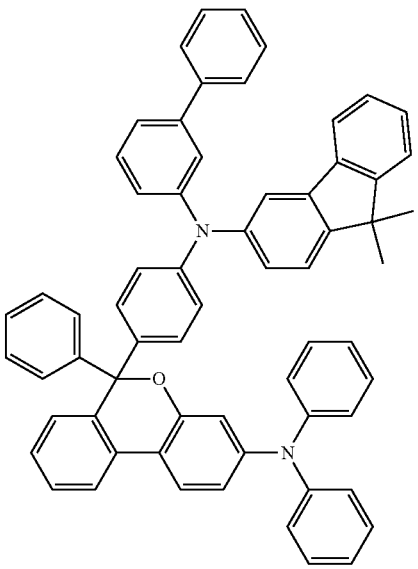
formula 610
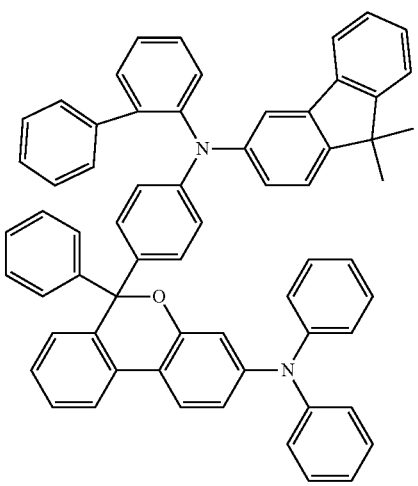
formula 611
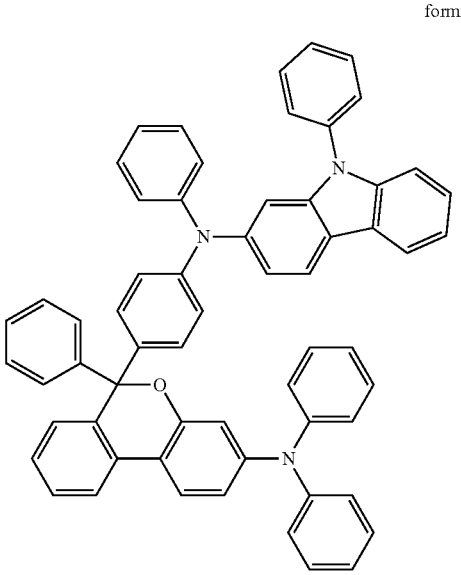

formula 612
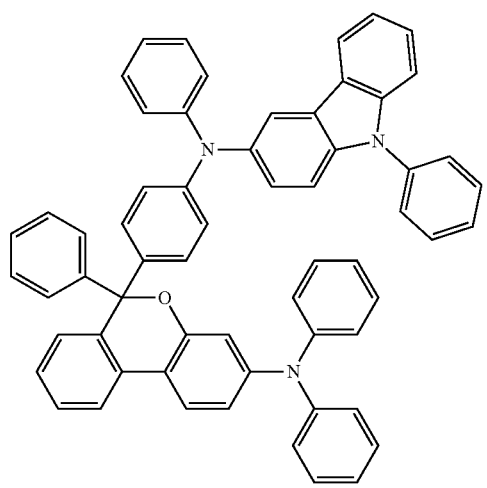
formula 613
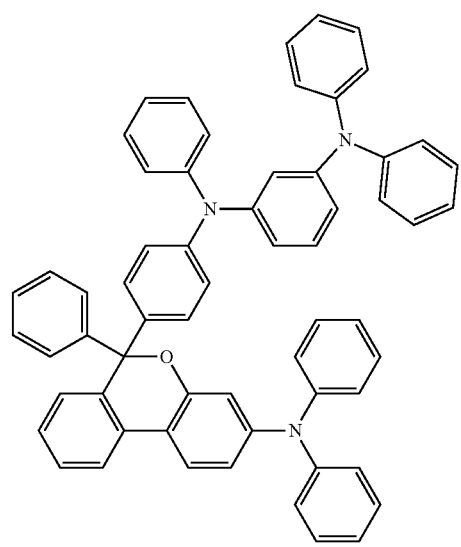
formula 614
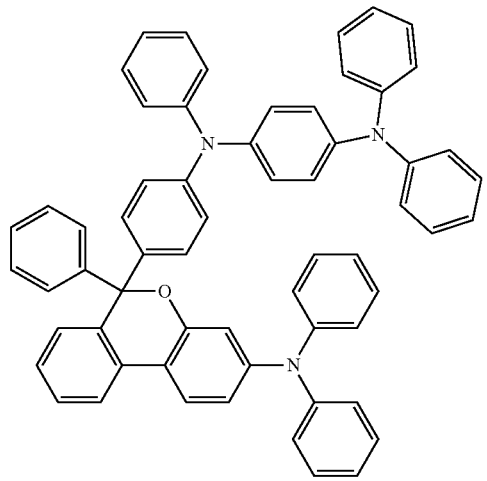
formula 615
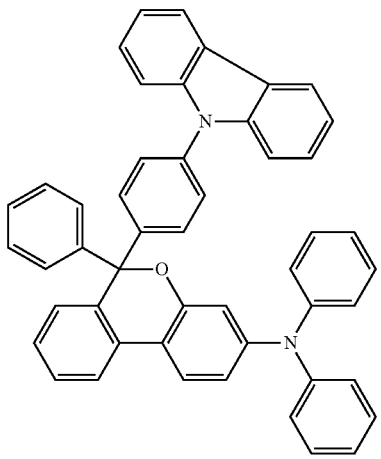
formula 616
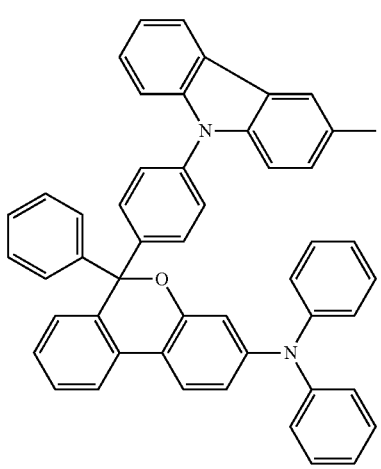
formula 617
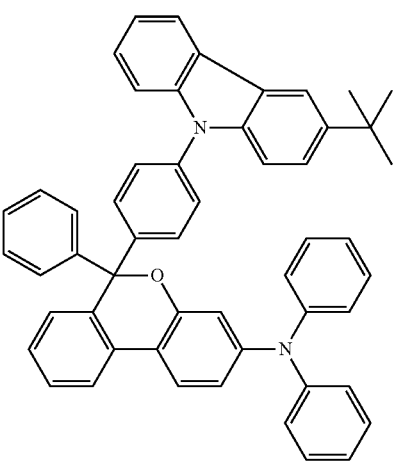
As being another further preferred embodiment of the present disclosure, the oxygen heterocyclic compound may have a structure as represented by any of following formula 701 to formula 722:

formula 701
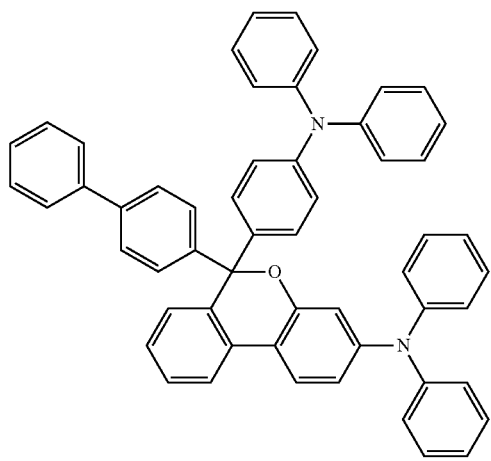
formula 702
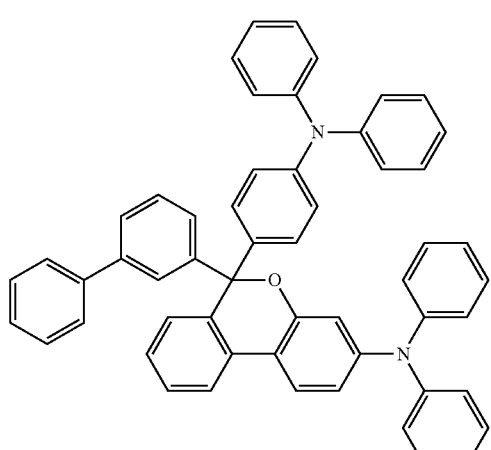
formula 703
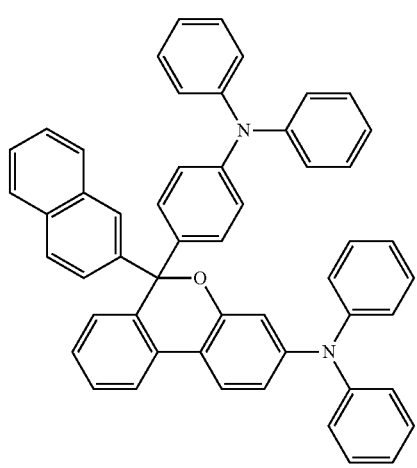
formula 704
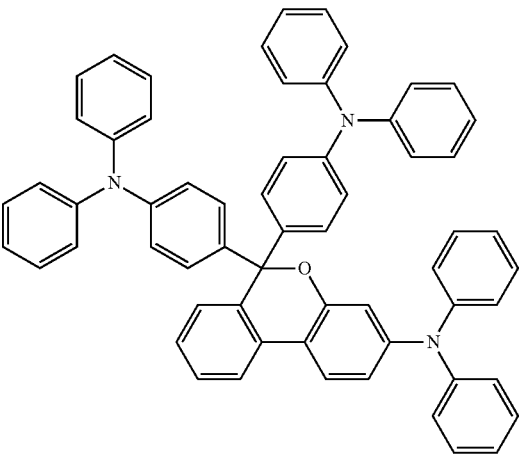
formula 705
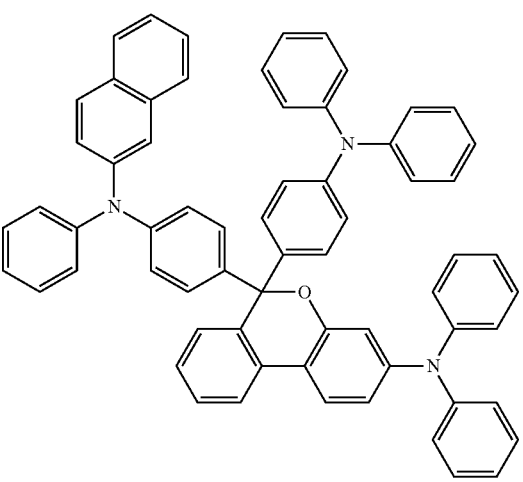
formula 706
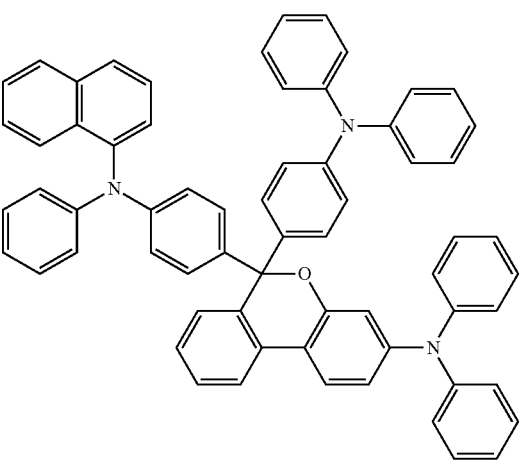

formula 707
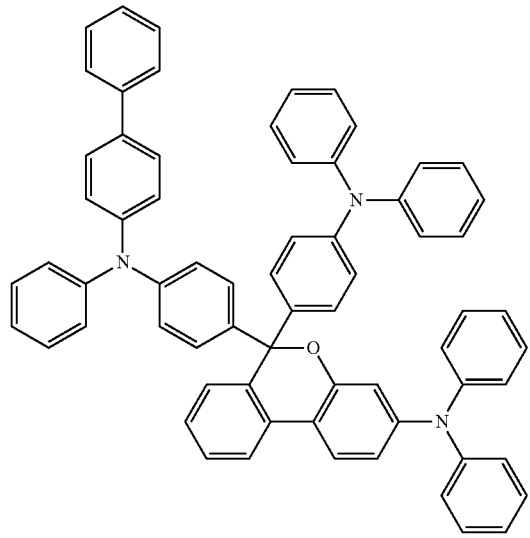
formula 708
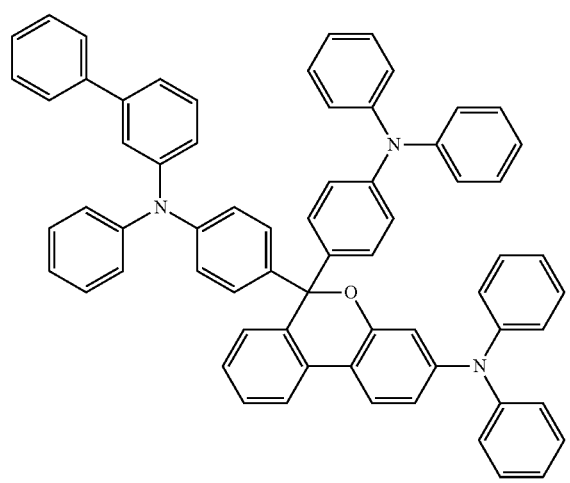
formula 709
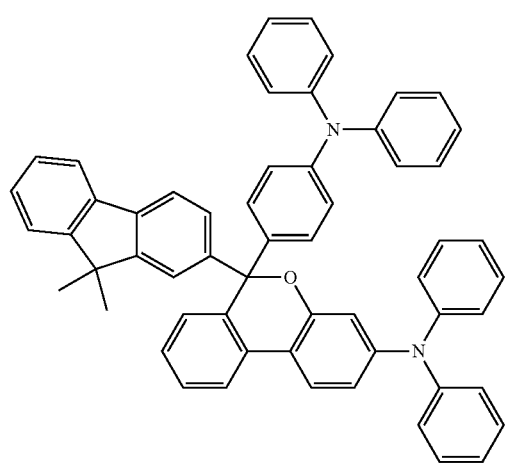
formula 710
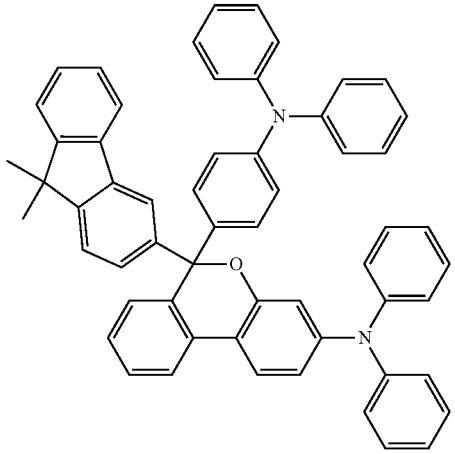
formula 711
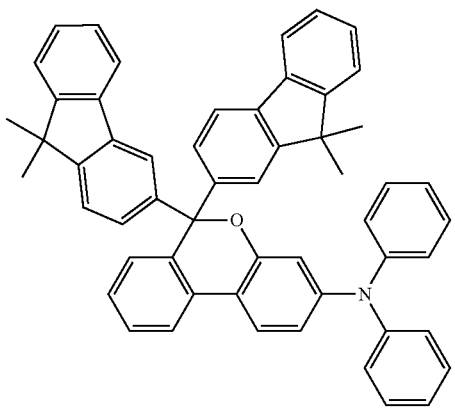
formula 712
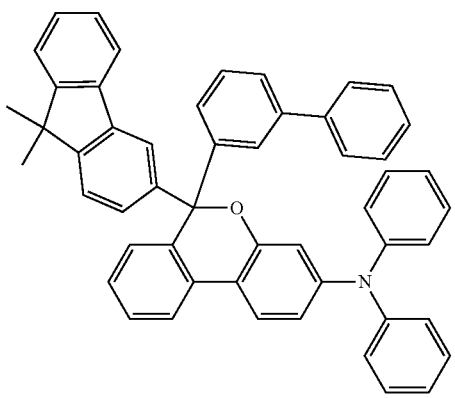
formula 713
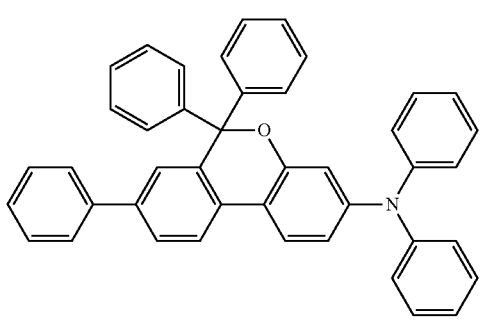

formula 714
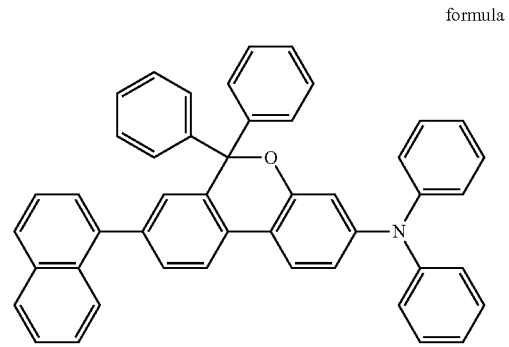
formula 718
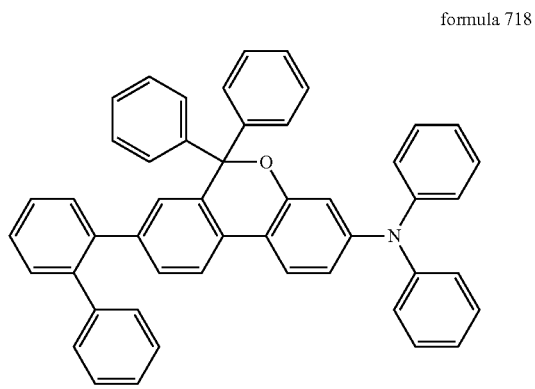
formula 715
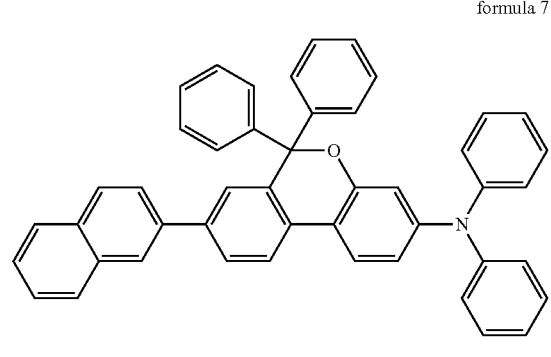
formula 719
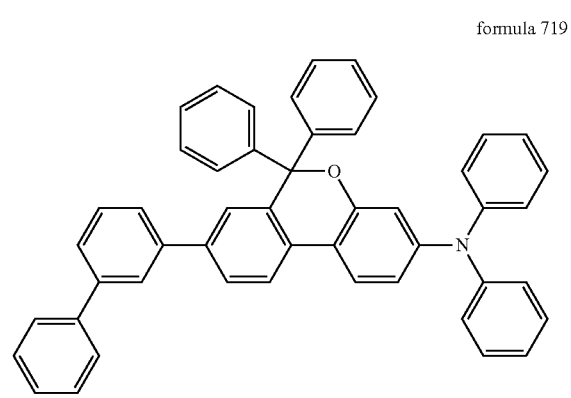
formula 716
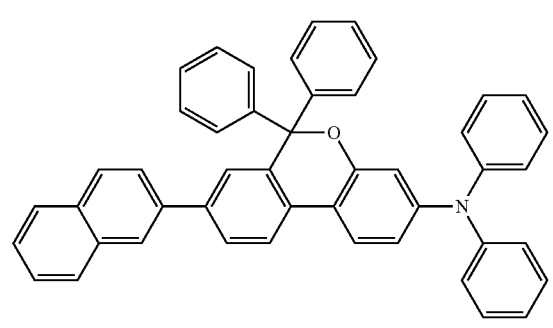
formula 720
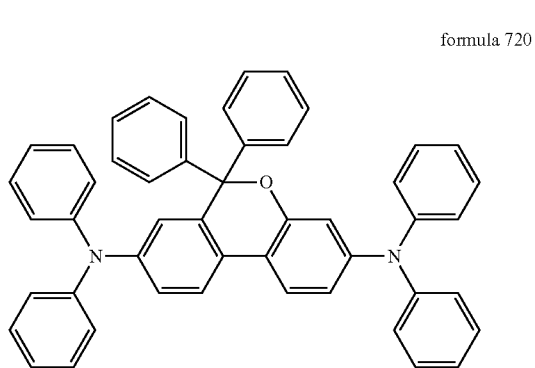
formula 717
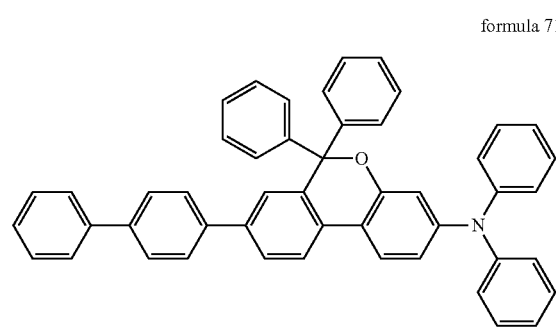
formula 721
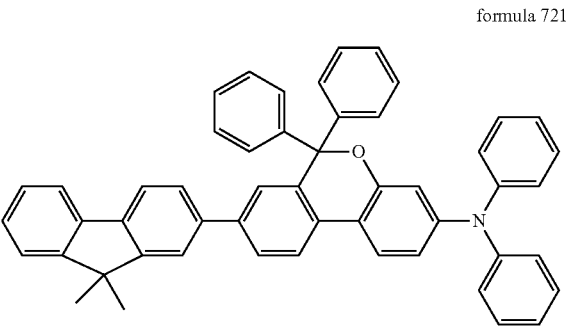

formula 722
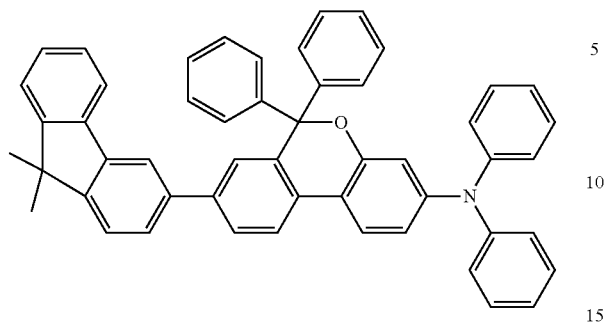
formula 804
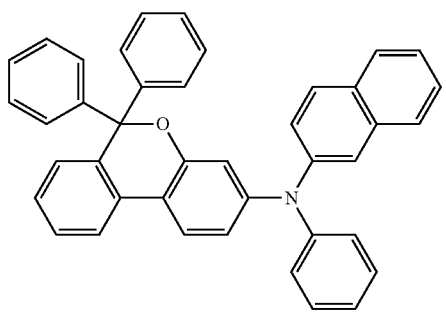
As being another further preferred embodiment of the present disclosure, the oxygen heterocyclic compound may have a structure as represented by any of following formula 801 to formula 819:
formula 801
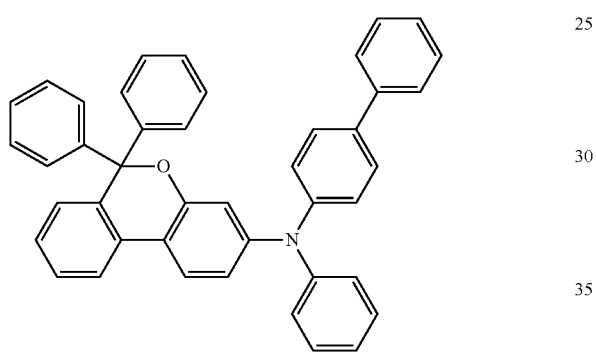
formula 805
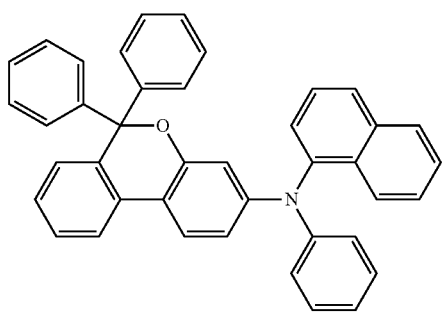
formula 802
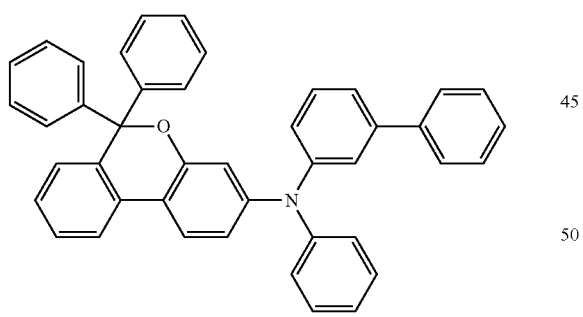
formula 806
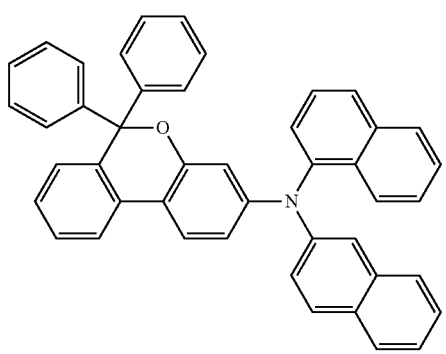
formula 803
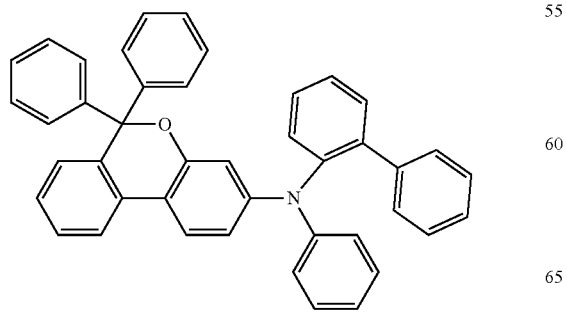
formula 807
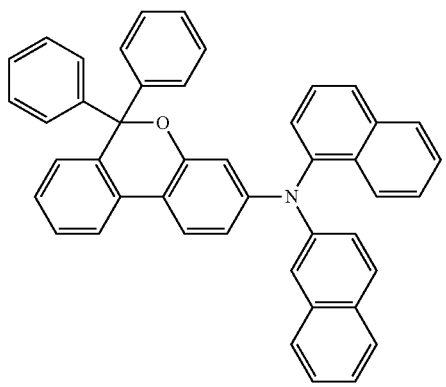

formula 808
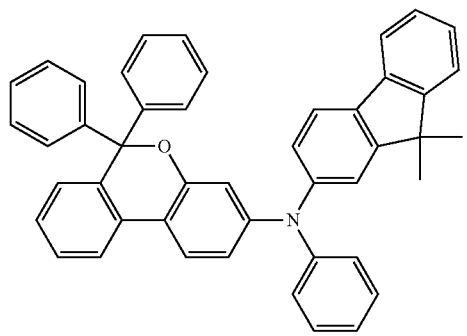
formula 809
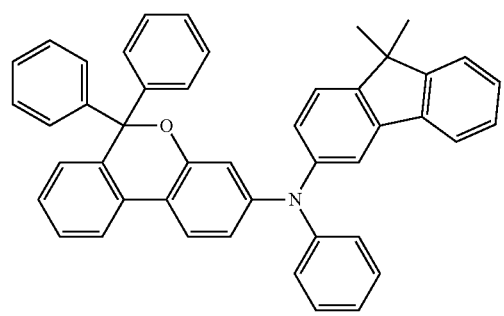
formula 810
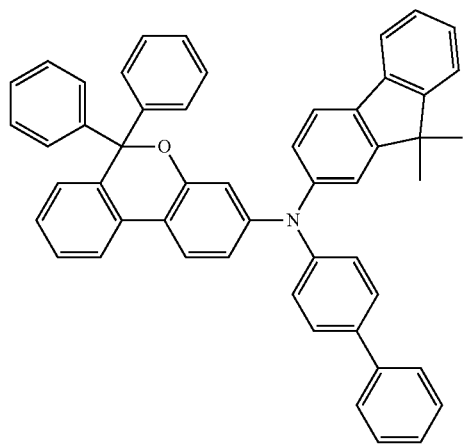
formula 811
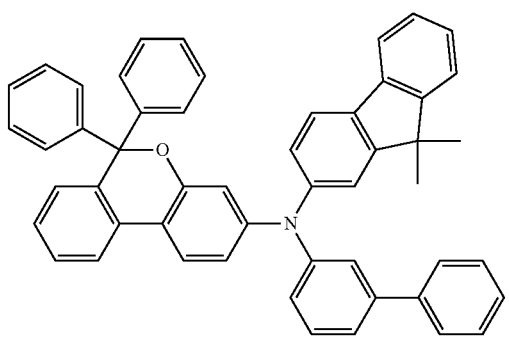
formula 812
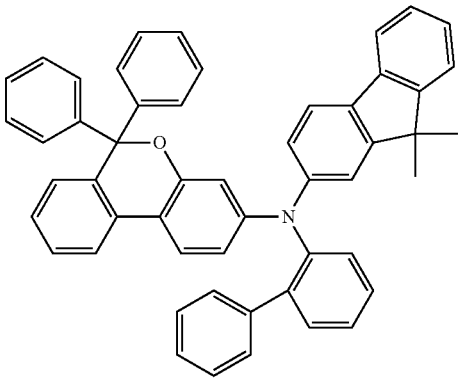
formula 813
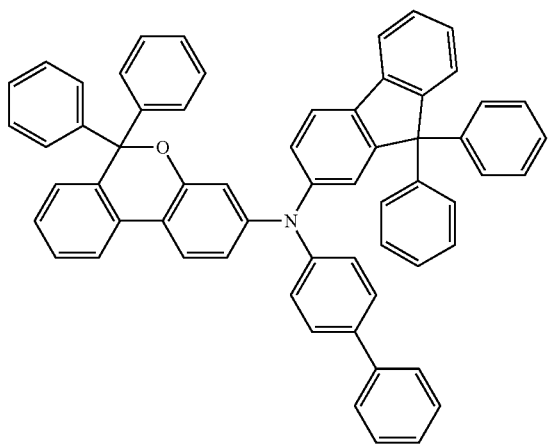
formula 814
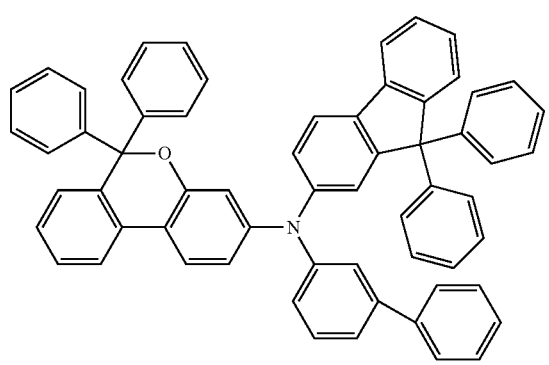
formula 815
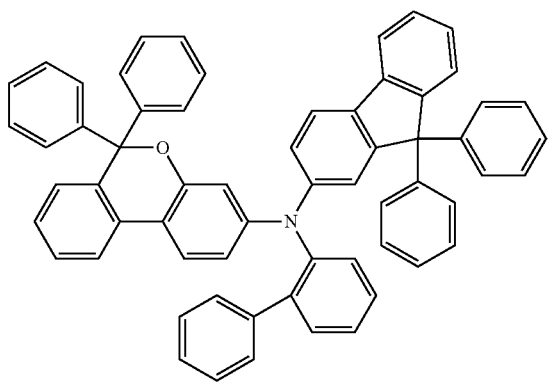

-continued formula 816
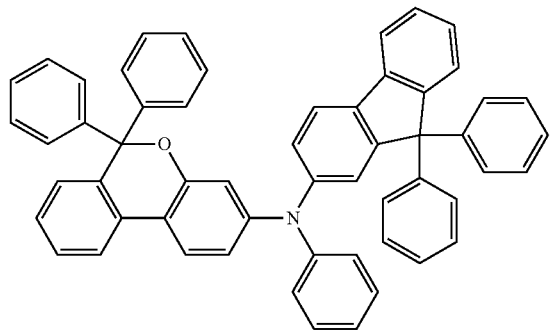

formula 817
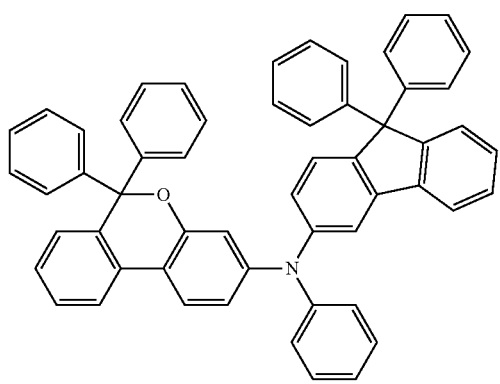

formula 818
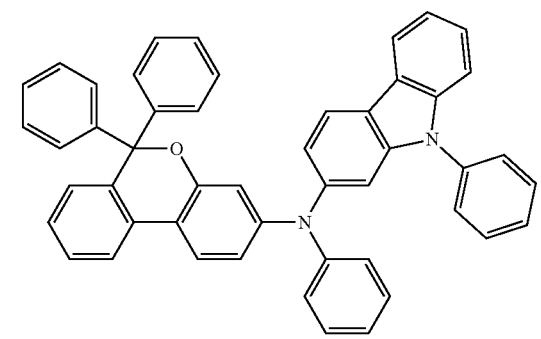

formula 819
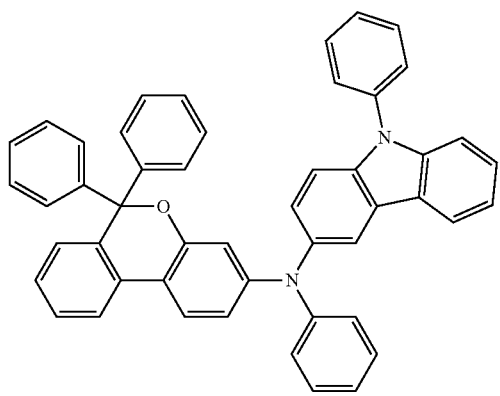

Another embodiment of the present disclosure provides an application of the abovementioned oxygen heterocyclic compound as being an electroluminescent organic material in an electronic device.

A further embodiment of the present disclosure provides an electronic device, comprising a base, an anode, a cathode, and one or more of organic material layers disposed between the anode and the cathode, wherein at least one of the organic layers comprises the oxygen heterocyclic compound oxygen heterocyclic compound according to the above embodiment. It is characterized that the organic layers may include a hole injection layer, a hole transport layer, an electron injection layer, an electron transport layer, and a light-emitting layer. Herein, the electronic device may be an electroluminescent device, for example, an organic light-emitting diode device.

In the following, the preparation methods of the oxygen heterocyclic compounds provided in the above embodiments of the present disclosure are described.

Embodiment 1

The synthesis of Target structure 1 of the oxygen heterocyclic compound is shown in process formula 9:

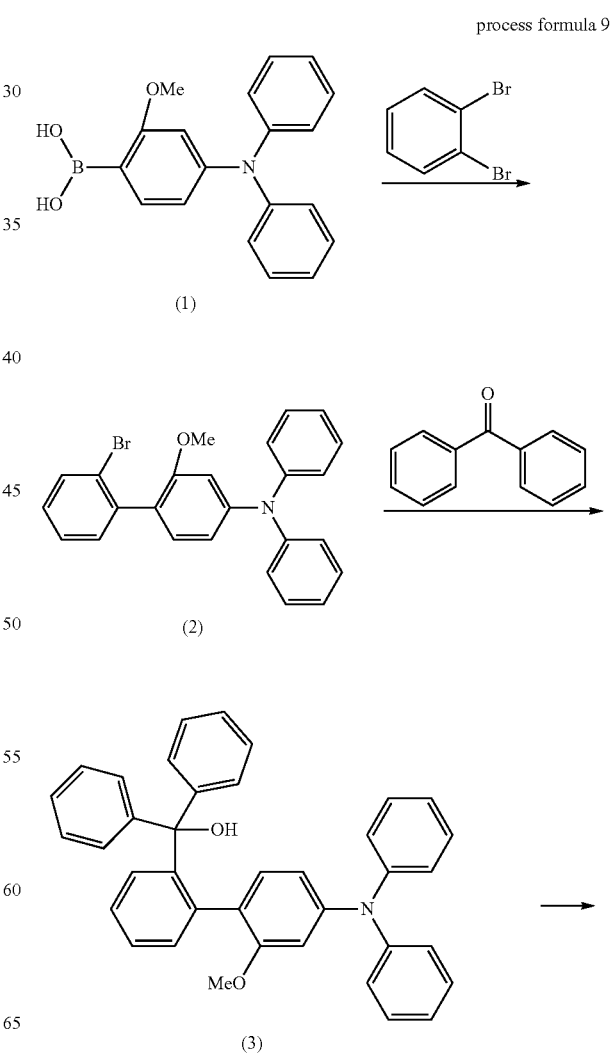

process formula 9

63

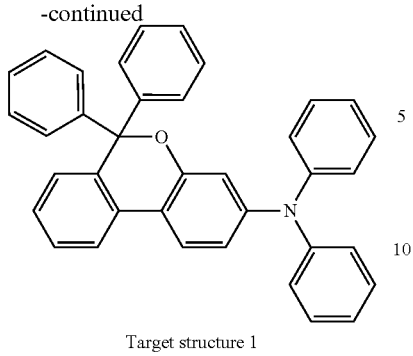

Target structure 1

The preparation method of Target structure 1 of the oxygen heterocyclic compound provided by Embodiment 1 is as follows:

Compound (1) (3 mmol), Pd(OAc)$_2$ (0.15 mmol), PPh$_3$ (0.3 mmol), CsCO$_3$ (6.0 mmol), and 50 mL of toluene were added to a 100 mL two-necked flask, then stirred and heated to 100° C. under argon atmosphere to react for 12 h. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 2.7 mmol of an intermediate compound (2) was obtained by using 200-300 meshes silica gel as a stationary phase and dichloromethane as an eluent, and the yield is 90%.

The product of the previous step-compound (2), magnesium (Mg, 3 mmol), and one grain of I2 were added into a 250 mL two-necked flask, and then 10 mL of THF solvent was added for water and oxygen removal under argon atmosphere; the mixture was stirred until the iodine fades, and reacts for 0.5 hours. Next, Benzophenone (3 mmol) was dissolved in 50 mL of THF solvent for removing water and oxygen, and then the mixed solution was introduced into the mixed solution prepared in the previous step under argon, and reacts for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.9 mmol of an intermediate compound (3) was obtained by using 200-300 meshes silica gel as a stationary phase and dichloromethane as an eluent, and the yield is 70%.

The obtained intermediate compound (3) was added into 100 mL of acetonitrile, and 2 mmol of boron tribromide was added to the mixture, and stirred for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.3 mmol of Target structure 1 was obtained by using 200-300 meshes silica gel as a stationary phase and dichloromethane as an eluent, and the yield is 77%. Matrix-assisted laser desorption ionization time-of-flight mass spectrometer (MALDI-TOF): Calculated value m/z, 501.63; Measured value m/z, 501.42. Elemental analysis (EA): Calculated value C, 88.59; H, 5.43; N, 2.79; Measured value C, 88.25; H, 5.51; N, 2.83.

64

Embodiment 2

The synthesis of Target structure 2 of the oxygen heterocyclic compound is shown in process formula 10:

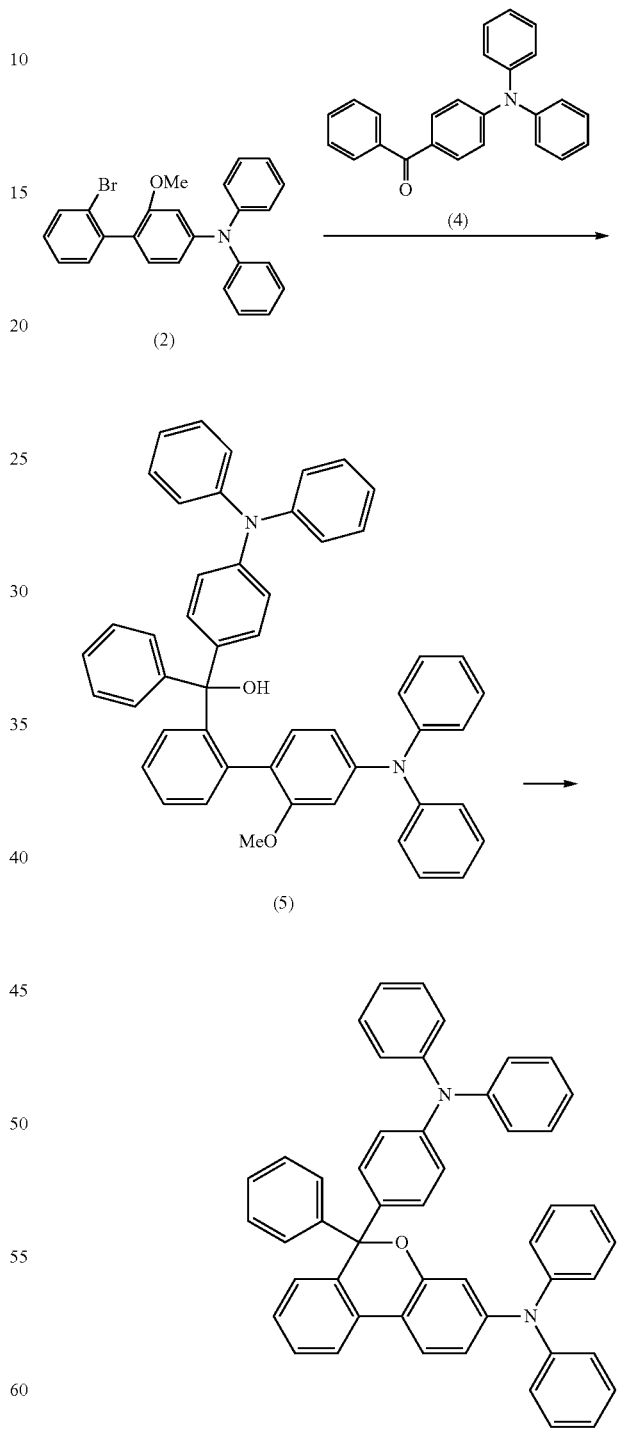

process formula 10

In Embodiment 2, the step of producing the previous product-compound (2) can be similar to the step of producing the previous product-compound (2) in Embodiment 1.

The preparation method of Target structure 2 of the oxygen heterocyclic compound provided by Embodiment 2 is as follows:

The product of the previous step-compound (2) (3 mmol), magnesium (Mg, 3 mmol), and one grain of 12 were added into a 250 mL two-necked flask, and then 10 mL of THF solvent was added for water and oxygen removal under argon atmosphere; the mixture was stirred until the iodine fades, and reacts for 0.5 hours. Next, compound (4) (3.2 mmol) was dissolved in 50 mL of THF solvent for removing water and oxygen, and then the mixed solution was introduced into the mixed solution prepared in the previous step under argon, and reacts for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 2.0 mmol of an intermediate compound (5) was obtained by using 200-300 meshes silica gel as a stationary phase and dichloromethane as an eluent, and the yield is 67%.

The obtained intermediate compound (5) was added into 100 mL of acetonitrile, and 2.5 mmol of boron tribromide was added to the mixture, and stirred for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.6 mmol of Target structure 2 was obtained by using 200-300 meshes silica gel as a stationary phase and dichloromethane as an eluent, and the yield is 81%. Matrix-assisted laser desorption ionization time-of-flight mass spectrometer (MALDI-TOF): Calculated value m/z, 668.84; Measured value m/z, 668.24. Elemental analysis (EA): Calculated value C, 87.99; H, 5.43; N, 4.19; Measured value C, 87.84; H, 5.26; N, 4.01.

Embodiment 3

The synthesis of Target structure 3 of the oxygen heterocyclic compound is shown in process formula 11:

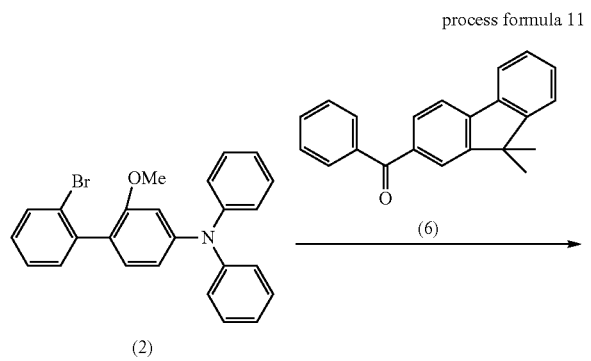

process formula 11

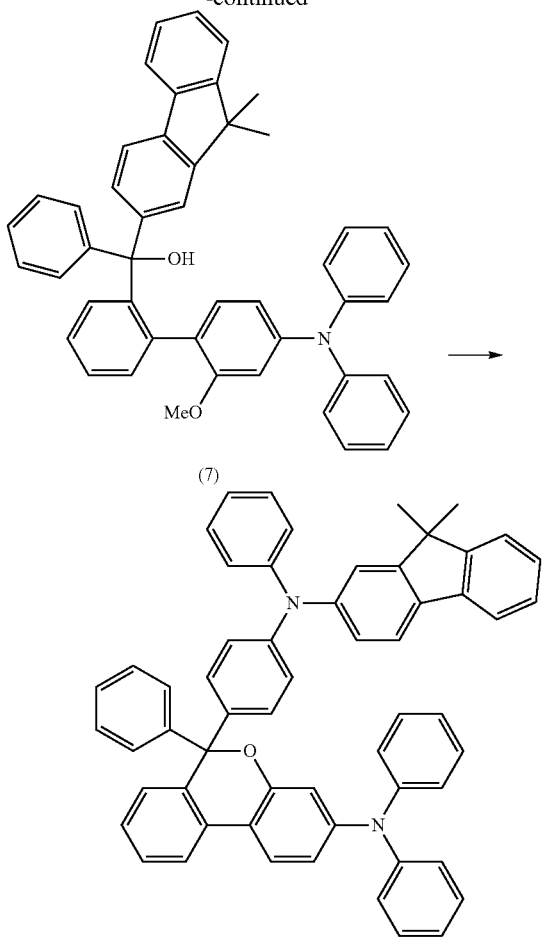

Target structure 3

In Embodiment 3, the step of producing the previous product-compound (2) can be similar to the step of producing the previous product-compound (2) in Embodiment 1. The preparation method of Target structure 3 of the oxygen heterocyclic compound provided by Embodiment 3 is as follows:

The product of the previous step-compound (2) (3 mmol), magnesium (Mg, 3.3 mmol), and one grain of 12 were added into a 250 mL two-necked flask, and then 10 mL of THF solvent was added for water and oxygen removal under argon atmosphere; the mixture was stirred until the iodine fades, and reacts for 0.5 hours. Next, compound (6) (3.2 mmol) was dissolved in 50 mL of THF solvent for removing water and oxygen, and then the mixed solution was introduced into the mixed solution prepared in the previous step under argon, and reacts for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.95 mmol of an intermediate compound (7) was obtained by using 200-300 meshes silica gel as a stationary phase and dichloromethane as an eluent, and the yield is 65%.

The obtained intermediate compound (7) was added into 100 mL of acetonitrile, and 2.5 mmol of boron tribromide was added to the mixture, and stirred for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.7 mmol of Target structure 3 was obtained by using 200-300 meshes silica gel as a stationary phase and dichloromethane as an eluent, and the yield is 85%. Matrix-assisted laser desorption ionization time-of-flight mass spectrometer (MALDI-TOF): Calculated value m/z, 784.35; Measured value m/z, 784.12. Elemental analysis (EA): Calculated value C, 88.74; H, 5.65; N, 3.57; Measured value C, 88.56; H, 5.37; N, 3.89.

Embodiment 4

The synthesis of Target structure 4 of the oxygen heterocyclic compound is shown in process formula 12:

argon atmosphere; the mixture was stirred until the iodine fades, and reacts for 0.5 hours. Next, compound (8) (3.2 mmol) was dissolved in 50 mL of THF solvent for removing water and oxygen, and then the mixed solution was introduced into the mixed solution prepared in the previous step under argon, and reacts for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.95 mmol of an intermediate compound (9) was obtained by using 200-300 meshes silica gel as a stationary phase and dichloromethane as an eluent, and the yield is 65%.

The obtained intermediate compound (9) was added into 100 mL of acetonitrile, and 2.5 mmol of boron tribromide

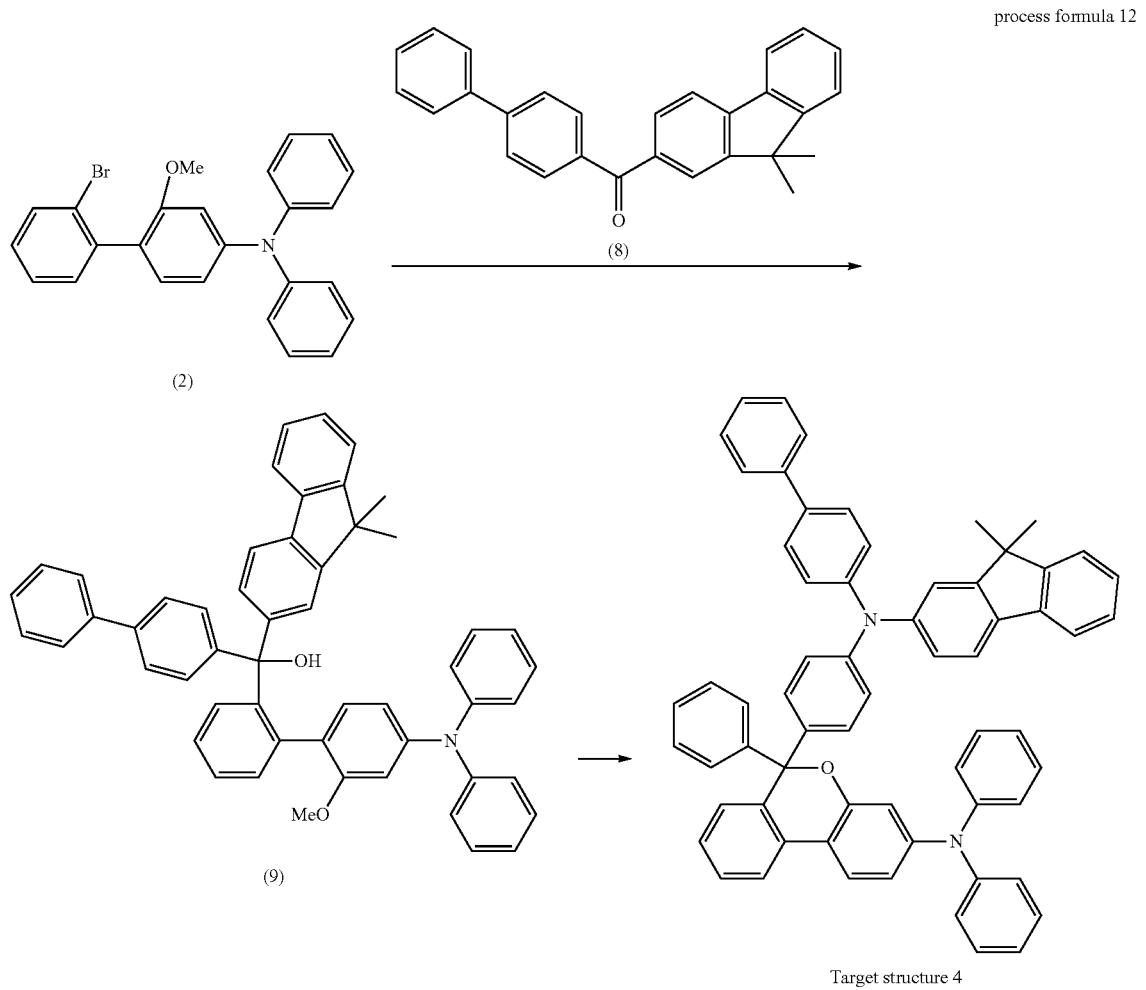

process formula 12

Target structure 4

In Embodiment 4, the step of producing the previous product-compound (2) can be similar to the step of producing the previous product-compound (2) in Embodiment 1. The preparation method of Target structure 4 of the oxygen heterocyclic compound provided by Embodiment 4 is as follows:

The product of the previous step-compound (2) (3 mmol), magnesium (Mg, 3.3 mmol), and one grain of I$_2$ were added into a 250 mL two-necked flask, and then 10 mL of THF solvent was added for water and oxygen removal under was added to the mixture, and stirred for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.7 mmol of Target structure 4 was obtained by using 200-300 meshes silica gel as a stationary phase and dichloromethane as an eluent, and the yield is 85%. Matrix-assisted laser desorption ionization time-of-flight mass spectrometer (MALDI-TOF): Calculated value m/z, 784.35; Measured value m/z, 784.12. Elemental analysis (EA): Calculated value C, 88.74; H, 5.65; N, 3.57; Measured value C, 88.56; H, 5.37; N, 3.89.

Embodiment 5

The synthesis of Target structure 5 of the oxygen heterocyclic compound is shown in process formula 13:

process formula 13

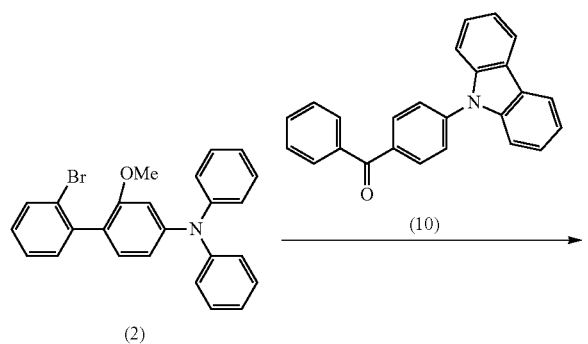
(2)

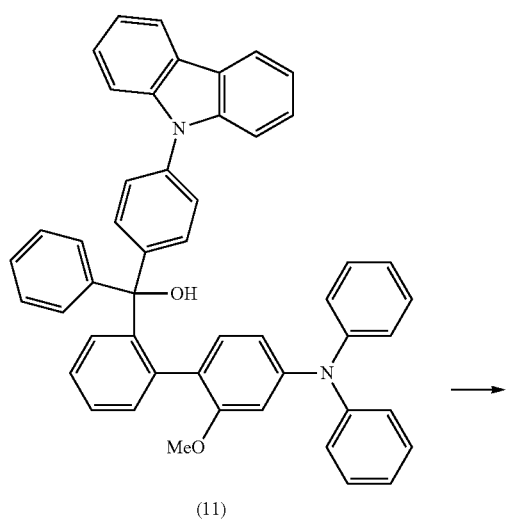
(11)

-continued

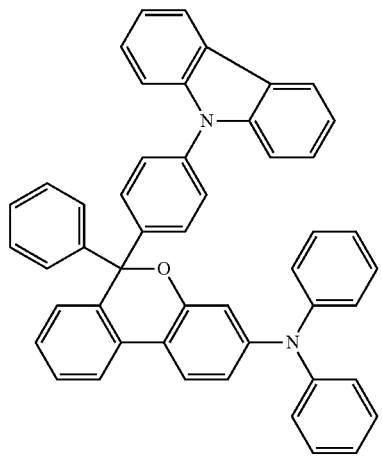

Target structure 5

In Embodiment 5, the step of producing the previous product-compound (2) can be similar to the step of producing the previous product-compound (2) in Embodiment 1. The preparation method of Target structure 5 of the oxygen heterocyclic compound provided by Embodiment 5 is as follows:

The product of the previous step-compound (2) (3 mmol), magnesium (Mg, 3.3 mmol), and one grain of I2 were added into a 250 mL two-necked flask, and then 10 mL of THF solvent was added for water and oxygen removal under argon atmosphere; the mixture was stirred until the iodine fades, and reacts for 0.5 hours. Next, compound (10) (3.2 mmol) was dissolved in 50 mL of THF solvent for removing water and oxygen, and then the mixed solution was introduced into the mixed solution prepared in the previous step under argon, and reacts for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.8 mmol of an intermediate compound (11) was obtained by using 200-300 meshes silica gel as a stationary phase and dichloromethane as an eluent, and the yield is 60%.

The obtained intermediate compound (11) was added into 100 mL of acetonitrile, and 2.5 mmol of boron tribromide was added to the mixture, and stirred for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.4 mmol of Target structure 5 was obtained by using 200-300 meshes silica gel as a stationary phase and dichloromethane as an eluent, and the yield is 80%. Matrix-assisted laser desorption ionization time-of-flight mass spectrometer (MALDI-TOF): Calculated value m/z, 667.27; Measured value m/z, 667.31. Elemental analysis (EA): Calculated value C, 88.26; H, 5.14; N, 4.20; Measured value C, 88.31; H, 5.21; N, 4.19.

Embodiment 6

The synthesis of Target structure 6 of the oxygen heterocyclic compound is shown in process formula 14:

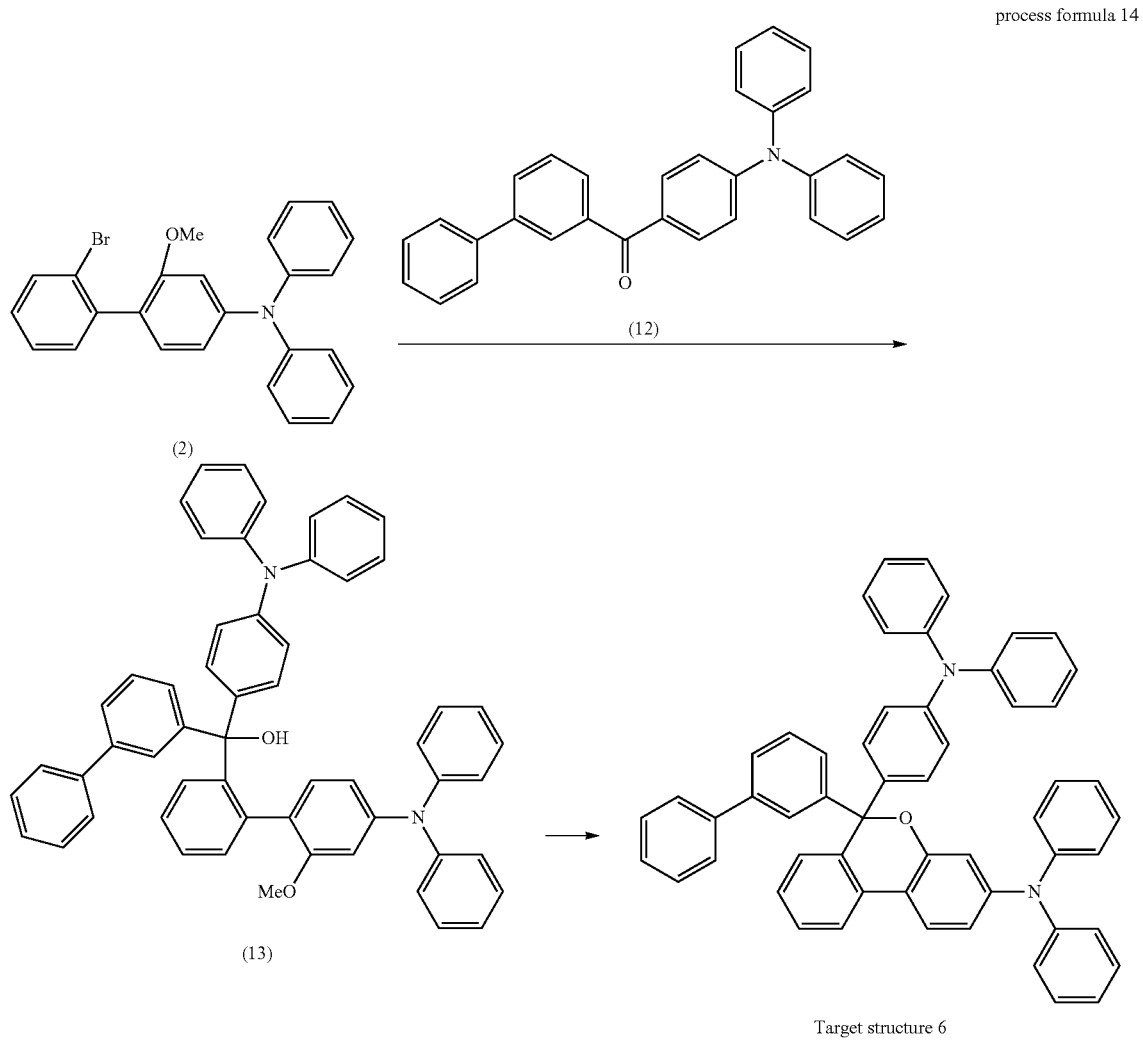

process formula 14

Target structure 6

In Embodiment 6, the step of producing the previous product-compound (2) can be similar to the step of producing the previous product-compound (2) in Embodiment 1. The preparation method of Target structure 6 of the oxygen heterocyclic compound provided by Embodiment 6 is as follows:

The product of the previous step-compound (2) (3 mmol), magnesium (Mg, 3.3 mmol), and one grain of 12 were added into a 250 mL two-necked flask, and then 10 mL of THF solvent was added for water and oxygen removal under argon atmosphere; the mixture was stirred until the iodine fades, and reacts for 0.5 hours. Next, compound (12) (3.2 mmol) was dissolved in 50 mL of THF solvent for removing water and oxygen, and then the mixed solution was introduced into the mixed solution prepared in the previous step under argon, and reacts for 12 hours. The product was dissolved in dichloromethane (300 mL) and saturated $NH_4Cl$ (200 mL) was added in the mixture. By extraction of dichloromethane, the organic phase was dried by anhydrous sodium sulfate and then subject to column separation after concentration. 2.2 mmol of an intermediate compound (13) was obtained by using 200-300 meshes silica gel as a stationary phase and dichloromethane as an eluent, and the yield is 72%.

The obtained intermediate compound (13) was added into 100 mL of acetonitrile, and 2.5 mmol of boron tribromide was added to the mixture, and stirred for 12 hours. The product was dissolved in dichloromethane (300 mL) and saturated $NH_4Cl$ (200 mL) was added in the mixture. By extraction of dichloromethane, the organic phase was dried by anhydrous sodium sulfate and then subject to column separation after concentration. 1.6 mmol of Target structure 6 was obtained by using 200-300 meshes silica gel as a stationary phase and dichloromethane as an eluent, and the yield is 74%. Matrix-assisted laser desorption ionization time-of-flight mass spectrometer (MALDI-TOF): Calculated value m/z, 744.31; Measured value m/z, 744.31. Elemental analysis (EA): Calculated value C, 88.68; H, 5.41; N, 3.76; Measured value C, 88.52; H, 5.29; N, 3.87.

Embodiment 7

The synthesis of Target structure 7 of the oxygen heterocyclic compound is shown in process formula 15:

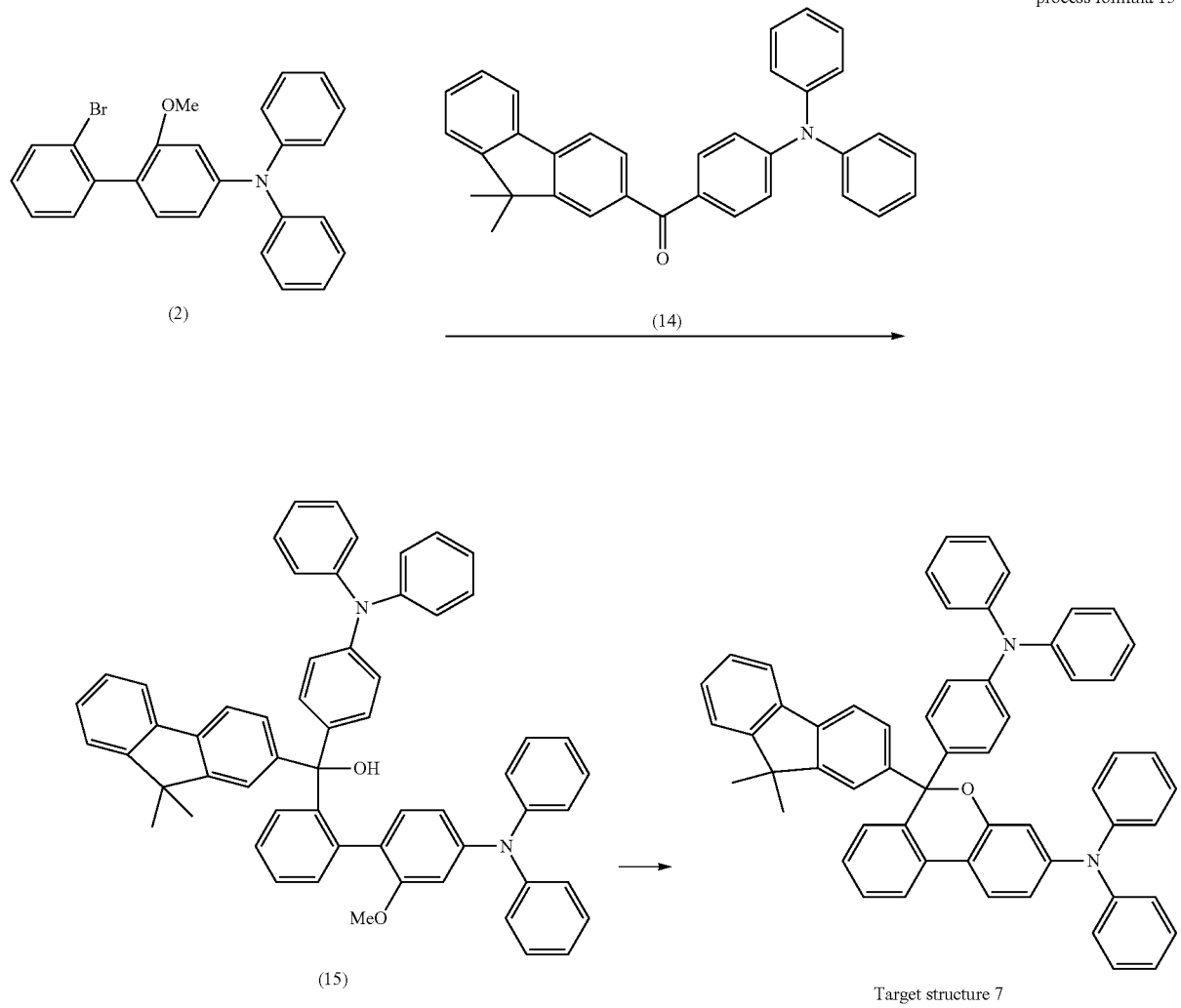

In Embodiment 7, the step of producing the previous product-compound (2) can be similar to the step of producing the previous product-compound (2) in Embodiment 1. The preparation method of Target structure 7 of the oxygen heterocyclic compound provided by Embodiment 7 is as follows:

The product of the previous step-compound (2) (3 mmol), magnesium (Mg, 3.3 mmol), and one grain of I2 were added into a 250 mL two-necked flask, and then 10 mL of THF solvent was added for water and oxygen removal under argon atmosphere; the mixture was stirred until the iodine fades, and reacts for 0.5 hours. Next, compound (14) (3.2 mmol) was dissolved in 50 mL of THF solvent for removing water and oxygen, and then the mixed solution was introduced into the mixed solution prepared in the previous step under argon, and reacts for 12 hours. The product was dissolved in dichloromethane (300 mL) and saturated NH₄Cl (200 mL) was added in the mixture. By extraction of dichloromethane, the organic phase was dried by anhydrous sodium sulfate and then subject to column separation after concentration. 2.4 mmol of an intermediate compound (15) was obtained by using 200-300 meshes silica gel as a stationary phase and dichloromethane as an eluent, and the yield is 79%.

The obtained intermediate compound (15) was added into 100 mL of acetonitrile, and 2.5 mmol of boron tribromide was added to the mixture, and stirred for 12 hours. The product was dissolved in dichloromethane (300 mL) and saturated NH₄Cl (200 mL) was added in the mixture. By extraction of dichloromethane, the organic phase was dried by anhydrous sodium sulfate and then subject to column separation after concentration. 1.5 mmol of Target structure 7 was obtained by using 200-300 meshes silica gel as a stationary phase and dichloromethane as an eluent, and the yield is 65%. Matrix-assisted laser desorption ionization time-of-flight mass spectrometer (MALDI-TOF): Calculated value m/z, 784.35; Measured value m/z, 784.13. Elemental analysis (EA): Calculated value C, 88.74; H, 5.65; N, 3.57; Measured value C, 88.69; H, 5.37; N, 3.48.

Embodiment 8

The synthesis of Target structure 8 of the oxygen heterocyclic compound is shown in process formula 16:

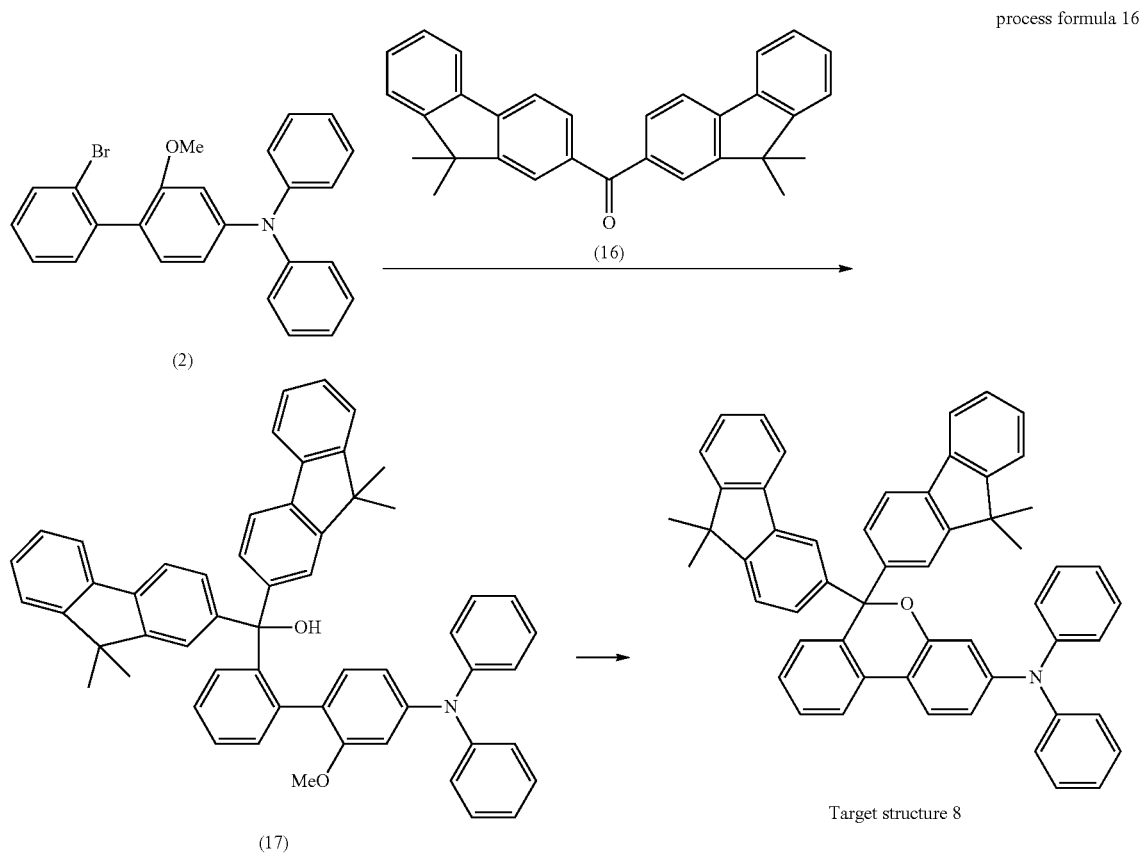

process formula 16

In Embodiment 8, the step of producing the previous product-compound (2) can be similar to the step of producing the previous product-compound (2) in Embodiment 1. The preparation method of Target structure 8 of the oxygen heterocyclic compound provided by Embodiment 8 is as follows:

The product of the previous step-compound (2) (3 mmol), magnesium (Mg, 3.3 mmol), and one grain of I2 were added into a 250 mL two-necked flask, and then 10 mL of THF solvent was added for water and oxygen removal under argon atmosphere; the mixture was stirred until the iodine fades, and reacts for 0.5 hours. Next, compound (16) (3.2 mmol) was dissolved in 50 mL of THF solvent for removing water and oxygen, and then the mixed solution was introduced into the mixed solution prepared in the previous step under argon, and reacts for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 2.1 mmol of an intermediate compound (17) was obtained by using 200-300 meshes silica gel as a stationary phase and dichloromethane as an eluent, and the yield is 70%.

The obtained intermediate compound (17) was added into 100 mL of acetonitrile, and 2.5 mmol of boron tribromide was added to the mixture, and stirred for 12 hours. The product was dissolved in dichloromethane (300 mL) and saturated NH$_4$Cl (200 mL) was added in the mixture. By extraction of dichloromethane, the organic phase was dried by anhydrous sodium sulfate and then subject to column separation after concentration. 1.5 mmol of Target structure 7 was obtained by using 200-300 meshes silica gel as a stationary phase and dichloromethane as an eluent, and the yield is 65%. Matrix-assisted laser desorption ionization time-of-flight mass spectrometer (MALDI-TOF): Calculated value m/z, 733.96; Measured value m/z, 733.79. Elemental analysis (EA): Calculated value C, 90.01; H, 5.91; N, 1.91; Measured value C, 89.87; H, 6.05; N, 1.88.

Embodiment 9

Target structure 9 is shown in formula 17. Refer to the synthesis of target structure 1 for the synthesis path of target structure 9. The yield of target structure 9 is 65%. Matrix-assisted laser desorption ionization time-of-flight mass spectrometer (MALDI-TOF): Calculated value m/z, 577.73; Measured value m/z, 577.35. Elemental analysis (EA): Calculated value C, 89.40; H, 5.41; N, 2.42; Measured value C, 89.24; H, 5.32; N, 2.59.

Formula 17

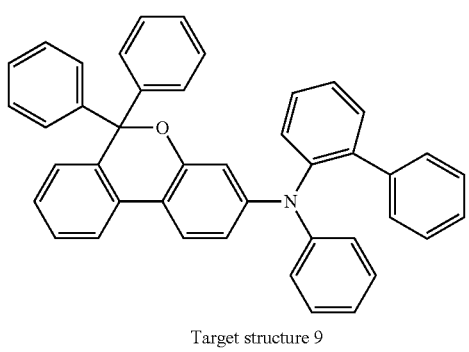

Target structure 9

Embodiment 10

Target structure 10 is shown in formula 18. Refer to the synthesis of target structure 1 for the synthesis path of target structure 10. The yield of target structure 10 is 71%. Matrix-assisted laser desorption ionization time-of-flight mass spectrometer (MALDI-TOF): Calculated value m/z, 617.79; Measured value m/z, 617.54. Elemental analysis (EA): Calculated value C, 89.43; H, 5.71; N, 2.27; Measured value C, 89.21; H, 5.85; N, 2.19.

Formula 18

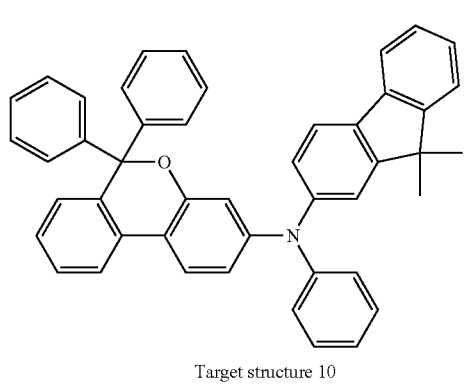

Target structure 10

Embodiment 11

Target structure 11 is shown in formula 19. Refer to the synthesis of target structure 1 for the synthesis path of target structure 11. The yield of target structure 11 is 74%. Matrix-assisted laser desorption ionization time-of-flight mass spectrometer (MALDI-TOF): Calculated value m/z, 693.89; Measured value m/z, 693.77. Elemental analysis (EA): Calculated value C, 89.43; H, 5.71; N, 2.27; Measured value C, 89.21; H, 5.85; N, 2.19.

Formula 19

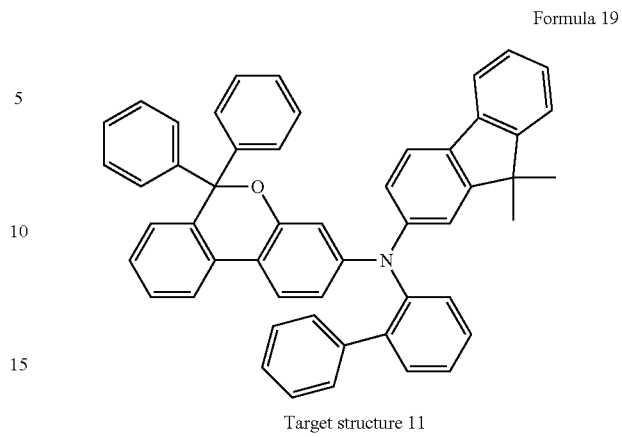

Target structure 11

Testing and Experimental Verification

After testing and experimental verification, the energy levels of the oxygen heterocyclic compound of target structure 1-11 mentioned above are shown in Table 1 below.

TABLE 1

| oxygen heterocyclic compound | Eg (eV) | HOMO (eV) | T1 (eV) |
| --- | --- | --- | --- |
| Target structure 1  | 3.34 | −5.45 | 2.89 |
| Target structure 2  | 3.26 | −5.31 | 2.75 |
| Target structure 3  | 3.22 | −5.35 | 2.78 |
| Target structure 4  | 3.21 | −5.37 | 2.84 |
| Target structure 5  | 3.38 | −5.32 | 2.91 |
| Target structure 6  | 3.27 | −5.40 | 2.88 |
| Target structure 7  | 3.56 | −5.35 | 2.79 |
| Target structure 8  | 3.28 | −5.43 | 2.91 |
| Target structure 9  | 3.19 | −5.45 | 2.88 |
| Target structure 10 | 3.40 | −5.43 | 2.85 |
| Target structure 11 | 3.25 | −5.47 | 2.79 |

An electronic device provided by one embodiment of the present disclosure is produced according to the method known in the art. The electronic device is for example an electroluminescent device, specifically comprising an ITO layer, a HAT-CN layer (e.g. 5 nm of thickness), an organic material layer comprising the oxygen heterocyclic compound having any of above target structures (e.g. 30 nm of thickness), a Firpic:B3PyPB layer (12%, 10 nm), a TPBi layer (e.g. 40 nm of thickness), a LiF layer (e.g. 2 nm of thickness), and a Al layer (e.g. 100 nm of thickness). After testing and experimental verification, for each of the oxygen heterocyclic compounds as shown in above target structures 1-11, performance data of the electroluminescent device having the organic material layer comprising the oxygen heterocyclic compound of the target structure is shown in below Table 2.

TABLE 2

| Organic material layer | Voltage (v) | Highest efficiency (cd/A) |
| --- | --- | --- |
| Target structure 1 | 3.2 | 19.9 |
| Target structure 2 | 3.3 | 30.2 |
| Target structure 3 | 3.2 | 24.5 |
| Target structure 4 | 3.4 | 29.8 |

TABLE 2-continued

| Organic material layer | Voltage (v) | Highest efficiency (cd/A) |
| --- | --- | --- |
| Target structure 5 | 3.3 | 31.7 |
| Target structure 6 | 3.1 | 27.7 |
| Target structure 7 | 3.4 | 29.5 |
| Target structure 8 | 3.5 | 27.3 |
| Target structure 9 | 3.7 | 25.4 |
| Target structure 10 | 3.9 | 22.5 |
| Target structure 11 | 3.8 | 27.1 |

In an oxygen heterocyclic compound, an application thereof, and an electronic device using the same according to the embodiments of the present disclosure, the oxygen heterocyclic compound includes an aromatic amine portion and an oxygen heterocyclic portion, wherein the aromatic amine portion may effectively promote the hole injection and transport performance of the organic material so as to improve the balance between holes and electrons in the organic light-emitting diode to achieve lower voltages and higher efficiencies. In addition, the oxygen heterocyclic portion is conducive to the formation of molten evaporation materials, which is conducive to the stability of mass production evaporation. This type of material can achieve high-efficiency electroluminescent device preparation, which can be used in the manufacture of display devices.

In summary, although the present invention has been described with preferred embodiments thereof, the present invention is not limited thereto. It is understood that many changes and modifications to the described embodiments can be carried out by the skilled person in the art without departing from the scope and the spirit of the invention that is intended to be limited only by the appended claims.

What is claimed is:

1. An oxygen heterocyclic compound, having a structural formula as represented by following formula 1:

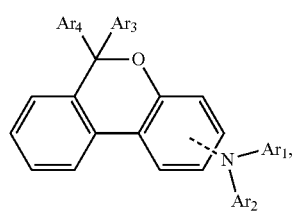

formula 1 wherein, Ar1 and Ar2 are independently represented by any of following formula 301 to formula 332:

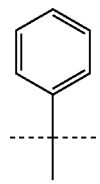

formula 301

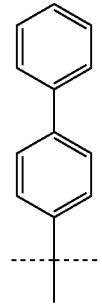

formula 302

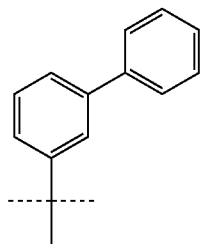

formula 303

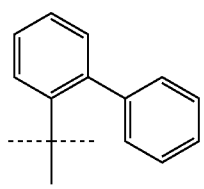

formula 304

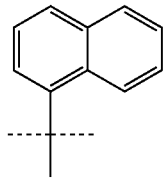

formula 305

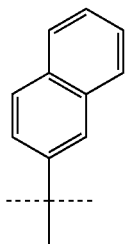

formula 306

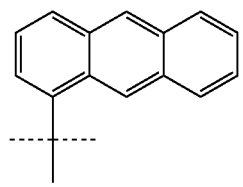

formula 307

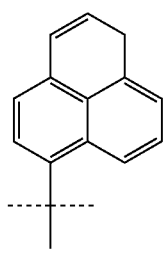

formula 308

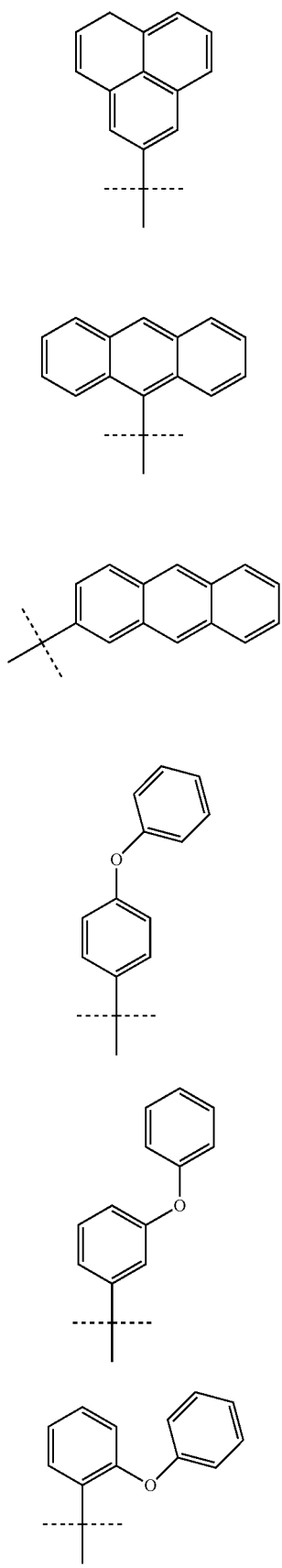
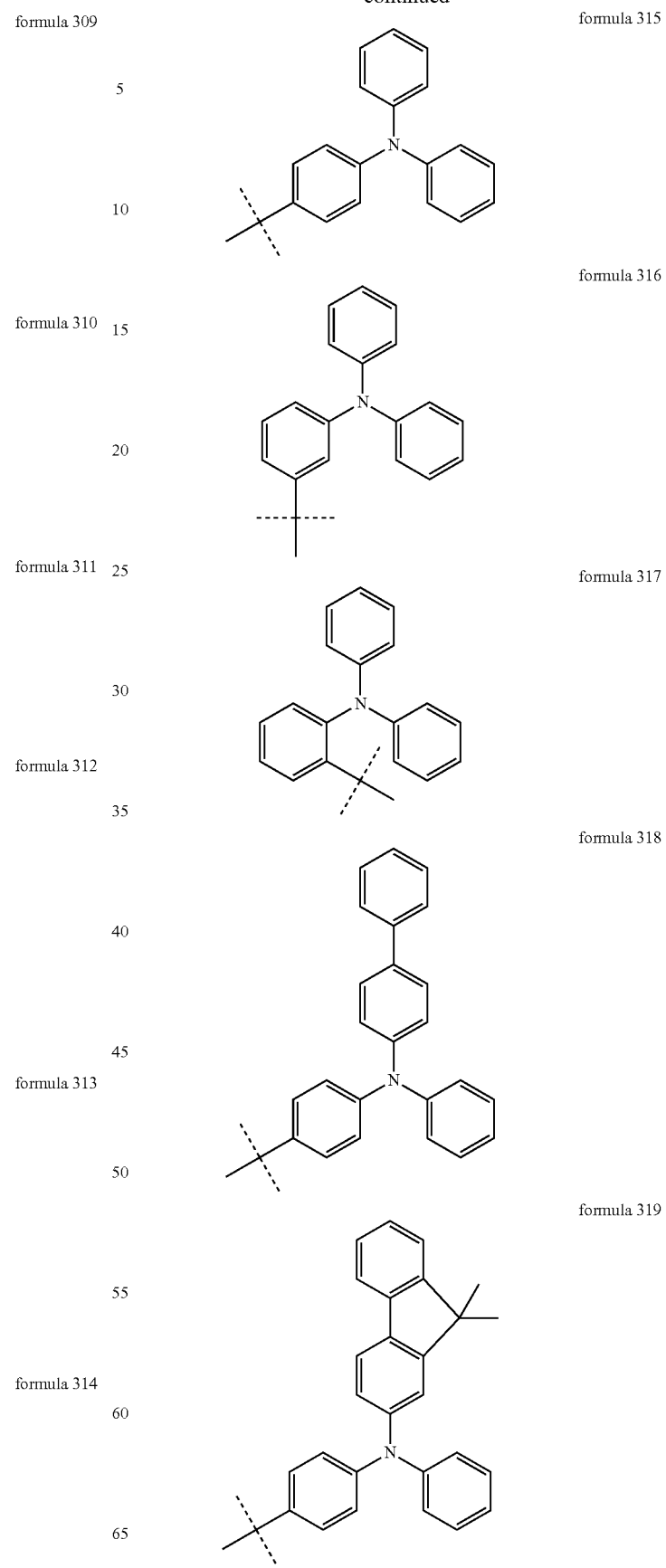

formula 320
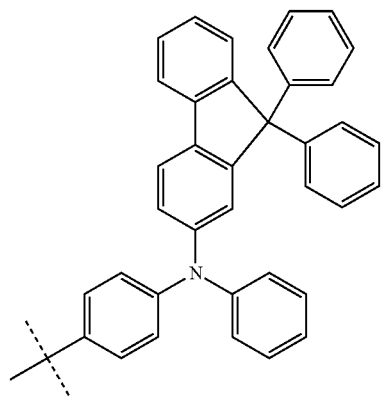
formula 321
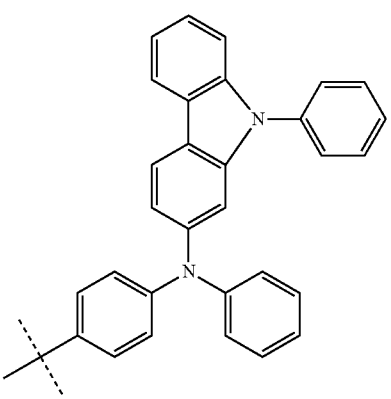
formula 322
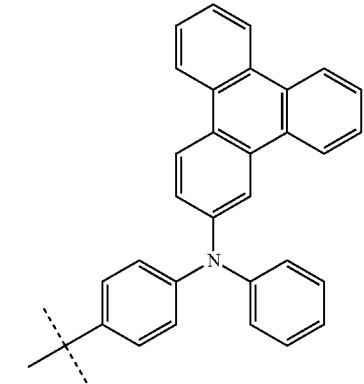
formula 323
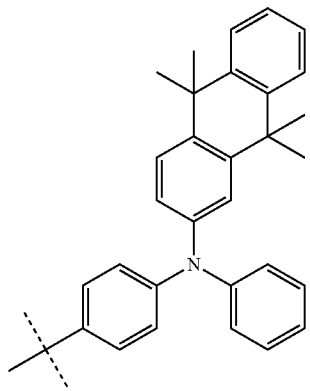
formula 324
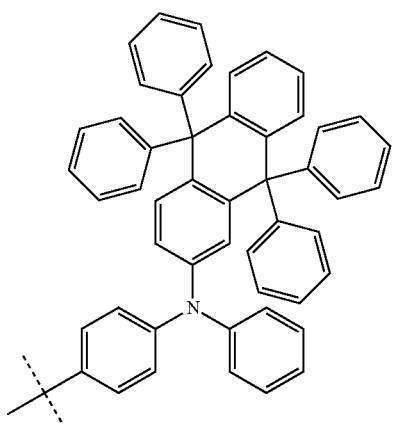
formula 325
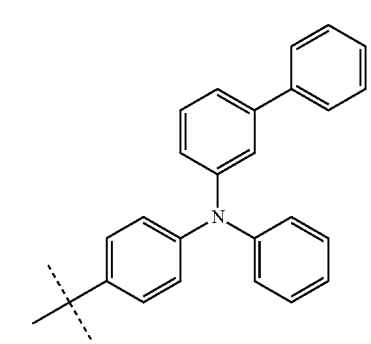
formula 326
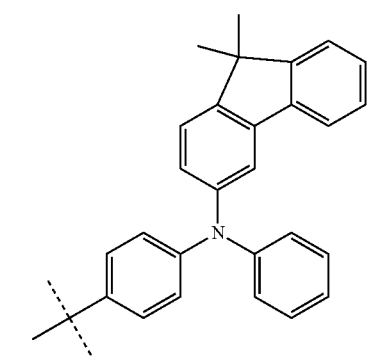
formula 327
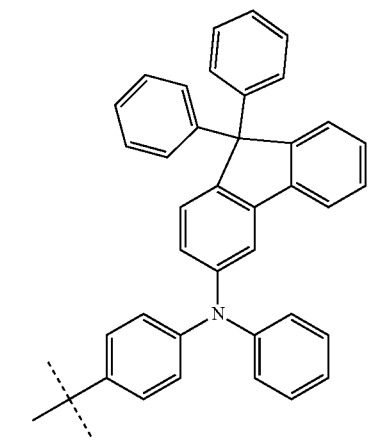

formula 328

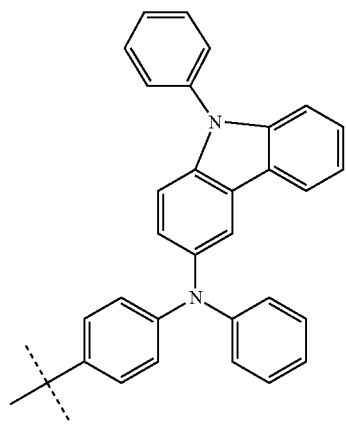

formula 329

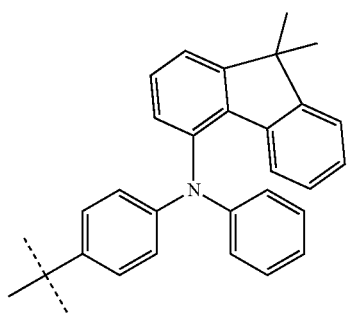

formula 330

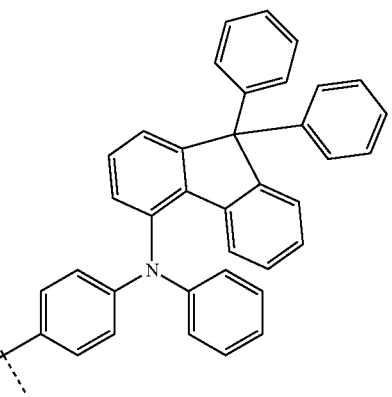

formula 331

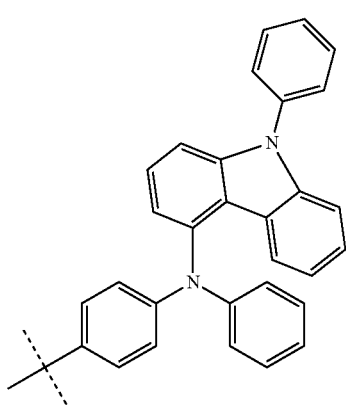

formula 332

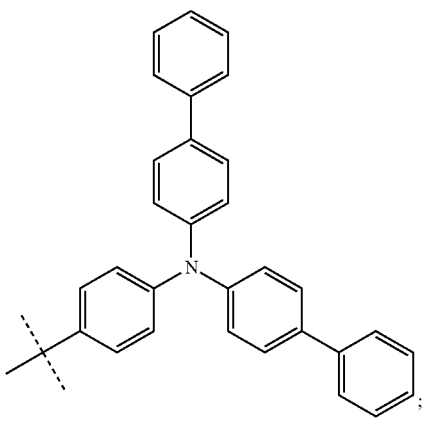

and Ar3 and Ar4 are independently selected from the group consisting of C1 to C22 alkyl groups, C1 to C22 alkoxy groups, C1 to C22 heteroalkyl groups, single or multiple substituted or unsubstituted aryl groups, or substituted or unsubstituted heteroaryl groups, or Ar3 and Ar4 together form a single or fused aromatic or heterocyclic ring when Ar3 and Ar4 are adjacent aryl groups or heteroaryl groups connected to each other, wherein heteroatoms of the heteroaryl groups are O, N, F, S, or Si.

2. The oxygen heterocyclic compound according to claim 1, wherein the oxygen heterocyclic compound has a structural formula represented by following formula 2:

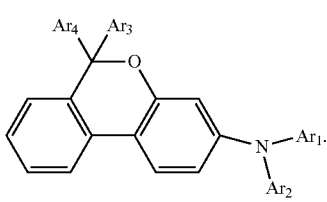

formula 2

3. The oxygen heterocyclic compound according to claim 1, wherein Ar3 and Ar4 are independently represented by any of following formula 301 to formula 332 and formula 401 to formula 403:

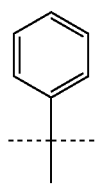

formula 301 formula 302
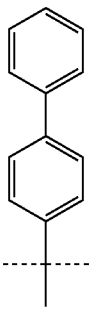
formula 303
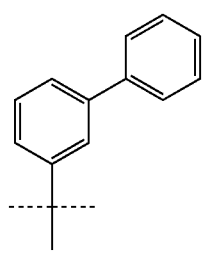
formula 304
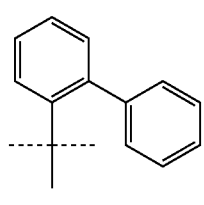
formula 305
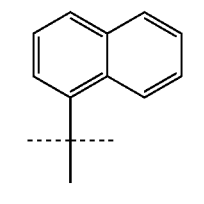
formula 306
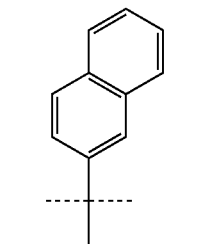
formula 307
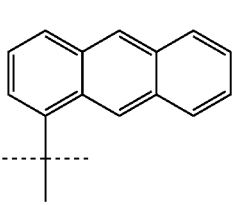
formula 308
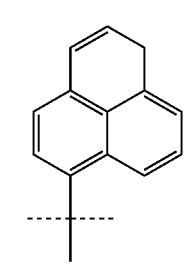
formula 309
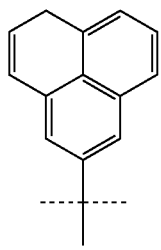
formula 310
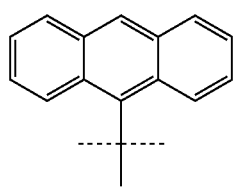
formula 311
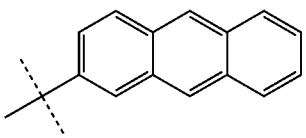
formula 312
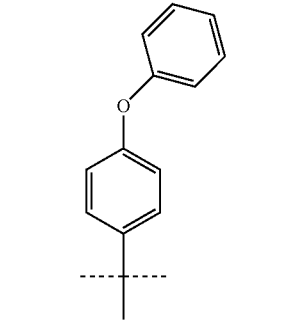
formula 313
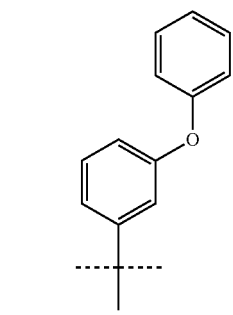
formula 314
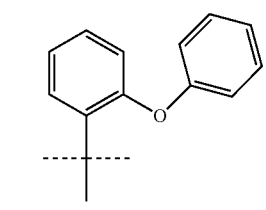

formula 315
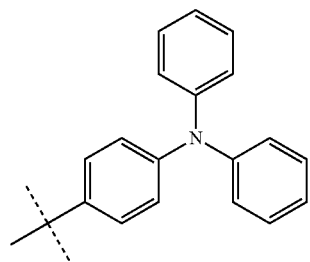
formula 316
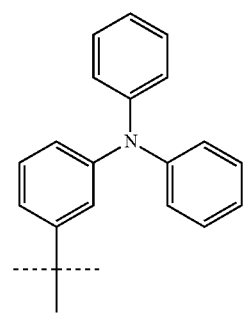
formula 317
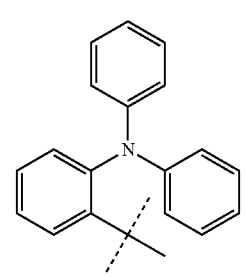
formula 318
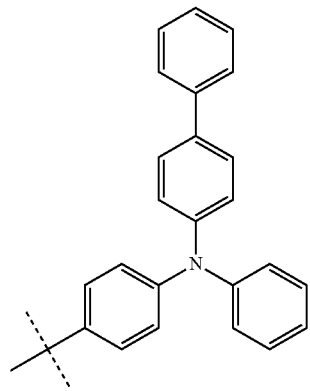
formula 319
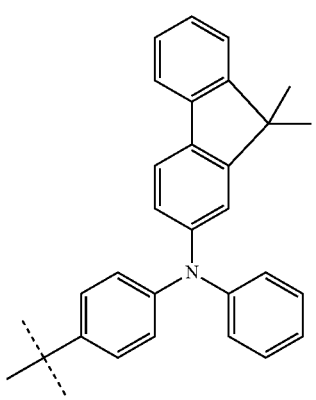
formula 320
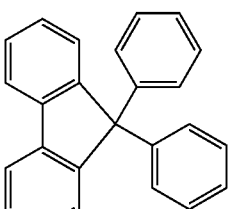
formula 321
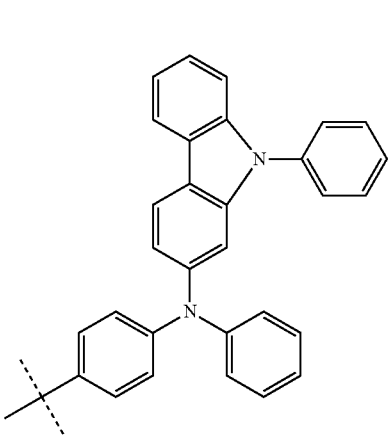
formula 322
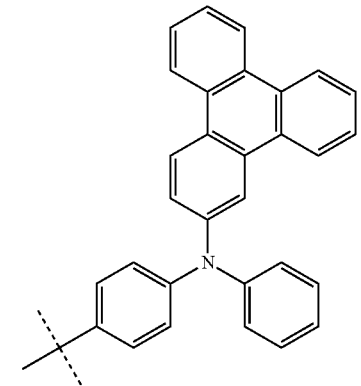
formula 323
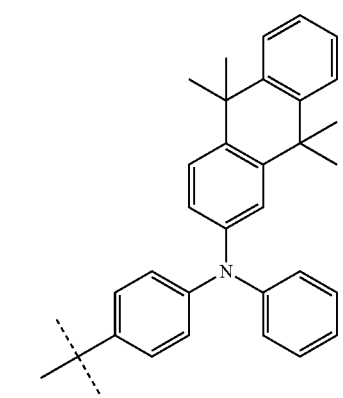

-continued
formula 324
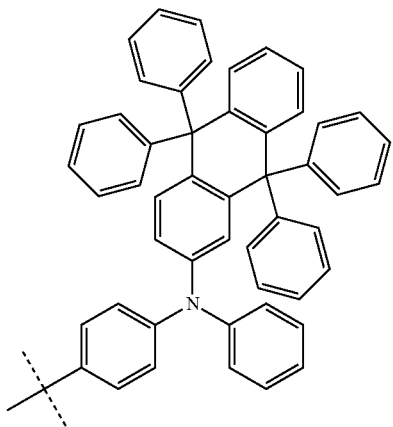
formula 325
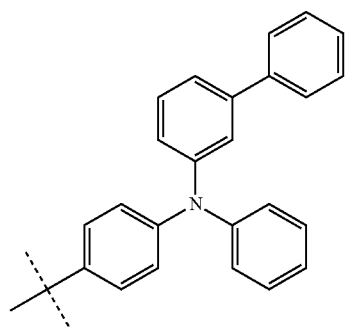
formula 326
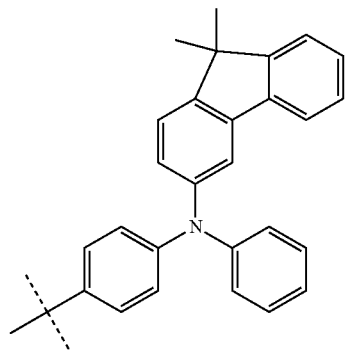
formula 327
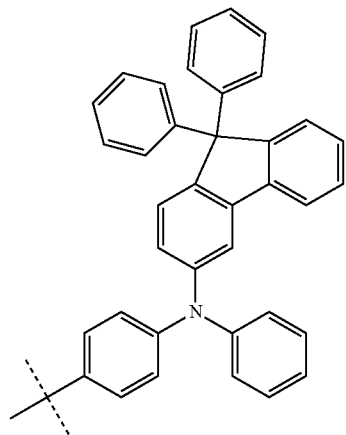
formula 328
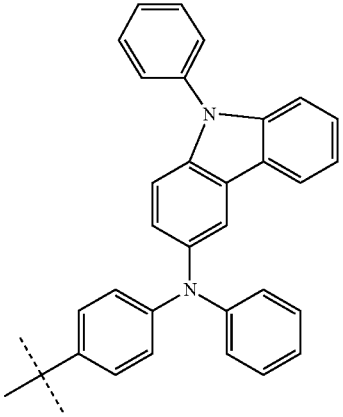
formula 329
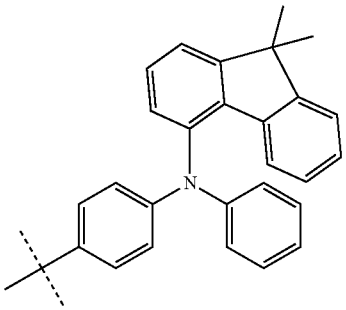
formula 330
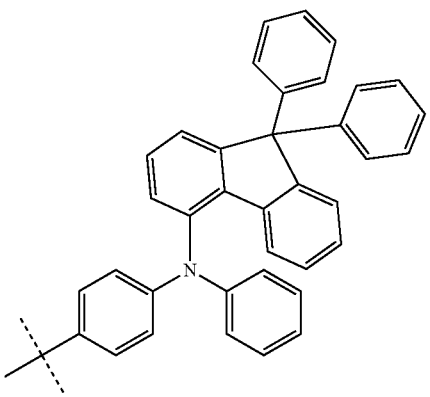
formula 331
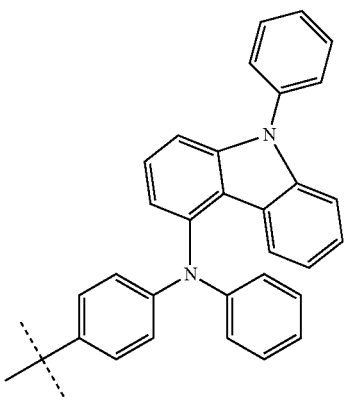

formula 332
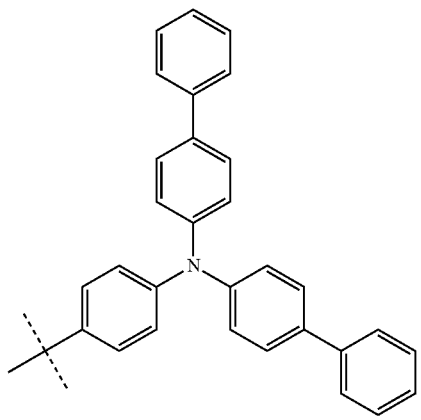
formula 401
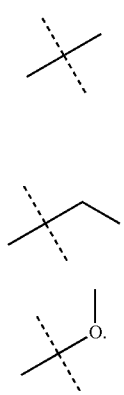
formula 402
formula 403
formula 503
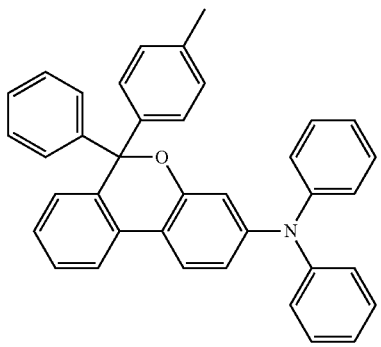
formula 504
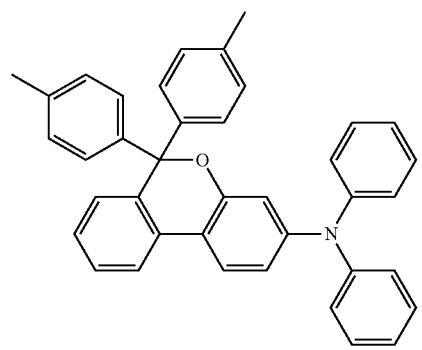
formula 505
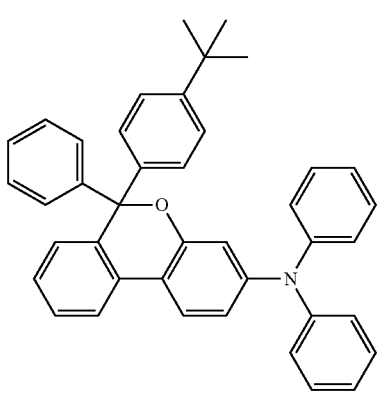
4. The oxygen heterocyclic compound according to claim 2, wherein the oxygen heterocyclic compound has a structural formula represented by any of following formula 501 to formula 508:
formula 501
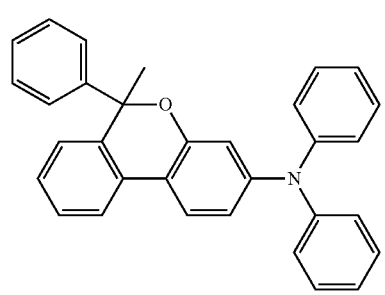
formula 502
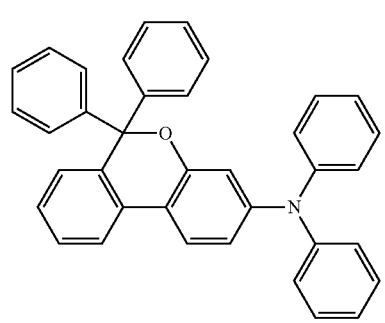
formula 506
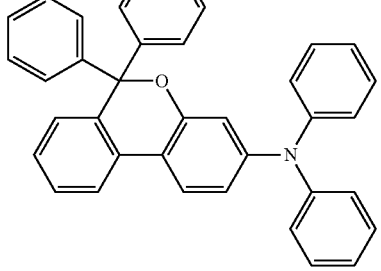
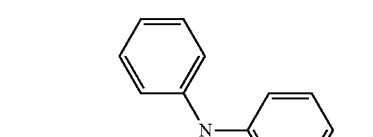

formula 507
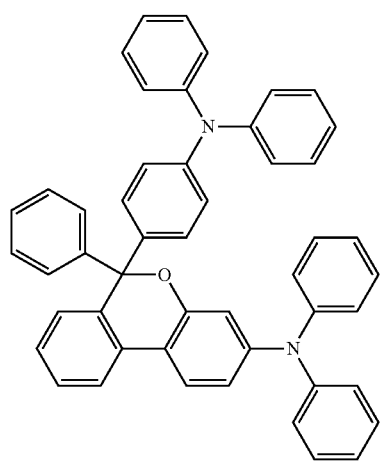
formula 602
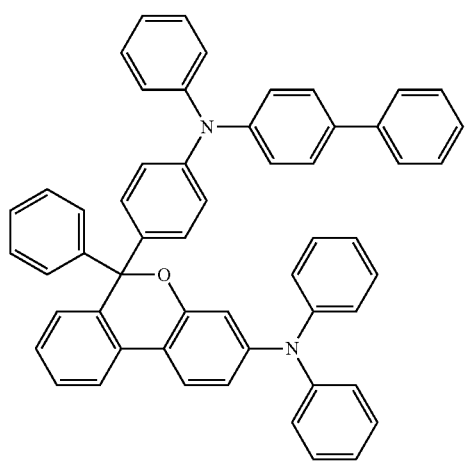
formula 508
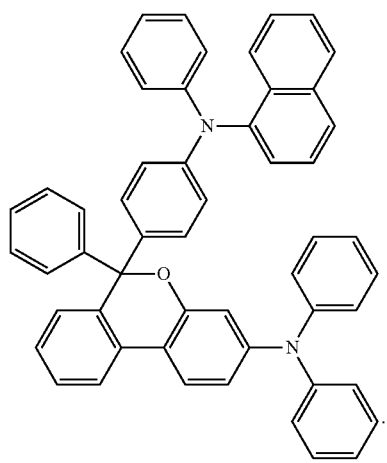
formula 603
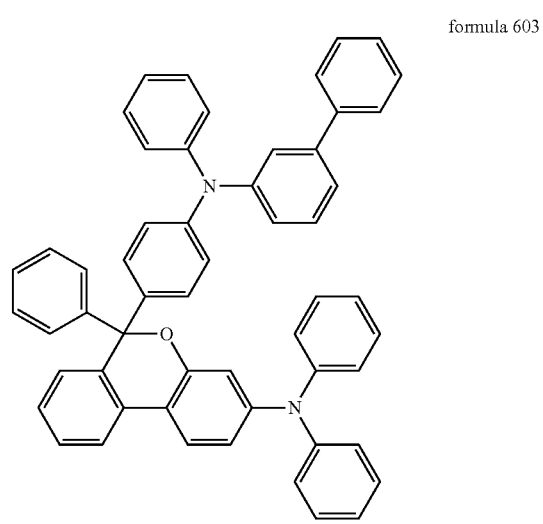
5. The oxygen heterocyclic compound according to claim 2, wherein the oxygen heterocyclic compound has a structure as represented by any of following formula 601 to formula 617:
formula 601
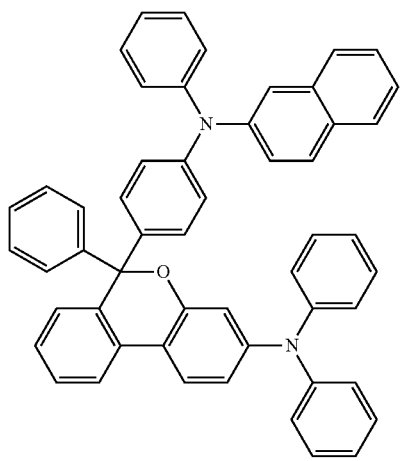
formula 604
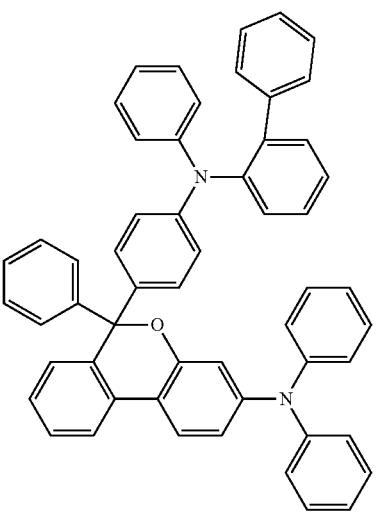

formula 605
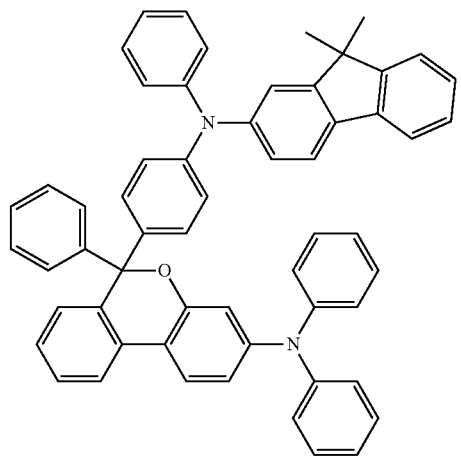
formula 606
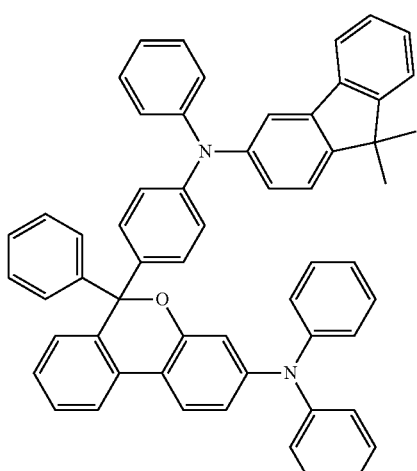
formula 607
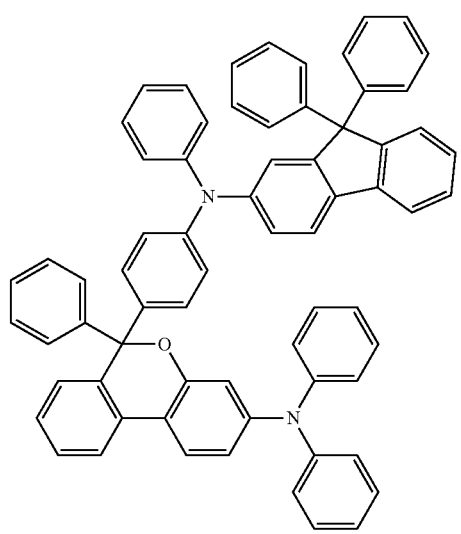
formula 608
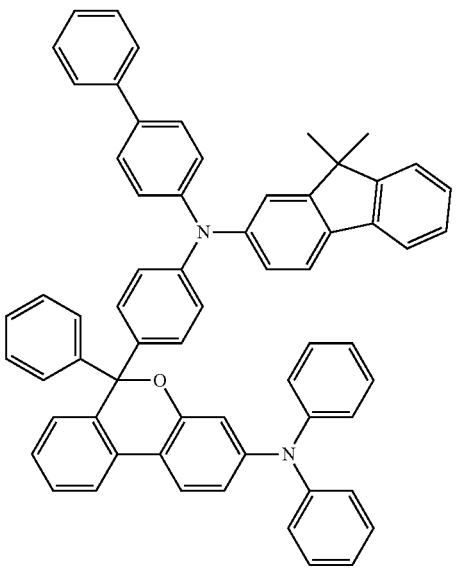
formula 609
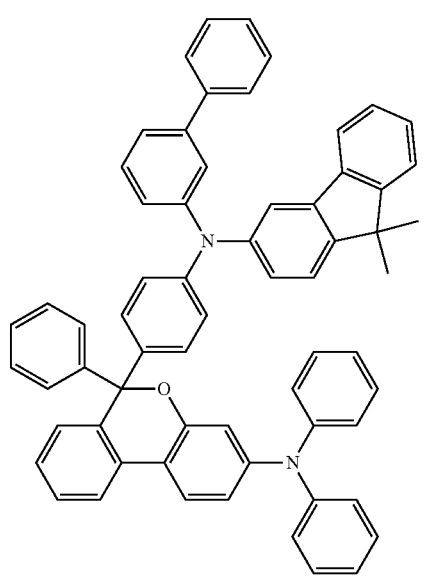
formula 610
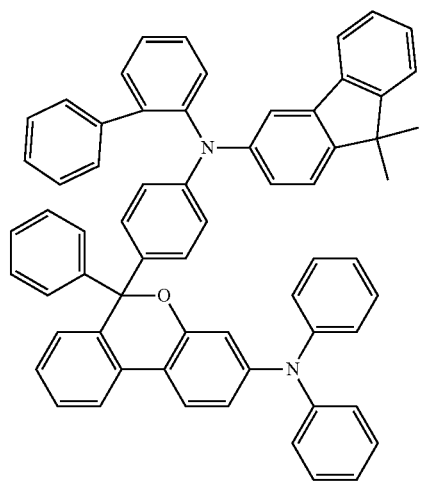

formula 611
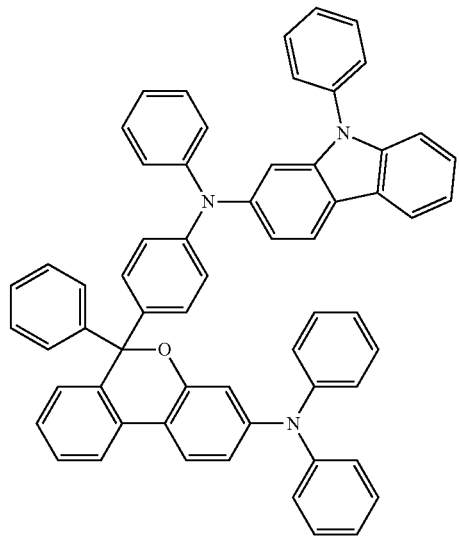
formula 612
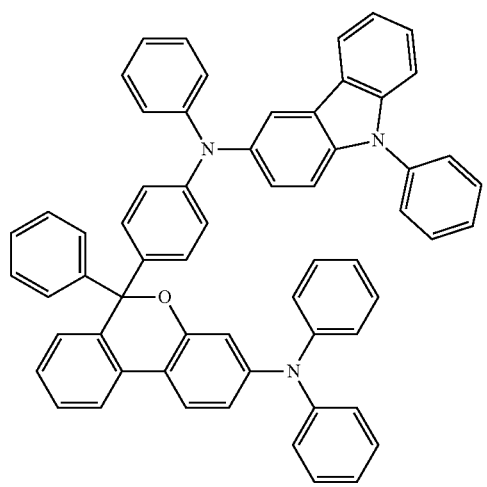
formula 613
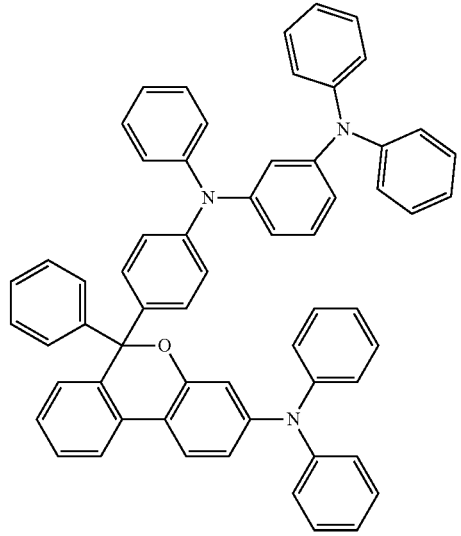
formula 614
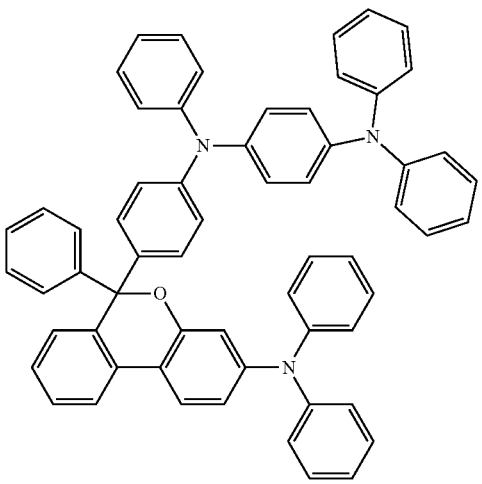
formula 615
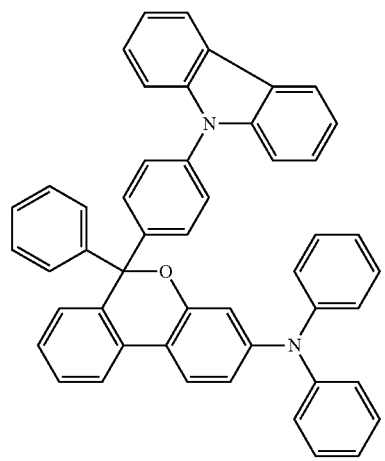
formula 616
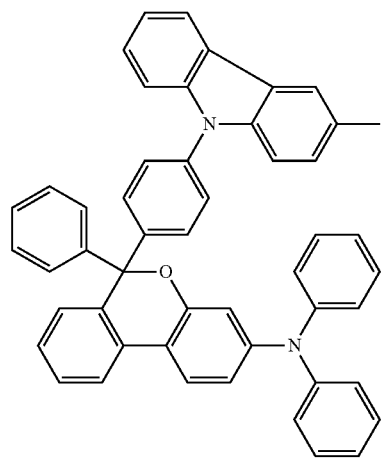

-continued
formula 617
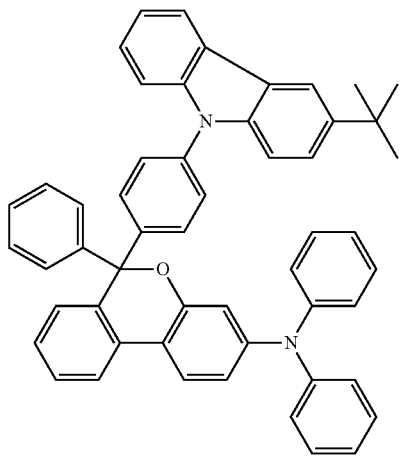
6. The oxygen heterocyclic compound according to claim 2, wherein the oxygen heterocyclic compound has a structure as represented by any of following formula 701 to formula 722:
formula 701
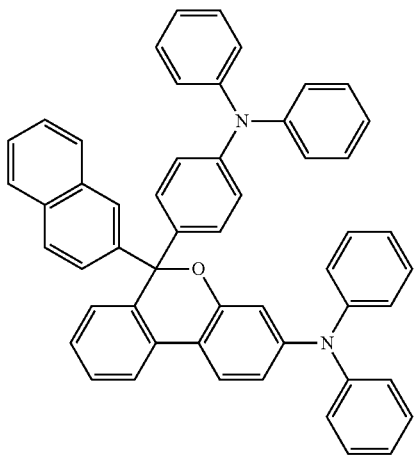
formula 702
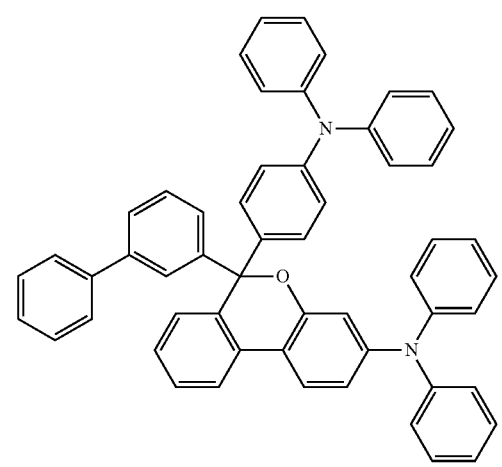
-continued
formula 703
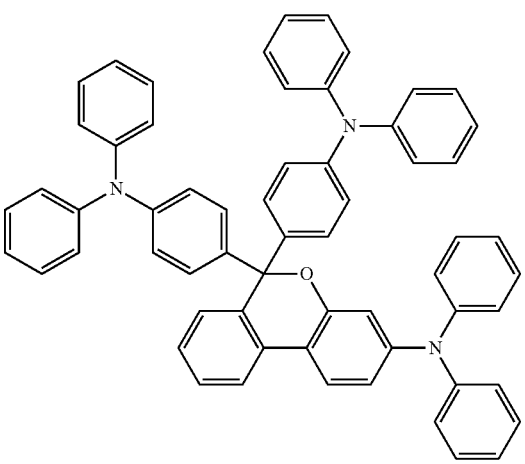
formula 704
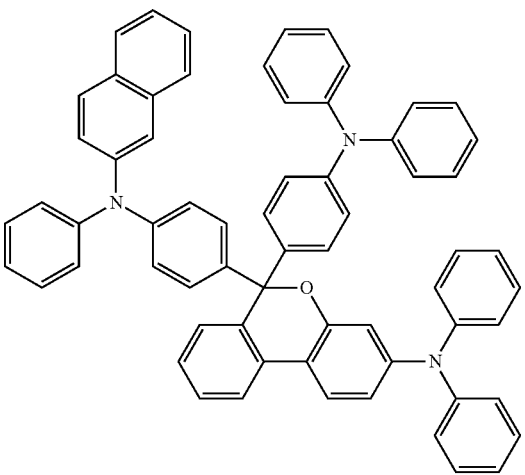
formula 705 formula 706
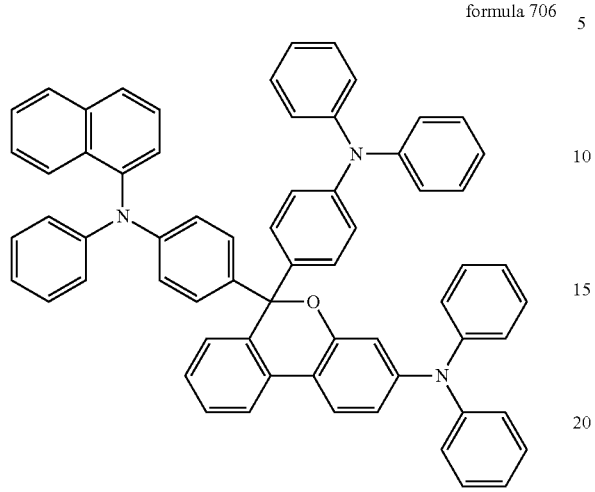
formula 707
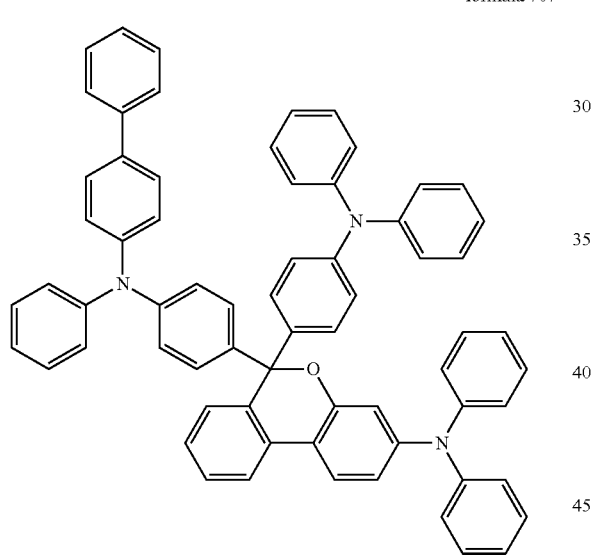
formula 708
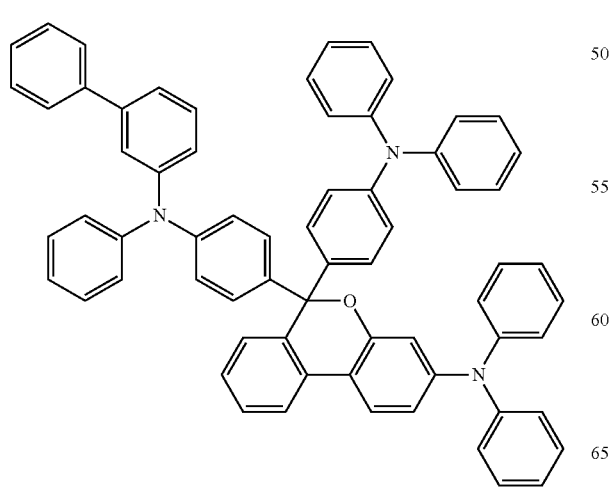
formula 709
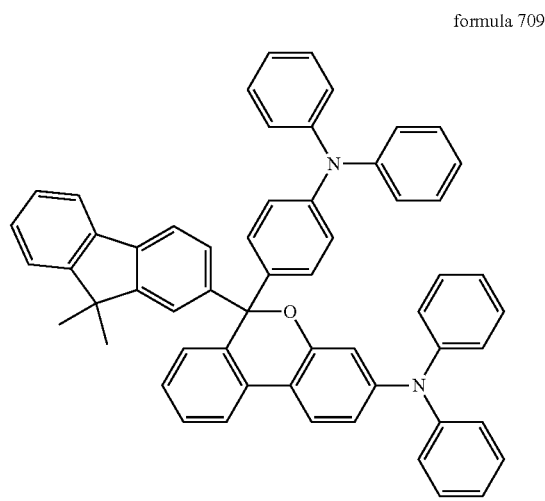
formula 710
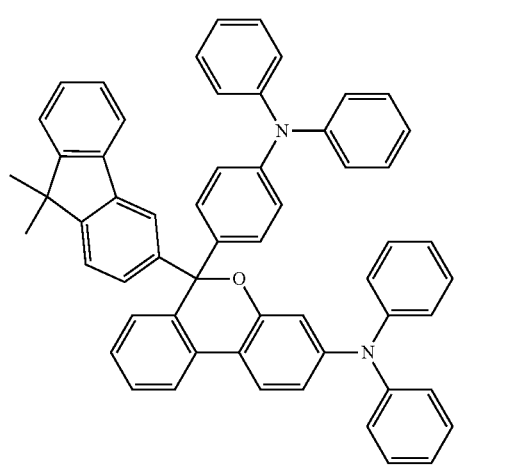
formula 711
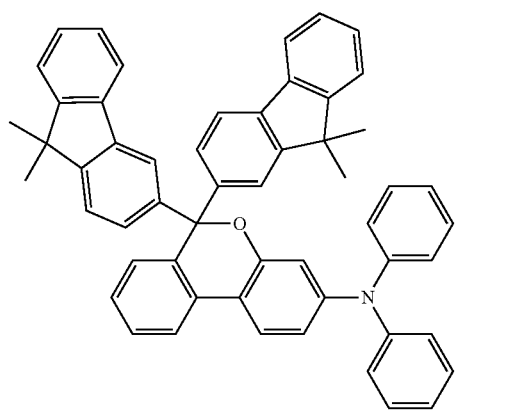

-continued
formula 712
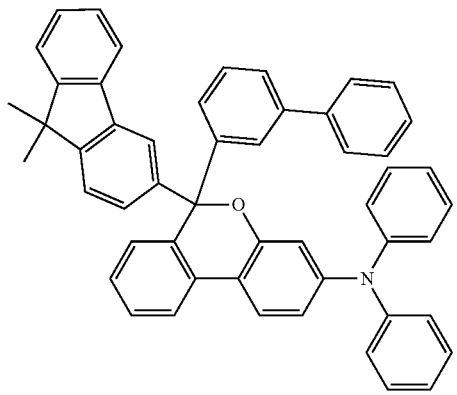
formula 713
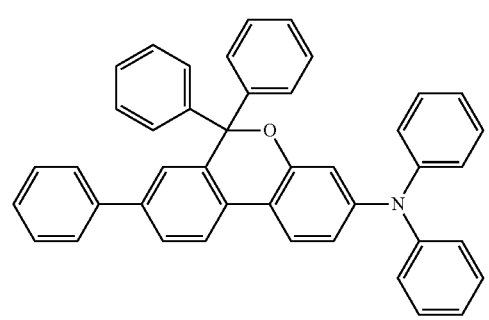
formula 714
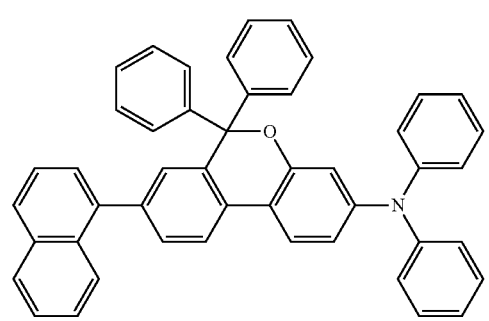
formula 715
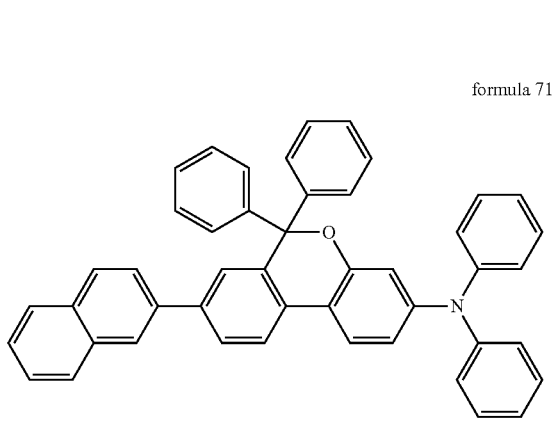
-continued
formula 716
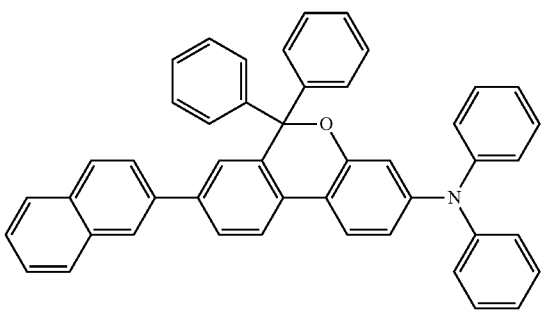
formula 717
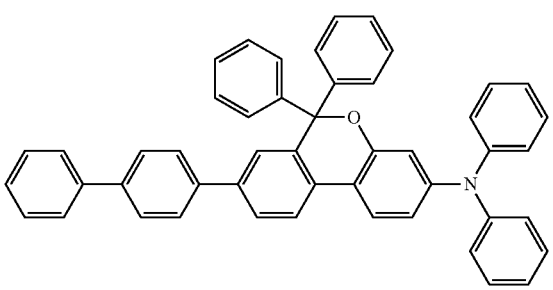
formula 718
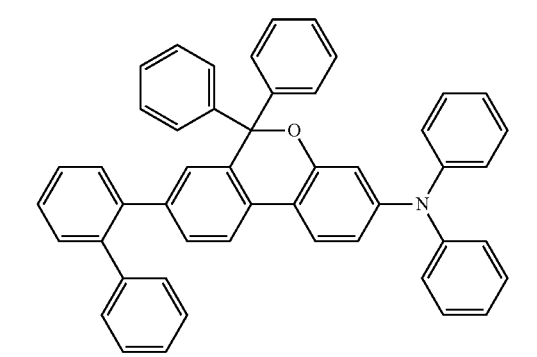
formula 719
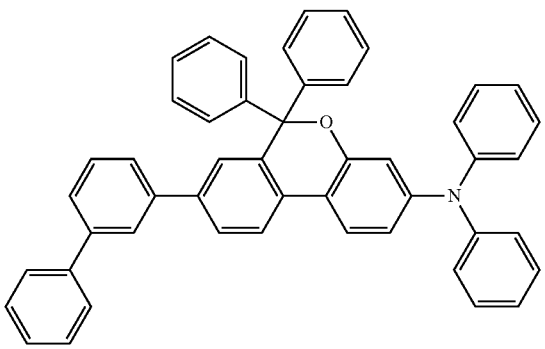

formula 720
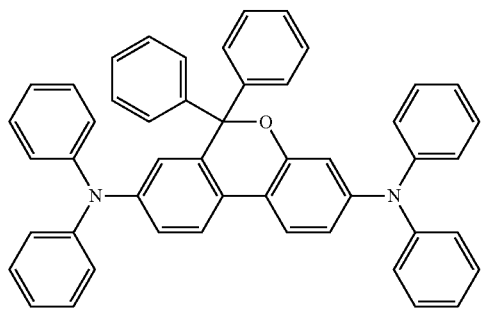
formula 721
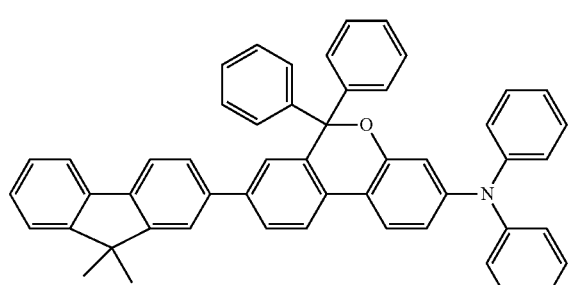
formula 722
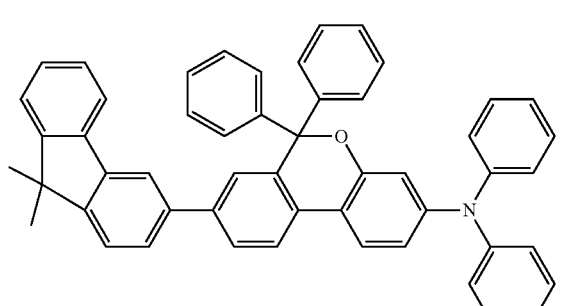
7. Oxygen heterocyclic compound according to claim 2, wherein the oxygen heterocyclic compound has a structure as represented by any of following formula 801 to formula 819:
formula 801
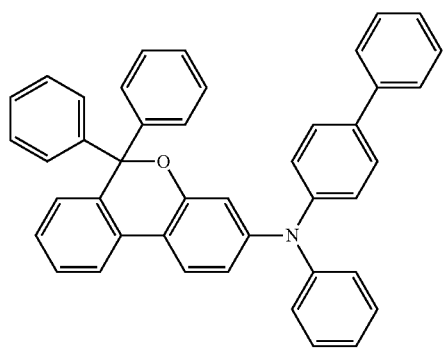
formula 802
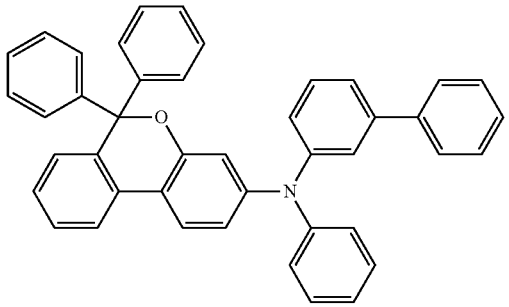
formula 803
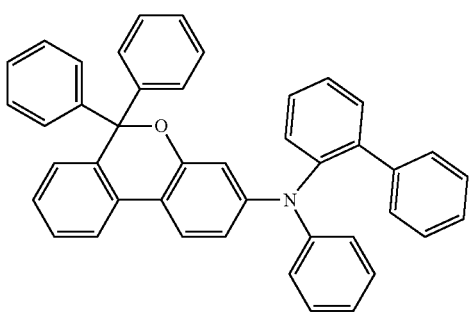
formula 804
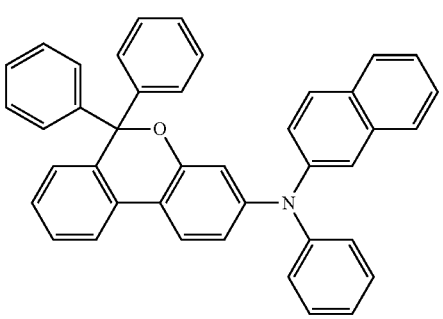
formula 805
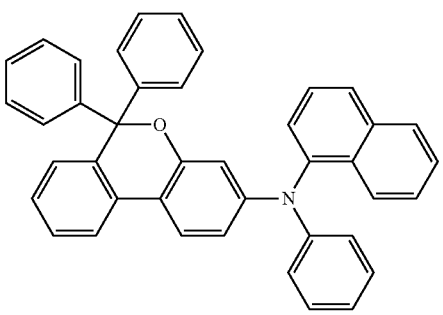
formula 806
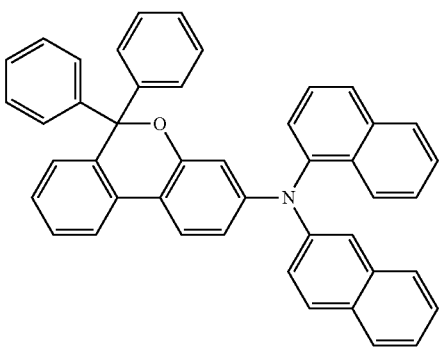

formula 807
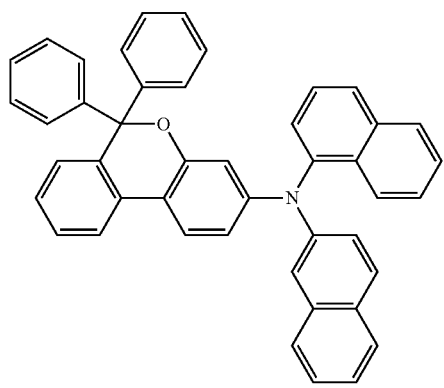
formula 808
formula 809
formula 810
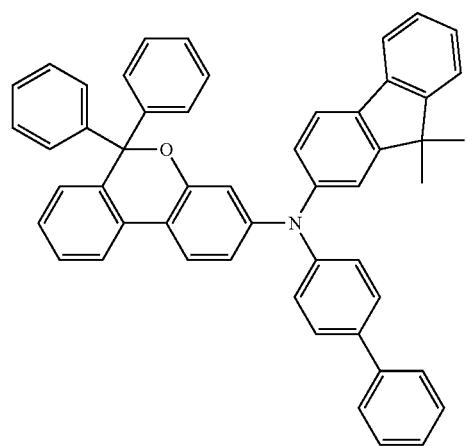
formula 811
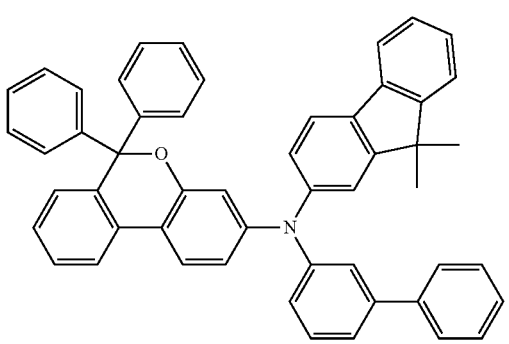
formula 812
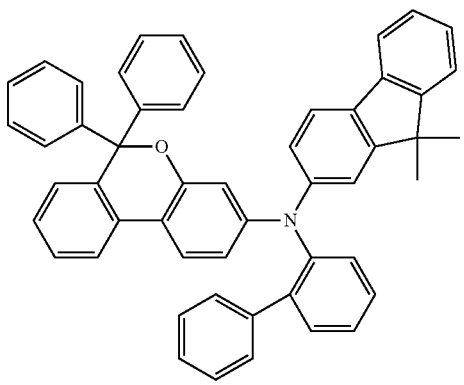
formula 813
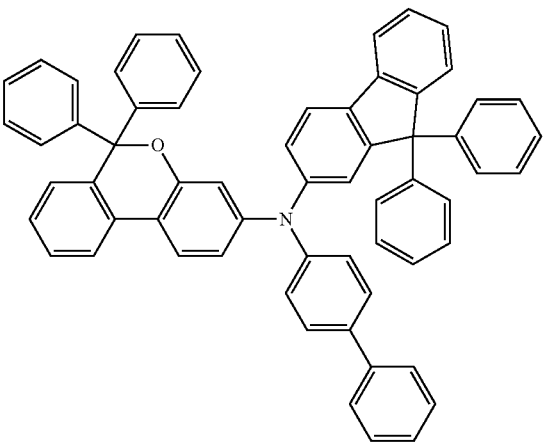
formula 814
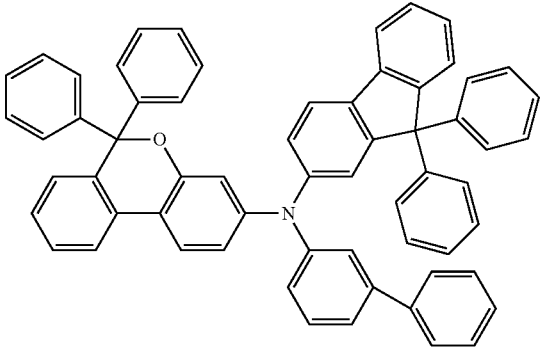

formula 815
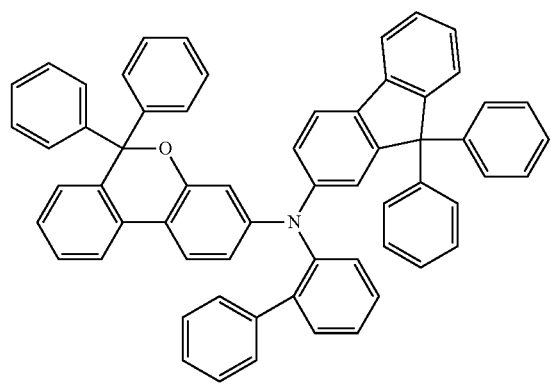
formula 816
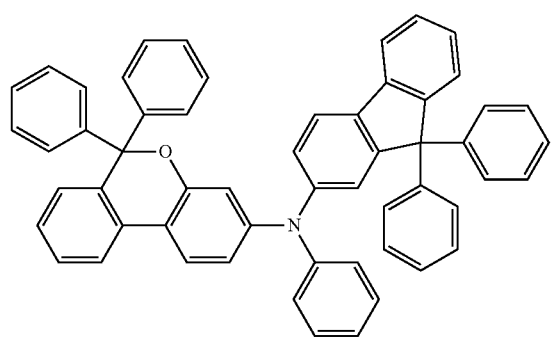
formula 817
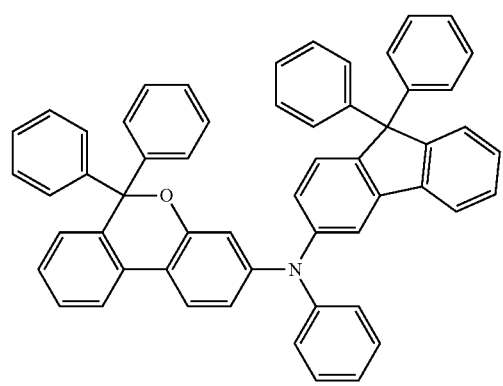
formula 818
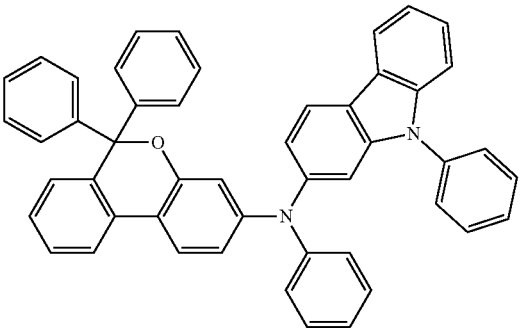
formula 819
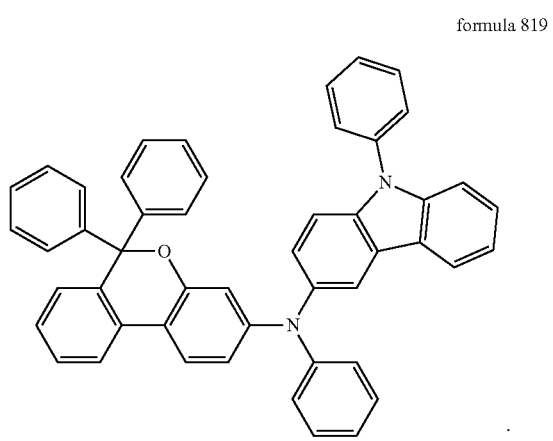
8. An electronic device, comprising a base, an anode, a cathode, and one or more of organic material layers disposed between the anode and the cathode, wherein at least one of the organic layers comprises the oxygen heterocyclic compound according to claim 1.
* * * * *